United States Patent
Ohashi et al.

(10) Patent No.: US 11,358,972 B2
(45) Date of Patent: Jun. 14, 2022

(54) PENTACYCLIC HETEROCYCLES

(71) Applicant: Eisai R&D Management Co., Ltd., Tokyo (JP)

(72) Inventors: Yoshiaki Ohashi, Tsukuba (JP); Yoshihiko Norimine, Tsukuba (JP); Tamaki Hoshikawa, Tsukuba (JP); Yu Yoshida, Tsukuba (JP); Yoshihisa Kobayashi, Tokyo (JP); Nobuhiro Sato, Tsukuba (JP); Koji Hagiwara, Tsukuba (JP); Nobuaki Sato, Tsukuba (JP); Shinsuke Hirota, Tsukuba (JP); Takaaki Harada, Tsukuba (JP); Hikaru Yoshimura, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 6 days.

(21) Appl. No.: 16/807,335

(22) Filed: Mar. 3, 2020

(65) Prior Publication Data
US 2020/0283452 A1    Sep. 10, 2020

(30) Foreign Application Priority Data
Mar. 5, 2019    (JP) .............................. JP2019-039351

(51) Int. Cl.
*C07D 495/22*    (2006.01)
*A61K 31/551*    (2006.01)
(Continued)

(52) U.S. Cl.
CPC ....... *C07D 495/22* (2013.01); *C07D 491/147* (2013.01); *C07D 491/22* (2013.01)

(58) Field of Classification Search
CPC ...... C07D 495/22; A61K 31/551; A61P 25/00
See application file for complete search history.

(56) References Cited

U.S. PATENT DOCUMENTS

| | | |
|---|---|---|
| 4,187,306 A | 2/1980 | Mayer et al. |
| 5,621,100 A | 4/1997 | Lewis et al. |

(Continued)

FOREIGN PATENT DOCUMENTS

| | | |
|---|---|---|
| CL | 200400348 | 1/2005 |
| CL | 200400352 | 5/2005 |

(Continued)

OTHER PUBLICATIONS

US 10,239,899 B2, 03/2019, Ohashi et al. (withdrawn)

(Continued)

*Primary Examiner* — Bruck Kifle
(74) *Attorney, Agent, or Firm* — Fish & Richardson P.C.

(57) ABSTRACT

The present invention provides compounds represented by formulas (I) to (XVII) or pharmaceutically acceptable salts thereof:

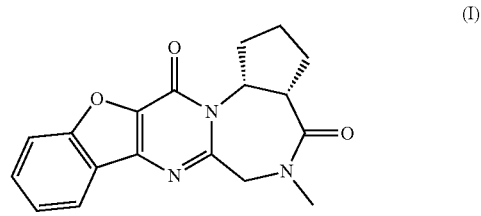

(I)

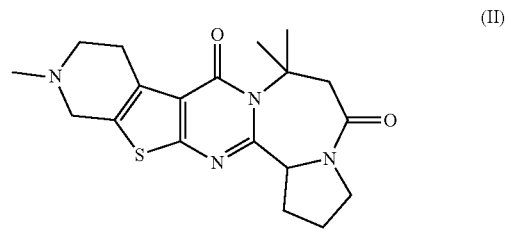

(II)

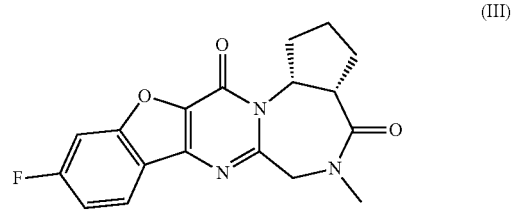

(III)

(IV)

(V)

(VI)

(Continued)

-continued (VII)

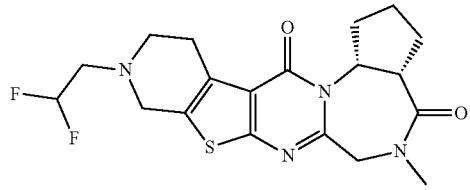

(VIII)

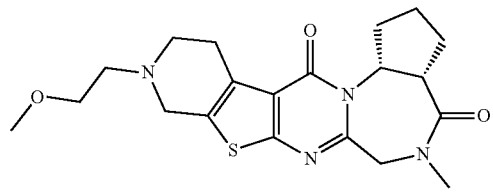

(IX)

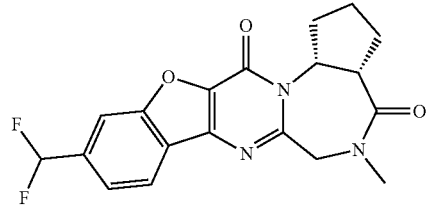

(X)

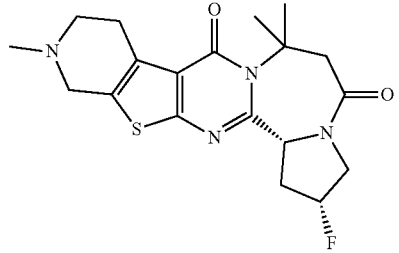

(XI)

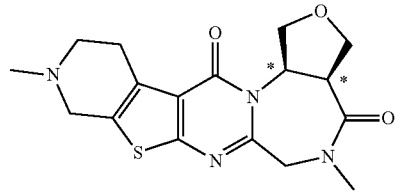

(XII)

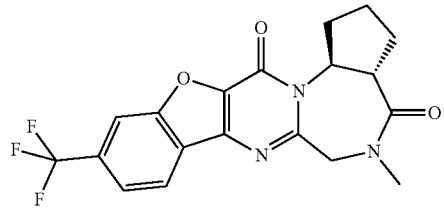

(XIII)

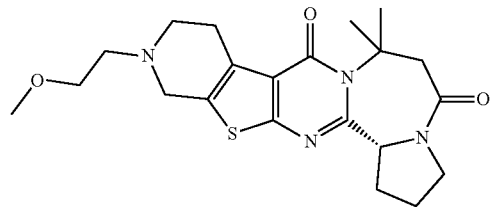

-continued (XIV)

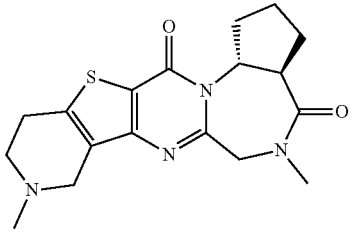

(XV)

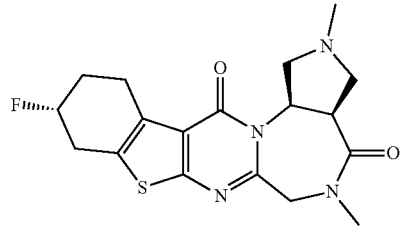

(XVI)

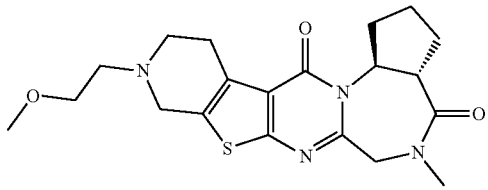

(XVII)

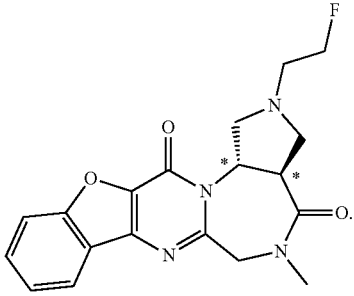

5 Claims, 2 Drawing Sheets

(51) Int. Cl.
*A61P 25/00* (2006.01)
*C07D 491/22* (2006.01)
*C07D 491/147* (2006.01)

(56) References Cited

U.S. PATENT DOCUMENTS

| | | |
|---|---|---|
| 5,756,494 A | 5/1998 | Lewis et al. |
| 5,859,016 A | 1/1999 | Suh et al. |
| 2019/0071452 A1 | 3/2019 | Ohashi et al. |
| 2021/0024541 A1 | 1/2021 | Yoshida et al. |

FOREIGN PATENT DOCUMENTS

| | | |
|---|---|---|
| CN | 1054600 | 9/1991 |
| CN | 101084220 | 12/2007 |
| DE | 258234 | 7/1988 |

(56) References Cited

FOREIGN PATENT DOCUMENTS

| EP | 0441517 | 8/1981 |
|---|---|---|
| JP | S54-024896 | 2/1979 |
| JP | H9-118621 | 5/1997 |
| RU | 2117670 | 8/1998 |
| RU | 2229299 | 5/2004 |
| WO | WO 2004/033666 | 4/2004 |
| WO | WO 2019/049869 | 3/2019 |

OTHER PUBLICATIONS

Notice of Allowance in Taiwanese Patent Application No. 107131095, dated Jun. 18, 2020, 7 pages (with English Translation).
International Search Report in International Application No. PCT/JP2020/008889, dated Jun. 9, 2020, 2 pages.
Office Action in Pakistani Patent Application No. 146/2020, dated Oct. 2, 2020, 2 pages.
Pappas et al., "Choline acetyltransferase activity and cognitive domain scores of Alzheimer's patients", Neurobiology of Aging, 2000, 21: 11-17.
Allen et al., "Abundant tau filaments and nonapoptotic neurodegeneration in transgenic mice expressing human P301S tau protein," The Journal of Neuroscience, 2002, 21:9340-9351.
Bruce et al., "Choline acetyltransferase activity and cognitive domain score of Alzheimer's patients," Neurobiology of Aging, 2000, 21:11-17.
Dautan et al., "A major external source of cholinergic innervation of the striatum and nucleus accumbens originates in the brainstem," The Journal of Neuroscience, 2014, 34(13):4509-4518.
Decker, "Novel inhibitors of acetyl- and butyrylcholinesterase derived from the alkaloids dehydroevodiamine and rutaecarpine," European Journal of Medicinal Chemistry, 2005, 40(3):305-313, ISSN 0223-5234.
Everitt et al., "Central cholinergic systems and cognition," Annu. Rev. Psychol., 1997 48:649-684.
Fischer et al., "Progressive decline in spatial learning and integrity of forebrain cholinergic neurons in rats during aging," Neurobiology of Aging, 1992, 13:9-23.
Gilmor et al., "Coordinate expression of the vesicular acetylcholine transporter and choline acetyltransferase following septohippocampal pathway lesions," Journal of Neurochemistry, 1998, 71:2411-2420.
Gómez-Isla et al., "Neuronal loss correlates with but exceeds neurofibrillary tangles in Alzheimer's disease," American Neurological Association, 1997, 41:17-24.
Gu et al., "Recombinant human NGF-loaded microspheres promote survival of basal forebrain cholinergic neurons and improve memory impairments of spatial learning in the rat model of Alzheimer's disease with fimbria-fornix lesion," Neuroscience Letters, 2009, 453:204-209.
Gulledge et al., "Cholinergic inhibition of neocortical pyramidal neurons," J. Neurosci., 2005, 25:10308-10320.
Hoffmann et al., "Impaired plasticity of cortical dendritic spines in P301S tau transgenic mice," Acta. Neuropathol. Communications, 2013, 1:82.
Huang et al., "A simple heterocyclic fusion reaction and its application for expeditious syntheses of rutaecarpine and its analogs," Tetrahedron Letters, 2014, 55(26):3607-3609.
International Preliminary Report on Patentability in International Patent Application No. PCT/JP2018/032797, dated Mar. 19, 2020, 6 pages.
International Search Report in International Application No. PCT/JP2018/032797, dated Dec. 4, 2018, 12 pages (with English Translation).
Lapchak et al., "Effect of recombinant human nerve growth factor on presynaptic cholinergic function in rat hippocampal slices following partial septohippocampal lesions: measures of [$^3$H]acetylcholine synthesis, [$^3$H] acetylcholine release and choline acetyltransferase activity," Neuroscience, 1991, 42(3):639-649.
Leanza et al., "Selective immunolesioning of the basal forebrain cholinergic system disrupts short-term memory in rats," European Journal of Neuroscience, 1996, 8:1535-1544.
Leanza et al., "Selective lesioning of the basal forebrain cholinergic system by intraventricular 192 IgG-saporin: behavioural, biochemical and stereological studies in the rat," European Journal of Neurosceience, 1995, 7:329-343.
Lee et al., "Neurodegenerative tauopathies," Annu. Rev. Neurosci., 2001, 24:1121-1159.
Lowe et al., "Effects of a novel mGlu$_2$⅔ receptor agonist prodrug, LY2140023 monohydrate, on central monoamine turnover as determined in human and rat cerebrospinal fluid," Psychopharmacology, 2012, 219:959-970.
Mori et al., "Donepezil for dementia with Lewy bodies: a randomized, placebo-controlled trial," Ann. Neurol., 2012, 72:41-52.
Mufson et al., "Cholinergic system during the progression of Alzheimer's disease: therapeutic implication," Expert Rev. Neurother., 2008, 8:1703-1718.
Mufson et al., "Human cholinergic basal forebrain: chemoanatomy and neurologic dysfunction," Journal of Chemical Neuroanatomy, 2003, 26:233-242.
Notice of Allowance in Japanese Patent Application No. P2019-516726, dated Jul. 9, 2019, 5 pages (with English Translation).
Notice of Allowance in United States U.S. Appl. No. 16/122,116, dated Nov. 15, 2018, 10 pages.
Office Action in Gulf Cooperation Council Patent Application No. GC2018-35952, dated Jan. 27, 2020, 9 pages (with English Translation).
Office Action in Japanese Patent Application No. P2019-516726, dated Jun. 11, 2019, 4 pages (with English Translation).
Office Action in Pakistani Patent Application No. 612/2018, dated Dec. 6, 2019, 2 pages.
Ogura et al., "Donepezil, a centrally acting acetylcholinesterase inhibitor, alleviates learning deficits in hypocholinergic models in rats," Methods Find Exp. Clin. Pharmacol., 2000, 22(2):89-95.
Onishi et al., "Early-onset cognitive deficits and axonal transport dysfunction in P301S mutant tau transgenic mice", Neuroscience Research, 2014, 80:76-85.
Perry et al., "Neocortical cholinergic activities differentiate Lewy body dementia from classical Alzheimer's disease," Clinical Neuroscience and Neuropathology, 1994, 5:747-749.
Rogers et al., "The efficacy and safety of donepezil in patients with Alzheimer's disease: results of a US Multicentre, Randomized, Double-Blind, Placebo-Controlled Trial," Dementia, 1996, 7:293-303.
Salehi et al., "Increased App Expression in a Mouse Model of Down's Syndrome Disrupts NGF Transport and Causes Cholinergic Neuron Degeneration," Neuron, 2006, 51:29-42.
Schliebs et al., "The significance of the cholinergic system in the brain during aging and in Alzheimer's disease," J. Neural. Transm., 2006, 113:1625-1644.
Shimada et al., "Mapping of brain acetylcholinesterase alterations in Lewy body disease by PET," Neurology, 2009, 73:273-278.
Spowart-Manning et al., "Spatial discrimination deficits by excitotoxic lesions in the Morris water escape task," Behavioural Brain Research, 2005, 156:269-276.
Steriade et al., "Neuronal activities in brain-stem cholinergic nuclei related to tonic activation processes in thalamocortical systems," Journal of Neuroscience, 1990, 10(8):2541-2559.
Submission Document in Gulf Cooperation Council Patent Application No. GC2020-39301, dated Apr. 22, 2020, 9 pages (with English Translation).
Tiraboschi, et al., "Cholinergic dysfunction in diseases with Lewy bodies," Neurology, 2000, 54:407-411.
Ustalar et al., "Microwave assisted synthesis of 2,3-dihydro-4H-benzo[4,5]thiazolo[3,2-a]furo[2,3-d]pyrimidin-4-ones and 6,7-dihydro-5H-furo[2,3-d]thiazolo[3,2-a]pyrimidin-5-ones using Mn(OAc)$_3$," Tetrahedron Letters, 2016, 58(6):516-519, ISSN 0040-4039.
Vana et al., "Progression of tau pathology in cholinergic Basal forebrain neurons in mild cognitive impairment and Alzheimer's disease," The American Journal of Pathology, 2011, 179(5):2533-2550.

(56) References Cited

OTHER PUBLICATIONS

Xu et al., "Amyloid precursor protein-mediated endocytic pathway disruption induces axonal dysfunction and neurodegeneration," The Journal of Clinical Investigation, 2016, 126(5): 1815-1833.
Xu et al., "Memory deficits correlate with tau and spine pathology in P301S MAPT transgenic mice," Neuropathology and Applied Neurobiology, 2014, 40:833-843.
Yoshiyama et al., "Synapse loss and microglial activation precede tangles in a P301S tauopathy mouse model," Neuron, 2007, 53:337-351.
Hemdan et al., "Uses of 1-(3-Cyano-4,5,6,7-tetrahydrobenzo[b]-thiophen-2-yl)-3-dodecanoylthiourea as a Building Block in the Synthesis of Fused Pyrimidine and Thiazine Systems," Chemical and Pharmaceutical Bulletin, 2015, 63:450-456.
International Search Report in International Application No. PCT/JP2020/008881, dated Jun. 9, 2020, 16 pages (with English Translation).
Submission Document in Vietnamese Patent Application No. 1-2020-00813, dated Jun. 22, 2020, 13 pages (with English Translation).
Submission Document in Chinese Patent Application No. 201880053052.1, dated Jul. 22, 2020, 14 pages (with English Translation).
Submission Document in Korean Patent Application No. 10-2020-7004232, dated May 22, 2020, 7 pages (with English Translation).
Office Action in U.S. Appl. No. 17/021,544, dated Feb. 12, 2021, 14 pages.
Submission Document in European Patent Application No. 18853415.0, dated Feb. 24, 2021, 6 pages.
Submission Document in Vietnamese Patent Application No. 1-2020-00813, dated Feb. 23, 2021, 12 pages (with English Translation).
Notice of Allowance in European Patent Application No. 18853415.0, dated Apr. 8, 2021, 50 pages.
Office Action in U.S. Appl. No. 17/021,544, dated Apr. 8, 2021, 10 pages.
Submission Document in Gulf Cooperation Council Patent Application No. GC2020-39301, dated Mar. 28, 2021, 12 pages (with English Translation).
Submission Document in Israeli Patent Application No. 272652, dated Mar. 11, 2021, 10 pages (with Partial Translation).
Submission Document in U.S. Appl. No. 17/021,544, dated Mar. 26, 2021, 6 pages.
Office Action in Israeli Patent Application No. 272652, dated Nov. 19, 2020, 5 pages (with English Translation).
Office Action in U.S. Appl. No. 17/021,544, dated Dec. 8, 2020, 9 pages.
Search Report in European Patent Application No. 18853415.0, dated Dec. 7, 2020, 5 pages.
Submission Document in Colombian Patent Application No. NC2020/0001471, dated Oct. 6, 2020, 11 pages (with English Translation).
Submission Document in Egyptian Patent Application No. PCT292/2020, dated Dec. 29, 2020, 7 pages (with English Translation).
Submission Document in Peruvian Patent Application No. 000228-2020/DIN, dated Dec. 9, 2020, 8 pages (with English Translation).
Submission Document in South African Patent Application No. 2020/00970, dated Dec. 8, 2020, 6 pages.
Submission Document in U.S. Appl. No. 17/021,544, dated Oct. 15, 2020, 80 pages.
Submission Document in U.S. Appl. No. 17/021,544, dated Jan. 26, 2021, 5 pages.
Notice of Allowance in Russian Patent Application No. 2020106798, dated Aug. 5, 2021, 20 pages (with English Translation).
Submission Document in Indian Patent Application No. 202047005838, dated Jul. 28, 2021, 7 pages.
Submission Document in Argentine Patent Application No. 20200100583, dated Jul. 23, 2021, 154 pages (with English Translation).
Submission Document in Indonesian Patent Application No. P00202001255, dated Jul. 30, 2021, 88 pages (with English Translation).
Notice of Allowance in South African Patent Application No. 2020/00970, dated May 24, 2021, 2 pages.
Office Action in Argentine Patent Application No. 20200100583, dated Mar. 31, 2021, 18 pages (with English Translation).
Office Action in Chilean Patent Application No. 202000376, dated Mar. 15, 2021, 30 pages (with English Translation).
Office Action in Russian Patent Application No. 2020106798, dated Apr. 22, 2021, 15 pages (with English Translation).
Official Notification in U.S. Appl. No. 17/021,544, dated Jul. 7, 2021, 18 pages.
Submission Document in Brazilian Patent Application No. BR1120200031976, dated Jun. 29, 2021, 30 pages (with English Translation).
Submission Document in Chilean Patent Application No. 202000376, dated May 28, 2021, 85 pages (with English Translation).
Submission Document in Russian Patent Application No. 2020106798, dated Jun. 7, 2021, 14 pages (with English Translation).
Submission Document in Ukrainian Patent Application No. a202000934, dated Jul. 29, 2021, 10 pages (with English Translation).
Notice of Allowance in Korean Patent Application No. 10-2020-7004232, dated Aug. 19, 2021, 4 pages (with English Translation).
Office Action in Chinese Patent Application No. 202080014060.2, dated Aug. 31, 2021, 2 pages (with English Translation).
Office Action in Indian Patent Application No. 202047005838, dated Aug. 27, 2021, 6 pages (with English Translation).
Submission Document in Australian Patent Application No. 2018330578, dated Sep. 10, 2021, 20 pages.
Office Action in Gulf Cooperation Council Patent Application No. GC2018-35952, dated Jul. 26, 2021, 53 pages (with English Translation).
Office Action in Vietnamese Patent Application No. 1-2021-04971, dated Sep. 24, 2021, 4 pages (with English Translation).
Submission Document in Gulf Cooperation Council Patent Application No. GC2018-35952, dated Oct. 17, 2021, 86 pages (with English Translation).
Notice of Allowance in Chilean Patent Application No. 202000376, dated Oct. 15, 2021, 10 pages (with English Translation).
Office Action in Chinese Patent Application No. 201880053052.1, dated Nov. 25, 2021, 10 pages (with English Translation).
Office Action in Indonesian Patent Application No. P00202001255, dated Dec. 20, 2021, 9 pages (with English Translation).
Chen et al., "Pharmaceutical Crystallization," Crystal Growth & Design, 2011, 11:887-895.
Office Action in U.S. Appl. No. 17/021,544, dated Jan. 14, 2022, 57 pages.
Official Notification in Colombian Patent Application No. NC2020/0001471, dated Dec. 29, 2021, 3 pages (with English Translation).
Office Action in Colombian Patent Application No. NC2020/0001471, dated Jan. 7, 2022, 10 pages (with English Translation).
Office Action in Israeli Patent Application No. 272652, dated Feb. 1, 2022, 3 pages.
Submission Document in Chinese Patent Application No. 20208001460.2, dated Feb. 14, 2022, 24 pages (with English Translation).
Submission Document in Singaporean Patent Application No. 11202108780P, dated Feb. 21, 2022, 13 pages.
Office Action in Israeli Patent Application No. 285511, dated Mar. 2, 2022, 5 pages (with English Translation).
Submission Document in Chinese Patent Application No. 201880053052.1, dated Mar. 9, 2022, 20 pages (with English Translation).
Submission Document in Indonesian Patent Application No. P00202001255, dated Mar. 18, 2022, 9 pages (with English Translation).
Office Action in Gulf Cooperation Council Patent Application No. GC2020-39301, dated Oct. 24, 2021, 9 pages (with English Translation).
Submission Document in Vietnamese Patent Application No. 1-2021-04971, dated Nov. 10, 2021, 14 pages (with English Translation).
Notice of Allowance in Chinese Patent Application No. 201880053052.1, dated Mar. 28, 2022, 4 pages (with English Translation).
Submission Dcoument in Colombian Patent Application No. NC2020/0001471, dated Mar. 25, 2022, 20 pages (with English Translation).

(56) References Cited

OTHER PUBLICATIONS

Submission Document in U.S. Appl. No. 17/021,544, dated Mar. 29, 2022, 9 pages.
Notice of Allowance in U.S. Appl. No. 17/021,544, dated Apr. 19, 2022 17 pages.

PENTACYCLIC HETEROCYCLES

CROSS-REFERENCE TO RELATED APPLICATION

This application claims the benefit of Japanese patent application No. 2019-039351 filed on Mar. 5, 2019, the disclosure of which is herein incorporated by reference in its entirety.

TECHNICAL FIELD

The present invention relates to a pentacyclic heterocycle or a pharmaceutically acceptable salt thereof, having cholinergic neuron activation effect. The invention further relates to a pharmaceutical composition comprising the same as active ingredients.

BACKGROUND

Cholinergic neurons which release acetylcholine as a transmitter are widely projected in the forebrain from the nucleus basalis of Meynert and the septal nucleus of the basal forebrain to the hippocampus, amygdala, and cerebral cortex, and are involved in the modulation of memory, learning, cognition, and attention (Non-Patent Literature 1). Moreover, cholinergic neurons in the pedunculopontine tegmental nucleus and laterodorsal tegmental nucleus of the brain stem are projected in the striatum, accumbens nucleus, substantia nigra, and thalamus, and are considered to be involved in the control of motivation and vigilance (Non-Patent Literatures 2 to 4).

In particular, the role of cholinergic neurons in the basal forebrain has been more clarified by analysis using many animal models such as lesion model. Especially, the correlation between functional disorder of cholinergic neurons and decreased memory and learning has been shown in the animal models (Non-Patent Literatures 5 to 7), and it has been shown that cognitive performance is improved by increasing the amount of acetylcholine using a cholinesterase inhibitor, and enhancing the function of cholinergic neurons (Non-Patent Literatures 8 and 9).

The dysfunction of cholinergic neuron is also seen in most cognitive dysfunction-associated neurological disease (Non-Patent Literature 10). Particularly, in Alzheimer's disease and dementia with Lewy bodies, a correlation between dysfunction of cholinergic neuron and impaired cognitive function is known (Non-Patent Literatures 11 to 13), cognitive function has been shown to be improved with cholinesterase inhibitors, as in animal models such as lesion model (Non-Patent Literatures 14 and 15).

Therefore, based on these findings, an improvement in reduced cognitive performance caused by the dysfunction of cholinergic neurons can be expected by achieving functional activation effect on cholinergic neurons in clinical practice.

In addition to the above diseases, examples of diseases for which association between decrease in cognitive function and the dysfunction of cholinergic neurons has been reported include Huntington's chorea, Down's syndrome, amyotrophic lateral sclerosis (ALS), major depression, schizophrenia, and the like.

CITATION LIST

Non-Patent Literature

[Non-Patent Literature 1] Everitt B J et al. "Central cholinergic systems and cognition." Annu. Rev. Psychol. 48 (1997) 649-684

[Non-Patent Literature 2] Gulledge A T et al. "Cholinergic inhibition of neocortical pyramidal neurons." J. Neurosci. 25 (2005) 10308-20

[Non-Patent Literature 3] Daniel Dautan D. et al. "A major external source of cholinergic innervation of the striatum and nucleus accumbens originates in the brainstem." J. Neurosci. 34 (2014) 4509-18

[Non-Patent Literature 4] Steriade M. et al. "Neuronal activities in brain-stem cholinergic nuclei related to tonic activation processes in thalamocortical systems." J. Neurosci. 10 (1990) 2541-59

[Non-Patent Literature 5] Fischer W. et al. "Progressive decline in spatial learning and integrity of forebrain cholinergic neurons in rats during aging." Neurobiol. Aging 13 (1992) 9-23

[Non-Patent Literature 6] Leanza G. et al. "Selective lesioning of the basal forebrain cholinergic system by intraventricular 192 IgG-saporin: behavioural, biochemical and stereological studies in the rat" Eur. J. Neurosci. 7 (1995) 329-43

[Non-Patent Literature 7] Leanza G. et al. "Selective immunolesioning of the basal forebrain cholinergic system disrupts short-term memory in rats." Eur. J. Neurosci. 8 (1996) 1535-44

[Non-Patent Literature 8] Ogura H. et al. "Donepezil, a centrally acting acetylcholinesterase inhibitor, alleviates learning deficits in hypocholinergic models in rats." Methods Find Exp Clin Pharmacol. 22 (2000) 89-95.

[Non-Patent Literature 9] Spowart-Manning L. et al. "Spatial discrimination deficits by excitotoxic lesions in the Morris water escape task." Behav Brain Res. 156 (2005) 269-76.

[Non-Patent Literature 10] Mufson E J. et al. "Human cholinergic basal forebrain: chemoanatomy and neurologic dysfunction." J. Chem. Neuroanat. 26 (2003) 233-242

[Non-Patent Literature 11] Mufson E J. et al. "Cholinergic system during the progression of Alzheimer's disease: therapeutic implication." Expert. Rev. Neurother. 8 (2008) 1703-1718

[Non-Patent Literature 12] Schliebs R. et al. "The significance of the cholinergic system in the brain during aging and in Alzheimer's disease." J. Neural. Transm 113 (2006) 1625-1644

[Non-Patent Literature 13] Bruce A P. et al. "Choline acetyltransferase activity and cognitive domain score of Alzheimer's patients." Neurobiol. Aging. 21 (2000) 11-17

[Non-Patent Literature 14] Rogers S L. et a "The efficacy and safety of donepezil in patients with Alzheimer's disease: results of a US Multicentre, Randomized, Double-Blind, Placebo-Controlled Trial. The Donepezil Study Group." Dementia. 7 (1996) 293-303

[Non-Patent Literature 15] Mori E. et at "Donepezil for dementia with Lewy bodies: a randomized, placebo-controlled trial." Ann Neurol. 72 (2012) 41-52

SUMMARY

It is an object of the present invention to provide a compound or a pharmaceutically acceptable salt thereof having cholinergic neuron activation effect and having a potential use of a therapeutic agent for cognitive dysfunction.

As a result of extensive studies to solve the above problems, the present inventors found a pentacyclic heterocycle or a pharmaceutically acceptable salt thereof having cholinergic neuron activation effect.

Specifically, the invention relates to the following <1> to <9>.

<1> A compound selected from the group consisting of (3aS,14aR)-5-Methyl-3,3a,5,6-tetrahydro-1H-benzofuro[3',2':4,5]pyrimido[1,2-a]cyclopenta[f][1,4]diazepine-4,13(2H,14aH)-dione:

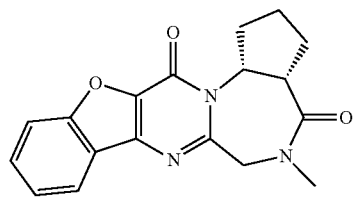
(I)

(+)-7,7,12-Trimethyl-1,2,3,6,7,10,11,12,13,15b-decahydropyrido[4",3':4',5']thieno[2',3':4,5]pyrimido[1,2-a]pyrrolo[2,1-c][1,4]diazepine-5,9-dione:

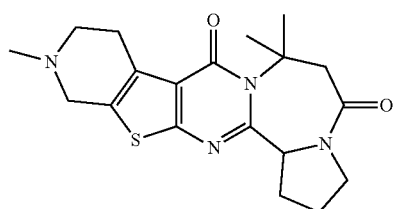
(II)

(3aS,14aR)-10-Fluoro-5-methyl-3,3a,5,6-tetrahydro-1H-benzofuro[3',2':4,5]pyrimido[1,2-a]cyclopenta[f][1,4]diazepine-4,13(2H,14aH)-dione:

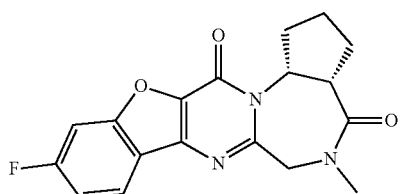
(III)

(3aS,14aR)-5,8,10-Trimethyl-3,3a,5,6-tetrahydro-1H-cyclopenta[f]pyrido[3",2":4',5']furo[3',2':4,5]pyrimido[1,2-a][1,4]diazepine-4,13(2H,14aH)-dione:

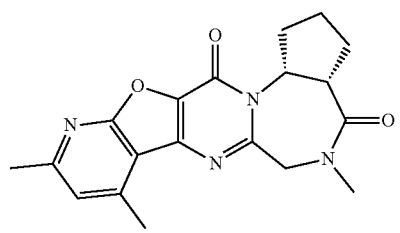
(IV)

(3aR,14aR)-10-Fluoro-5-methyl-3,3a,5,6-tetrahydro-1H benzofuro[3',2':4,5]pyrimido[1,2-a]cyclopenta[f][1,4]diazepin-4,13(2H,14aH)-dione:

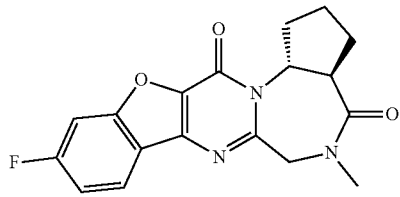
(V)

(3aR,14aR)-5-Methyl-10-(trifluoromethyl)-3,3a,5,6-tetrahydro-1H-benzofuro[3',2':4,5]pyrimido[1,2-a]cyclopenta[f][1,4]diazepine-4,13(2H,14aH)-dione:

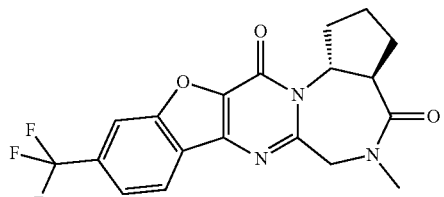
(VI)

(3aS,14aR)-10-(2,2-Difluorophenyl)-5-methyl-2,3,3a,5,6,9,10,11,12,14a-decahydro-1H-cyclopenta[f]pyrido[4",3":4',5']thieno[2',3':4,5]pyrimido[1,2-a][1,4]diazepine-4,13-dione:

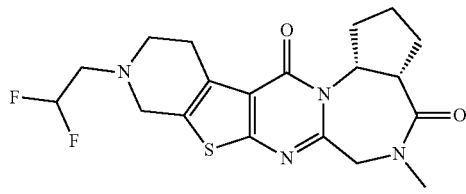
(VII)

(3aS,14aR)-10-Methoxyethyl-5-methyl-3,3a,5,6,9,10,11,12,14a-decahydro-1H-cyclopenta[f]pyrido[4,"3":4',5']thieno[2',3':4,5]pyrimido[1,2-a][1,4]diazepine-4,13-dione:

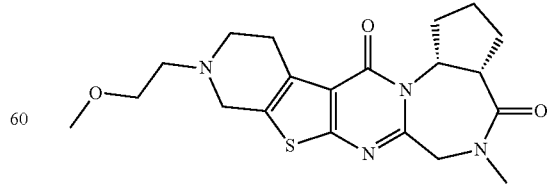
(VIII)

(3a,4a)-10-(Difluoromethyl)-5-methyl-3,3a,5,6-tetrahydro-1H-benzofuro[3',2':4,5]pyrimido[1,2-a]cyclopenta[f][1,4]diazepine-4,13(2H,14aH)-dione:

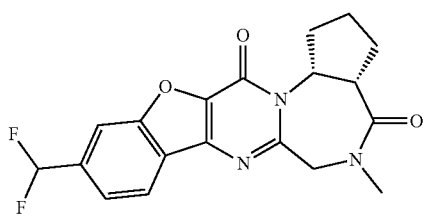

(IX)

(2R,15bR)-2-Fluoro-7,7,12-trimethyl-1,2,3,6,7,10,11,12,13,
15b-decahydro-5H,9H-pyrido[4",3":4',5']thieno[2',3':4,5]
pyrimido[1,2-a]pyrrolo[2,1-c][1,4]diazepine-5,9-dione:

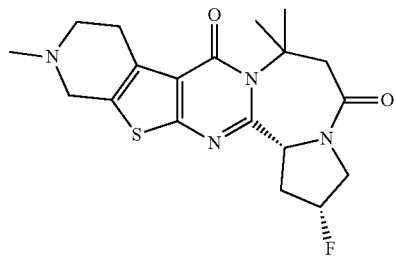

(X)

(+)-3a,14a-cis-5,10-Dimethyl-1,3,3a,5,6,9,10,11,12,14a-
decahydrofuro[3,4-f]pyrido[4",3":4',5']thieno[2',3':4,5]py-
rimido[1,2-a][1,4]diazepine-4,13-dione:

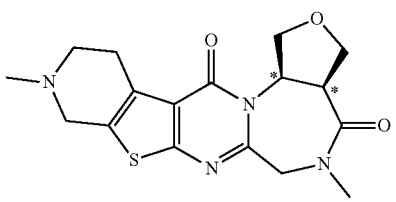

(XI)

* relative configuration (3aS,14aS)-5-Methyl-10-(trifluormethyl)-2,3,3a,5,6,14a-
hexahydro-1H-benzofuro[3',2':4,5]pyrimido[1,2-a]cyclo-
penta[f][1,4]diazepine-4,13-dione:

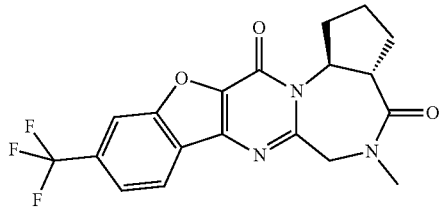

(XII)

(−)-12-(2-Methoxyethyl)-7,7-dimethyl-1,2,3,6,7,10,11,12,
13,15b-decahydro-5H,9H-pyrido[4",3":4',5']thieno[2',3':4,
5]pyrimido[1,2-a]pyrrolo[2,1-c][1,4]diazepine-5,9-dione:

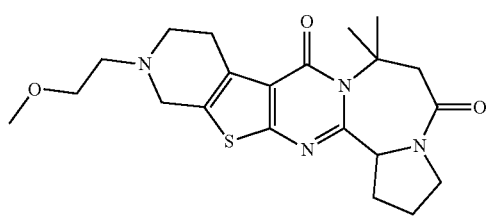

(XIII)

(3aR,14aR)-5,9-Dimethyl-2,3,3a,5,6,8,9,10,11,14a-deca-
hydro-1H-cyclopenta[f]pyrido[3",4":4',5']thieno[3',2':4,5]
pyrimido[1,2-a][1,4]diazepine-4,13-dione:

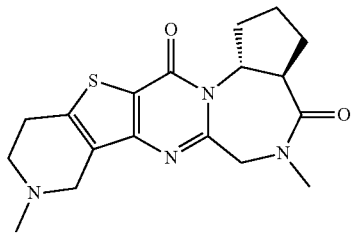

(XIV)

(3aR,10R,14aR)-10-Fluoro-2,5-dimethyl-2,3,3a,5,6,9,10,
11,12,14a-decahydro-1H-benzo[4',5']thieno[2',3':4,5]py-
rimido[1,2-a]pyrrolo[3,4-f][1,4]diazepine-4,13-dione:

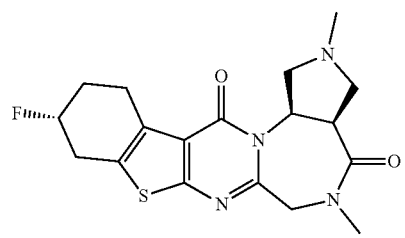

(XV)

(3aS,14aS)-10-(2-Methoxyethyl)-5-methyl-2,3,3a,5,6,9,10,
11,12,14a-decahydro-1H-cyclopenta[f]pyrido[4",3":4',5']
thieno[2',3':4,5]pyrimido[1,2-a][1,4]diazepine-4,13-dione:

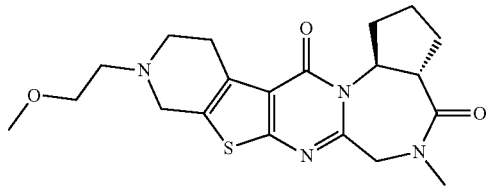

(XVI)

and (−)-(3a,14a-trans)-2-(2-Fluoroethyl-5-methy-2,3,3a,5,6,
14a-hexahydro-1H benzofuro[3',2':4,5]pyrimido[1,2-a]pyr-
rolo[3,4-f][1,4]diazepine-4,13-dione:

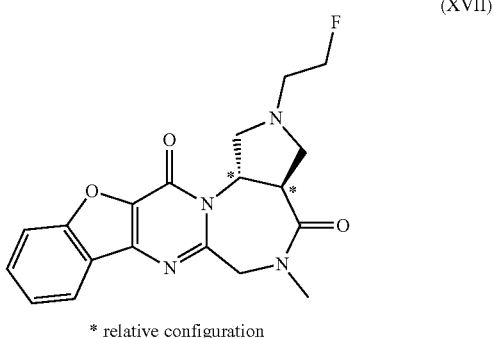 [SMILES: CN1Cc2nc3c(oc4ccccc43)c(=O)n2[C@@H]2CN(CCF)C[C@H]2C1=O]

(XVII)

* relative configuration or a pharmaceutically acceptable salt thereof.

<2> A pharmaceutical composition comprising the compound or pharmaceutically acceptable salt thereof according to <1>.

<3> The pharmaceutical composition according to <2>, further comprising one or more pharmaceutically acceptable excipients.

<4> The pharmaceutical composition according to <2> or <3>, which is a neuron activating agent.

<5> The pharmaceutical composition according to <2> or <3>, for treatment of cognitive dysfunction.

<6> A therapeutic agent for cognitive dysfunction comprising the compound or pharmaceutically acceptable salt thereof according to <1>.

<7> A method for treating cognitive dysfunction comprising administering the compound or pharmaceutically acceptable salt thereof according to <1> to a patient in need thereof.

<8> The compound or pharmaceutically acceptable salt thereof according to <1> for use in the treatment of cognitive dysfunction.

<9> Use of the compound or pharmaceutically acceptable salt thereof according to <1>, for the manufacture of a therapeutic agent for cognitive dysfunction.

The pentacyclic heterocycles represented by formulas (I) to (XVII) (hereunder referred to as "compounds (I) to (XVII)") or pharmaceutically acceptable salts thereof according to the invention have neuron activation effect, as shown in activity data in Pharmacological Test Examples below. Since compounds (I) to (XVII) of the invention lead to an improvement of cognitive performance due to their neuron activation effect, and thus have a potential use as therapeutic agents for cognitive dysfunction.

DETAILED DESCRIPTION

Figure 1:
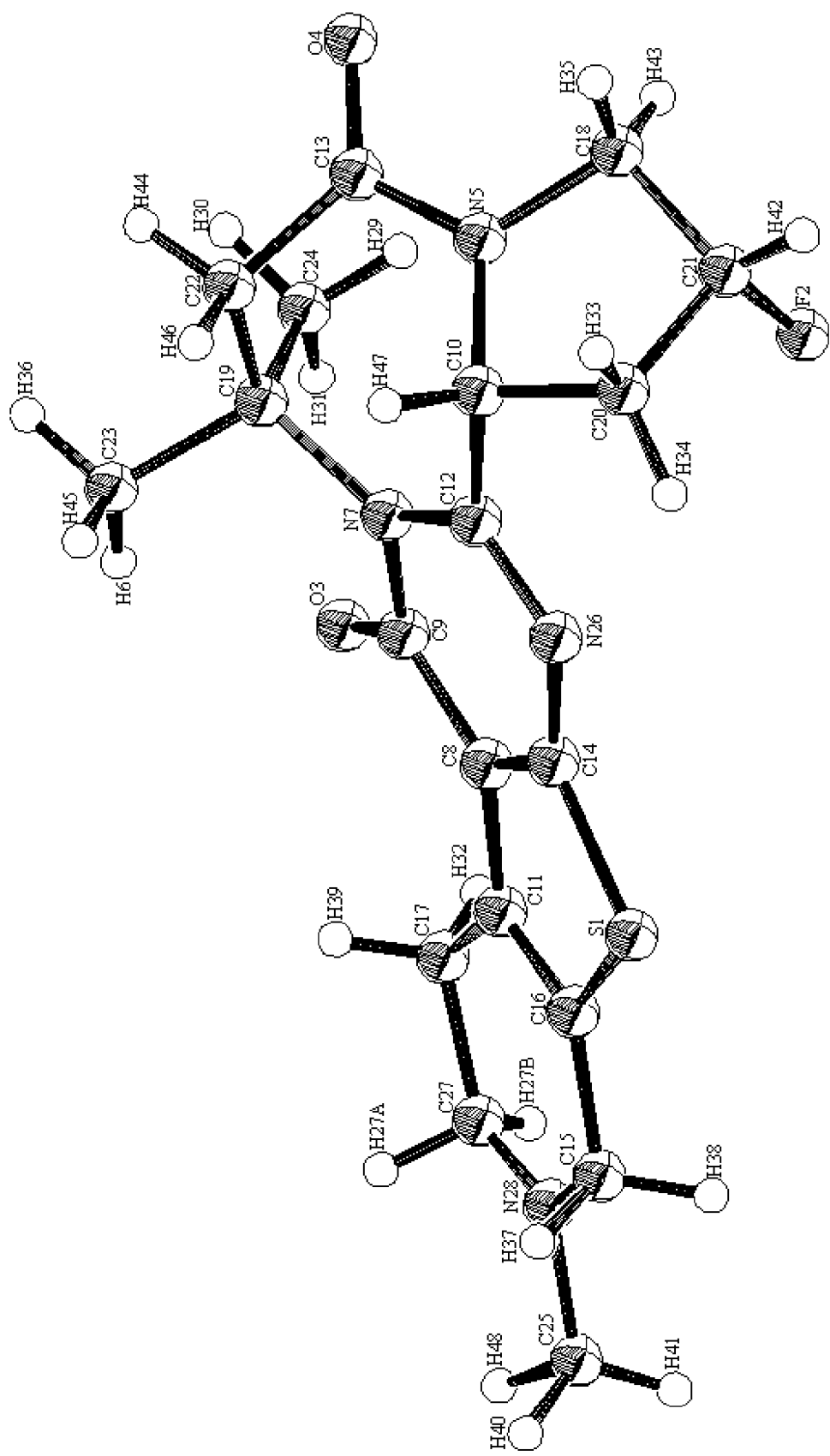
FIG. 1 is an ORTEP diagram showing the results of X-ray crystallographic analysis of the compound obtained in Example 10.

The present invention will now be explained in detail.

In the present specification, the structural formulas of the compounds may represent specific isomers for convenience; however, the present invention may include rotational isomers and tautomers, as well as isomeric mixtures, is not limited to the formulas described for convenience, and may be any of the isomers or a mixture containing the isomers in any proportion.

Further, polymorphic crystals may also exist; however, the present invention is also not limited to any of them and may be a singly crystal form or a mixture thereof. Moreover, the present invention also includes amorphous forms, and the compounds according to the present invention include anhydrates and solvates (particularly hydrates).

The present invention also includes isotope-labeled compounds of the compounds (I) to (XVII). The isotope-labeled compounds are the same as the compounds (I) to (XVII), except that one or more atoms are replaced by one or more atoms having an atomic mass or mass number different from those generally found in nature. Examples of isotopes that can be incorporated into the compounds of the present invention include isotopes of hydrogen, carbon, nitrogen, oxygen, fluorine, phosphorus, sulfur, iodine, and chlorine, and specifically include $^{2}H$, $^{3}H$, $^{11}C$, $^{14}C$, $^{15}N$, $^{18}O$, $^{18}F$, $^{32}P$, $^{35}S$, $^{123}I$, $^{125}I$, and the like.

The above isotope-labeled compounds, for example, compounds into which radioactive isotopes, such as $^{3}H$ and/or $^{14}C$, are incorporated, are useful for the tissue distribution assay of medicines and/or substrates. $^{3}H$ and $^{14}C$ are considered to be useful because of the ease of the preparation and detection thereof. Isotopes $^{11}C$ and $^{18}F$ are considered to be useful for PET (positron emission tomography), isotope $^{125}I$ is considered to be useful for SPECT (single-photon emission computed tomography), and all of them are useful for brain imaging. Replacement by heavier isotopes, such as $^{2}H$, results in some types of therapeutic advantages, including an increase in the in vivo half-life period or a decrease in the required dose due to higher metabolic stability, and is therefore considered to be useful under certain situations. The above isotope-labeled compounds can be similarly prepared by carrying out the procedures disclosed in the following Examples using easily usable reagents labeled with isotopes in place of reagents not labeled with isotopes.

The "pharmaceutically acceptable salts" in the present specification are not particularly limited as long as they are salts formed with the compounds according to the present invention, and specific examples include acid addition salts, such as inorganic acid salts, organic acid salts, and acidic amino acid salts.

The "pharmaceutically acceptable salt" in the present specification is any salt formed in a suitable ratio unless there is any especially limiting description, and the number of acid molecules per molecule of the compound in the formed salt is not particularly limited; however, it is preferable that the number of acid molecules per molecule of the compound be about 0.5 to about 2, and it is more preferable that the number of acid molecules per molecule of the compound be about 0.5, about 1, or about 2.

Preferable examples of the inorganic acid salts include hydrochloride, hydrobromide, sulfate, nitrate, and phosphate; and preferable examples of organic acid salts include acetate, succinate, fumarate, maleate, tartrate, citrate, lactate, stearate, benzoate, methanesulfonate, p-toluenesulfonate, and benzenesulfonate.

Preferable examples of the acidic amino acid salts include aspartate and glutamate.

When the compounds (I) to (XVII) according to the present invention are obtained in a free form, they can be converted into salts that may be formed by the compounds (I) to (XVII) or hydrates thereof in accordance with a conventional method.

When the compounds (I) to (XVII) according to the present invention are obtained as salts of the compounds (I) to (XVII) or hydrates of the compounds (I) to (XVII), they can be converted into free forms of the compounds (I) to (XVII) in accordance with a conventional method.

Moreover, various isomers (e.g., optical isomers, rotational isomers, stereoisomers, etc.) obtained from the compounds (I) to (XVII) according to the present invention can be purified and isolated by general separation means, such as recrystallization, diastereomeric salt method, enzymatic resolution method, and various chromatographic techniques (e.g., thin-layer chromatography, column chromatography, gas chromatography, etc.).

[Pharmaceutical Preparation]

The pharmaceutical composition according to the present invention can be produced by mixing pharmaceutically acceptable additives with a compound selected from the group of compounds (I) to (VI) or pharmaceutically acceptable salts thereof. The pharmaceutical composition according to the present invention can be produced by a known method, for example, the method described in the General Rules for Preparations of The Japanese Pharmacopoeia Seventeenth Edition.

The pharmaceutical composition according to the present invention can be appropriately administered to a patient depending on the dosage form thereof.

The dose of the compounds (I) to (XVII) according to the present invention or pharmaceutically acceptable salts thereof varies depending on the severity of symptoms, age, sex, body weight, dosage form, type of salt, specific type of disease, and other conditions; however, in general, the dose for an adult per day by oral administration is about 30 μg to 10 g, preferably 100 μg to 5 g, and more preferably 100 μg to 1 g; the dose for an adult per day by injection administration is about 30 μg to 1 g, preferably 100 μg to 500 mg, and more preferably 100 μg to 300 mg; and the above dose is administered once or several times.

The compounds of the present invention can be used as chemical probes for capturing the target proteins of bioactive low-molecular-weight compounds. That is, the compounds of the present invention can be converted into affinity chromatography probes, photoaffinity probes, etc., by introducing labeling groups, linkers, or the like into a moiety different from a structural moiety essential for the development of the activity of the compounds using a method described, for example, in J. Mass Spectrum Soc. Jpn. Vol. 51, No. 5, 2003, pp. 492-498, WO2007/139149, or the like.

Examples of labeling groups, linkers, etc., used in chemical probes include groups shown in the group consisting of the following (1) to (5):
(1) protein-labeling groups, such as photoaffinity-labeling groups (e.g., a benzoyl group, a benzophenone group, an azide group, a carbonylazide group, a diaziridine group, an enone group, a diazo group, a nitro group, etc.) and chemical affinity groups (e.g., a ketone group in which the alpha carbon atom is replaced by a halogen atom, a carbamoyl group, an ester group, an alkylthio group, a Michael acceptor such as α,β-unsaturated ketone or ester, and an oxirane group);
(2) cleavable linkers, such as —S—S—, —O—Si—O—, monosaccharides (a glucose group, a galactose group, etc.), or disaccharides (lactose, etc.); and oligopeptide linkers cleavable by enzyme reaction;
(3) fishing tag groups, such as biotin and a 3-(4,4-difluoro-5,7-dimethyl-4H-3a,4a-diaza-4-bora-s-indacen-3-yl)propionyl group;
(4) radioactive labeling groups, such as $^{125}$I, $^{32}$P, $^{3}$H and $^{14}$C; fluorescent labeling groups, such as fluorescein, rhodamine, dansyl, umbelliferone, 7-nitrofurazanyl, and a 3-(4,4-difluoro-5,7-dimethyl-4H-3a,4a-diaza-4-bora-s-indacen-3-yl) propionyl group; chemiluminescent groups, such as luciferin and luminol; and markers capable of detecting heavy metal ions, such as lanthanoid metal ions and radium ions; or
(5) groups to be attached to solid carriers, such as glass beads, glass beds, microtiter plates, agarose beads, agarose beds, polystyrene beads, polystyrene beds, nylon beads, and nylon beds.

Probes prepared by introducing labeling groups, etc., selected from the group consisting of the above (1) to (5) into the compounds of the present invention by the methods described in the above documents or the like can be used as chemical probes for identifying labeled proteins useful to search novel drug design targets, etc.

EXAMPLES

The compounds (I) to (XVII) of the present invention can be produced by, for example, the methods described in the following Examples, and the effects of the compounds can be confirmed by the methods described in the following Test Examples. However, these are just examples, and the present invention is not limited to the following specific examples in any case and may be modified within a range that does not depart from the scope of the present invention.

Compounds described with document names, etc., indicate that the compounds were produced according to the documents, etc.

Moreover, the abbreviations used in the present specification are well-known and common to a person skilled in the art. In the present specification, the following abbreviations are used.

DAST: Diethylaminosulfur trifluoride
DCE: 1,2-Dichloroethane
DCM: Dichloromethane
DIPEA: N,N-Diisopropylethylamine
DMF: N,N-Dimethylformamide
DMT-MM: 4-(4,6-Dimethoxy-1,3,5-triazin-2-yl)-4-methylmorpholinium chloride
DMSO: Dimethyl sulfoxide
EDC: 1-Ethyl-3-(3-dimethylaminopropyl)carbodiimide hydrochloride
HATU: O-(7-Azabenzotriazol-1-yl)-N,N,N',N'-tetramethyluronium hexafluorophosphate
HOBT: 1-Hydroxybenzotriazole
n-: normal
NMM: N-Methylmorpholine
SFC: Supercritical Fluid Chromatography
t-: tertiary
TBD: 1,3,4,6,7,8-Hexahydro-2H-pyrimido[1,2-a]pyrimidine
TBME: tertiary-Butyl methyl ether
TEA: Triethylamine
TFA: Trifluoroacetic acid
THF: Tetrahydrofuran
$^{1}$H-NMR Proton Nuclear Magnetic Resonance spectrometry
MS: Mass Spectrometry
HPLC: High-Performance Liquid Chromatography The term "room temperature" in the following Examples and Production Examples generally refers to about 10° C. to about 35° C. % refers to weight percent unless otherwise specified.

Chemical shifts of proton nuclear magnetic resonance spectra are denoted in δ-unit (ppm) relative to tetramethylsilane, and coupling constants are recorded in Hertz (Hz). Patterns are designated as s: singlet, d: doublet, t: triplet, q: quartet, m: multiplet, br: broad, br.s: broad singlet.

For the optical resolution of the compound, Parallex Flex™ produced by Biotage (column: one of CHIRAL-PAK™ AD-H, IA, IB, IC and IF produced by DAICEL; and CHIRALCEL™ OD-H and OJ-H produced by DAICEL) was used.

In the reactions using a microwave reactor in the Production Examples, Reference Examples, and Examples, Initiator™ or Initiator+™ produced by Biotage was used.

Regarding chromatography, as silica gel, Silica Gel60 produced by Merck (70-230 mesh or 230-400 mesh ASTM) or PSQ60B produced by Fuji Silysia Chemical Ltd. was used, or a pre-packed column {column: Hi-Flash™ Column (Silicagel) produced by YAMAZEN, size: one of S (16×60 mm), M (20×75 mm), L (26×100 mm), 2 L (26×150 mm), and 3 L (46×130 mm); or Biotage™ SNAP Ultra Silica Cartridge produced by Biotage, size: one of 10 g, 25 g, and 50 g} was used.

As NH silica gel, CHROMATOREX NH-DM2035 produced by Fuji Silysia Chemical Ltd. was used, or a pre-packed column {column: Hi-Flash™ Column (Amino) produced YAMAZEN, size: one of S (16×60 mm), M (20×75 mm), L (26×100 mm), 2 L (26×150 mm), and 3 L (46×130 mm); or Presep™ (Luer Lock) NH2(HC) produced by Wako Pure Chemical Industries, Ltd., size: one of type M (14 g/25 mL), type L (34 g/70 mL), type 2 L (50 g/100 mL), and type 3 L (110 g/200 mL)} was used.

As names of the compounds shown below, except for generally used reagents, those shown in the "E-Notebook" Version 12 or 13 (PerkinElmer) were used.

Production Example 1

Synthesis of (5aS,8aR)-4-methyloctahydrocyclopenta[e][1,4]diazine-2,5-dione

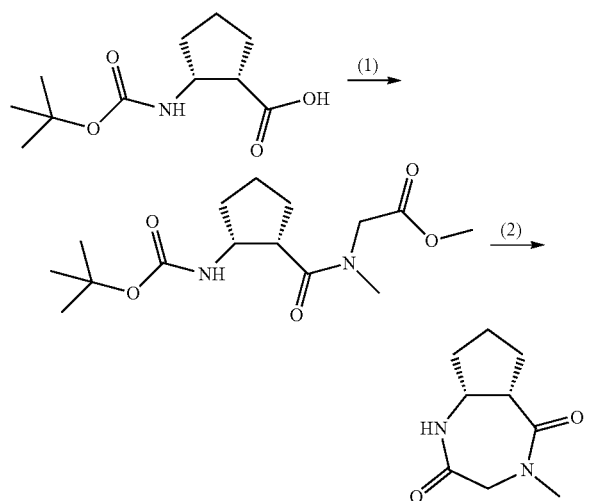

(1) Synthesis of methyl 2-((1S,2R)-2-((t-butoxycarbonyl)amino-N-methylcyclopentanecarboxamide) acetate To a mixture of (1S,2R)-2-((t-butoxycarbonyl)amino)cyclopentane-1-carboxylic acid (CAS No. 137170-89-9) (14.6 g, 63.6 mmol), sarcosine methyl ester hydrochloride (CAS No. 13515-93-0) (10.7 g, 763 mmol) and THF (150 mL) were added TEA (22.2 mL, 159 mmol), HOBT monohydrate (11.7 g, 763 mmol) and EDC (14.6 g, 763 mmol) in that order while cooling on ice. The reaction mixture was stirred at room temperature for 15 hours, and then ethyl acetate and water were added and the organic layer was separated. The aqueous layer was extracted with ethyl acetate. The combined organic layers were washed with an aqueous saturated sodium hydrogencarbonate solution and brine in that order, dried over anhydrous sodium sulfate, filtered and concentrated under reduced pressure. The residue was purified twice by column chromatography (silica gel, 25-30% ethyl acetate/n-heptane) to give the title compound (16.1 g).

MS (ESI) m/z: 337[M+Na]$^+$ (2) Synthesis of (5aS,8aR)-4-methyloctahydrocyclopenta[e][1,4]diazepine-2,5-dione To methyl 2-((1S,2R)-2-((t-butoxycarbonyl)amino)-N-methylcyclopentanecazoxamide)acetate (16.1 g, 513 mmol) was added a 4 N hydrochloric acid/1,4-dioxane solution (160 mL, 640 mmol) while cooling on ice. The reaction mixture was stirred at the same temperature for 30 minutes and then at room temperature for 45 minutes, and then concentrated under reduced pressure. To a methanol solution of the residue (130 ml) was added TBD (8.57 g, 61.6 mmol) while cooling with water. The reaction mixture was stirred for 3 hours while cooling with water, and then cooled to 0° C. The resulting solid was collected by filtration, rinsed 3 times with ice-cooled methanol and then dried under reduced pressure to give the title compound (5.22 g).

$^1$H-NMR (400 MHz, CDCl$_3$) δ(ppm): 1.41-1.59 (m, 2H), 1.78-1.98 (m, 2H), 2.00-2.15 (m, 1H), 2.36-2.53 (m, 1H), 3.08 (s, 3H), 3.18-3.32 (m, 1H), 3.49 (dd, J=15.5, 1.7 Hz, 1H), 3.91-4.04 (m, 1H), 4.51 (d, J=15.4 Hz, 1H), 5.54 (br.s, 1H).

MS (ESI) m/z: 183 [M+H]$^+$

Production Example 2

Synthesis of methyl 2-amino-6-methyl-4,5,6,7-tetrahydrothieno[2,3-c]pyridine-3-carboxylate

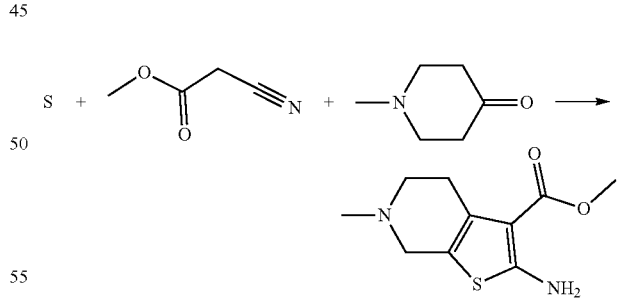

To a mixture of 1-methyl-4-piperidone (CAS No. 1445-73-4) (30.0 mL, 257 mmol), methyl cyanoacetate (CAS No. 105-34-0) (22.6 mL, 257 mmol), sulfur (CAS No. 7704-34-9) (8.25 g, 257 mmol) and methanol (500 mL) was added TEA (35.8 mL, 257 mmol) at room temperature. The reaction mixture was stirred at room temperature for 3 days, and then the precipitate was collected by filtration and rinsed with ethyl acetate. The resulting solid was purified by column chromatography (NH silica gel, ethyl acetate). The concentrated residue was triturated with ethyl acetate. The precipitate was collected by filtration and rinsed with ethyl acetate to give the title compound (38.0 g).

¹H-NMR (400 MHz, CDCl₃) δ(ppm): 2.44 (s, 3H), 2.59-2.71 (m, 2H), 2.77-2.88 (m, 2H), 337 (t, J=2.0 Hz, 2H), 3.79 (s, 3H), 5.94 (br.s, 2H).

MS (ESI) m/z: 227 [M+H]⁺

Production Example 3

Synthesis of (R)-3,3-dimethylhexahydro-1H-pyrrolo[1,2-a][1,4]diazepine-1,5(2H)-dione

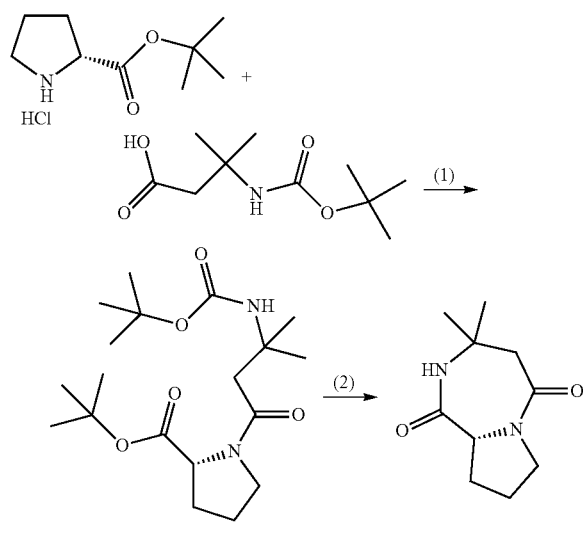

(1) Synthesis of (R)-t-butyl 1-(3-((t-butoxycarbonyl)amino)-3-methylbutanoyl)pyrrolidine-2-carboxylate To a mixture of 3-(t-butoxycarbonylamino)-3-methylbutanoic acid (CAS No. 129765-95-3) (1.5 g, 6.90 mmol), D-proline t-butyl ester hydrochloride (CAS No. 184719-80-0) (1.43 g, 6.90 mmol), TEA (3.85 mL, 27.6 mmol) and THF (15.0 mL) was added 1-propanephosphonic anhydride (cyclic trimer) (50% ethyl acetate solution, approximately 1.7 mol/L) (6.09 mL, 10.4 mmol), at 0° C. The reaction mixture was stirred at room temperature for 2 days. Ethyl acetate and water were added to the reaction mixture and the organic layer was separated. The organic layer was washed with an aqueous saturated ammonium chloride solution, water, an aqueous saturated sodium hydrogencarbonate solution, water and brine in that order, and then dried over anhydrous magnesium sulfate and filtered. The filtrate was concentrated under reduced pressure to give the title compound (2.67 g).

MS (ESI) m/z: 371 [M+H]⁺

(2) Synthesis of (R)-3,3-dimethylhexahydro-1H-pyrrolo[1,2-a][1,4]diazepine-1,5(2H)-dione To a mixture of (R)-t-butyl 1-(3-((t-butoxycarbonyl)amino)-3-methylbutanoyl)pyrrolidine-2-carboxylate (2.67 g) and 1,4-dioxane (10.0 mL) was added a 4 N hydrochloric acid/1,4-dioxane solution (20 mL, 80 mmol) at 0° C. After stirring overnight at room temperature, the reaction mixture was concentrated under reduced pressure. To a mixture of the residue, TEA (3.01 mL, 21.6 mmol), THF (30.0 mL) and DMF (30.0 mL) was added 1-propanephosphonic anhydride (cyclic trimer) (50% ethyl acetate solution, approximately 1.7 mol/L) (636 mL, 10.8 mmol), at 0° C. The reaction mixture was stirred overnight at room temperature. The reaction mixture was poured into water, ethyl acetate was added, and the organic layer was separated. The aqueous layer was extracted with 10% methanol/chloroform. The combined organic layers were dried over anhydrous magnesium sulfate and filtered, and the filtrate was concentrated under reduced pressure. The resulting residue was purified by column chromatography (silica gel, 0-50% methanol/ethyl acetate) to give the title compound (896 mg).

¹H-NMR (400 MHz, CDCl₃) δ(ppm): 1.34 (s, 3H), 1.36 (s, 3H), 1.77-1.93 (m, 2H), 2.10-2.24 (m, 1H), 2.48 (dd, J=14.1, 1.6 Hz, 1H), 2.60-2.73 (m, 1H), 3.08 (d, J=14.5 Hz, 1H), 3.44-3.55 (m, 1H), 3.63 (dt, J=11.6, 7.3 Hz, 1H), 4.43 (dd, J=7.8, 4.7 Hz, 1H), 5.56 (br.s, 1H).

MS (ESI) m/z: 197 [M+H]⁺

Production Example 4

Synthesis of ethyl 3-amino-6-fluorobenzofuran-2-carboxylate

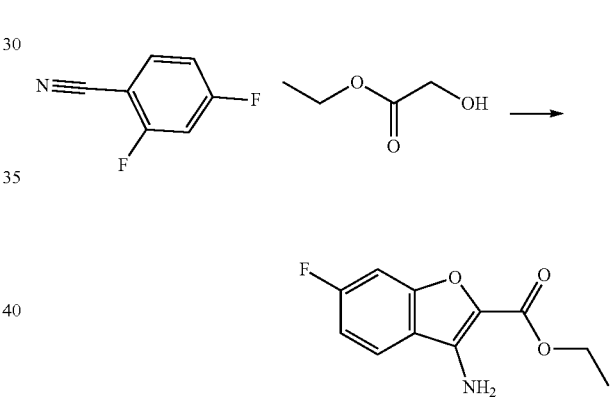

To a mixture of ethyl glycolate (CAS No. 623-50-7) (0.408 mL, 431 mmol) and 1,4-dioxane (8 mL) were added potassium t-butoxide (460 mg, 4.10 mmol) and 2,4-difluorobenzonitrile (CAS No. 3939-09-1) (300 mg, 2.16 mmol) in that order at 0° C. The reaction mixture was stirred at room temperature for 2 days. An aqueous saturated ammonium chloride solution and ethyl acetate were added to the reaction mixture, and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 30-40% ethyl acetate % n-heptane) to give the title compound (359 mg).

¹H-NMR (400 MHz, CDCl₃) δ(ppm): 1.34-1.47 (m, 3H), 4.43 (q, J=7.0 Hz, 2H), 4.83-5.11 (m, 2H), 6.93-7.06 (m, 1H), 7.10-7.19 (m, 1H), 7.42-7.56 (m, 1H)

MS (ESI) m/z: 224 [M+H]⁺

Production Example 5

Synthesis of ethyl 3-amino-4,6-dimethylfuro[2,3-b]pyridine-2-carboxylate

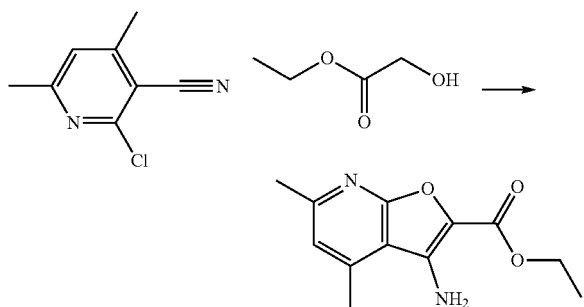

To a mixture of ethyl glycolate (CAS No. 623-50-7) (0200 mL, 2.11 mmol) and THF (4 mL) were added potassium t-butoxide (356 mg, 3.17 mmol) and 2-chloro-4,6-dimethylnicotinonitrile (CAS No. 14237-71-9) (300 mg, 1.80 mmol) in that order, at room temperature. The reaction mixture was stirred at room temperature for 1 hour. An aqueous saturated ammonium chloride solution, water and ethyl acetate were added to the reaction mixture, and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 60-70% ethyl acetate/n-heptane) to give the title compound (180 mg).

$^1$H-NMR (400 MHz, CDCl$_3$) δ(ppm): 134-1.41 (m, 3H), 2.56 (s, 3H), 2.63 (s, 3H), 438 (q, J=7.6 Hz, 2H), 4.97-5.20 (m, 2H), 6.83 (s, 1H)

MS (ESI) m/z: 235 [M+H]$^+$

Production Example 6

Synthesis of (5aR,8aR)-4-methyloctahydrocyclopenta[e][1,4]diazepine-2,5-dione

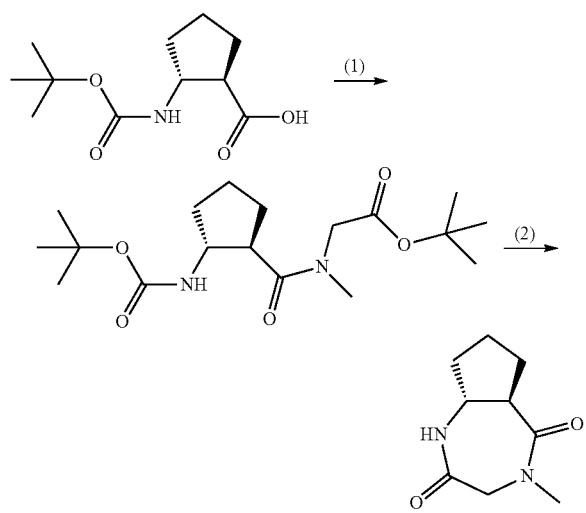

(1) Synthesis of t-butyl 2-((1R,2R)-2-((t-butoxycarbonyl)amino)-N-methylcyclopentanecarboxamide)acetate To a mixture of (1R,2R)-t-butoxycarbonyl-2-aminocyclopentanecarboxylic acid (CAS No. 245115-25-7) (1.00 g, 436 mmol), sarcosine t-butyl ester hydrochloride (CAS No. 136088-69-2) (872 mg, 4.80 mmol) and DCM (10 mL) were added DIPEA (1.81 mL, 10.5 mmol) and HATU (1.99 g, 5.23 mmol) in that order at room temperature. After stirring at room temperature for 1 hour, the reaction mixture was directly purified by column chromatography (silica gel, 30-50% ethyl acetate/n-heptane) to give the title compound (1.61 g).

MS (ESI) m/z: 357 [M+H]$^+$

(2) Synthesis of (5aR,8aR)-4-methyloctahydrocyclopenta[e][1,4]diazepine-2,5-dione To t-butyl 2-((1R,2R)-2-((t-butoxycarbonyl)amino)-N-methylcyclopentanecarboxamide)acetate (1.61 g, 4.52 mmol) was added a 4 N hydrochloric acid/1,4-dioxane solution (16 mL, 64 mmol) at room temperature, and the mixture was stirred for 20 hours. The reaction mixture was concentrated under reduced pressure. After adding sodium hydrogencarbonate (0.911 g, 10.8 mmol), methanol (24 mL), NMM (0.099 mL, 0.90 mmol) and DMT-MM (123% H$_2$O, 1.80 g, 5.70 mmol) in that order to the residue at room temperature, the mixture was stirred for 20 hours. The reaction mixture was concentrated under reduced pressure and the residue was rinsed with DCM. The rinsed solution was concentrated under reduced pressure and the residue was purified by column chromatography (silica gel, 5-20% methanol/ethyl acetate) to give the title compound (745 mg).

$^1$H-NMR (400 MHz, CDCl$_3$) δ(ppm): 1.56-1.88 (m, 3H), 1.91-2.02 (m, 1H), 2.13-2.23 (m, 1H), 2.26-239 (m, 1H), 3.07 (s, 3H), 3.08-3.16 (m, 1H), 3.51-3.62 (m, 1H), 3.79 (d, J=18.0 Hz, 1H), 4.58 (d, J=18.0 Hz, 1H), 6.76 (br.s, 1H).

MS (ESI) m/z: 183 [M+H]$^+$

Production Example 7

Synthesis of ethyl 3-amino-6-(trifluoromethyl)benzofuran-2-carboxylate

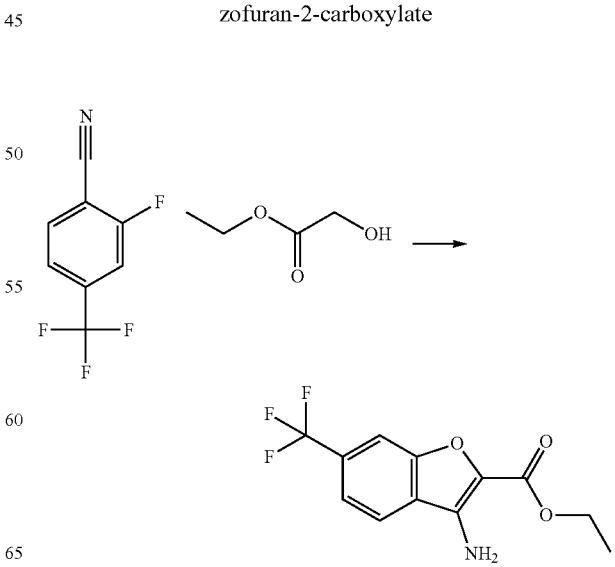

To a mixture of ethyl glycolate (CAS No. 623-50-7) (0.150 mL, 1.59 mmol) and THF (6 mL) were added potassium t-butoxide (267 mg, 2.38 mmol) and 2-fluoro-4-(trifluoromethyl)benzonitrile (CAS No. 146070-34-0) (0.242 mL, 1.74 mmol) in that order at room temperature. The reaction mixture was stirred overnight at room temperature. An aqueous saturated ammonium chloride solution, water and ethyl acetate were added to the reaction mixture, and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 30% ethyl acetate/n-heptane) to give the title compound (100 mg).

$^1$H-NMR (400 MHz, CDCl$_3$) δ(ppm): 1.44 (t, J=7.0 Hz, 3H), 4.32-4.57 (m, 2H), 4.83-5.21 (m, 2H), 7.43-7.57 (m, 1H), 7.59-7.81 (m, 2H)

MS (ESI) m/z: 274 [M+H]$^+$

Production Example 8

Synthesis of ethyl 2-amino-6-(2,2-difluoroethyl)-5,6,7-tetrahydrothieno[2,3-c]pyridine-3-carboxylate

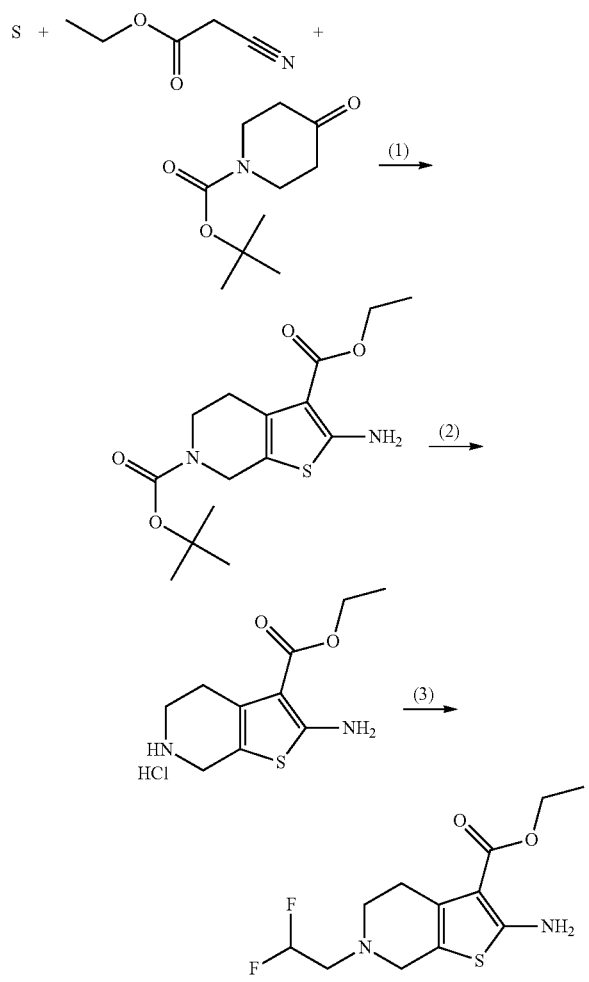

(1) Synthesis of 6-t-butyl 3-ethyl 2-amino-4,5-dihydrothieno[2,3-c]pyridine-3,6(7H)-dicarboxylate To a mixture of 1-(t-butoxycarbonyl)-4-piperidone (CAS No. 79099-07-3) (45.1 g, 226 mmol), ethyl cyanoacetate (CAS No. 105-56-6) (25.6 g, 226 mmol), sulfur (CAS No. 7704-34-9) (7.26 g, 226 mmol) and ethanol (450 mL) was added TEA (31.6 mL, 226 mmol) at room temperature. After stirring the reaction mixture at 80° C. for 4 hours and 15 minutes, it was cooled to room temperature. The precipitate was collected by filtration and rinsed with ethanol. The resulting solid was dissolved in ethanol (350 mL) at 80° C. and cooled to room temperature. The precipitate was collected by filtration and rinsed with ethanol. The resulting solid was dried under reduced pressure to give the title compound (56.0 g).

$^1$H-NMR (400 MHz, CDCl$_3$) δ(ppm): 1.34 (t, J=7.2 Hz, 3H), 1.48 (s, 9H), 2.80 (br.s, 2H), 3.61 (t, J=5.9 Hz, 2), 4.26 (q, J=7.0 Hz, 2H), 435 (br.s, 2H), 6.00 (br.s, 2H).

MS (ESI) m/z: 327 [M+H]$^+$ (2) Synthesis of ethyl 2-amino-4,5,6,7-tetrahydrothieno[2,3-c]pyridine-3-carboxylate Hydrochloride To a mixture of 6-t-butyl 3-ethyl 2-amino-4,5-dihydrothieno[2,3-c]pyridine-3,6(7H)-dicarboxylate (3.34 g, 10.2 mmol) and 1,4-dioxane (33 mL) was added 5 N hydrochloric acid (4.00 mL, 20.0 mmol). After stirring the reaction mixture for 15 minutes at 80° C. it was cooled to room temperature. The precipitate was filtered and rinsed with 1,4-dioxane and ethyl acetate in that order. The resulting solid was dried under reduced pressure to give the title compound (2.05 g).

$^1$H-NMR (400 MHz, DMSO-d6) δ(ppm): 1.25 (t, J=7.0 Hz, 3H), 2.88 (t, J=6.1 Hz, 2H), 3.28 (t, J=6.1 Hz, 2H), 4.02 (s, 2H), 4.18 (q, J=7.0 Hz, 2H), 7.46 (s, 2H), 935 (br.s, 2H)

MS (ESI) m/z: 227 [M+H]$^+$ (3) Synthesis of ethyl 2-amino-6-(2,2-difluoroethyl)-4,5,6,7-tetrahydrothieno[2,3-c]pyridine-3-carboxylate To a mixture of ethyl 2-amino-4,5,6,7-tetrahydrothieno[2,3-c]pyridine-3-carboxylate hydrochloride (53.0 mg, 0.202 mmol), 1,1-difluoro-2-iodoethane (CAS No. 598-39-0) (0.025 mL, 0.282 mmol) and DMF (0.700 mL) was added potassium carbonate (84.0 mg, 0.605 mmol) at room temperature. The reaction mixture was stirred at 50° C. for 3 hours and then at 80° C. for 16 hours. After restoring the reaction mixture to room temperature, it was purified by column chromatography (NH silica gel, 10-50%/o, ethyl acetate/heptane) to give the title compound (40.0 mg).

$^1$H-NMR (400 MHz, CDCl$_3$) δ(ppm): 1.24-1.37 (m, 3H), 2.74-2.96 (m, 6H), 3.49-3.68 (m, 2H), 4.17-4.34 (m, 2H), 5.74-6.17 (m, 3H).

MS (ESI) m/z: 291 [M+H]$^+$

Production Example 9

Synthesis of ethyl 2-amino-6-(2-methoxyethyl)-45,67-tetrahydrothien[2,3-c]pyridine-3-carboxylate

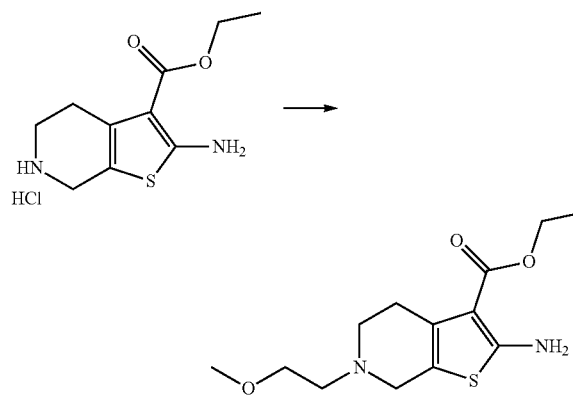

To a mixture of ethyl 2-amino-4,5,6,7-tetrahydrothieno[2,3-c]pyridine-3-carboxylate hydrochloride obtained in Production Example 8(2) (53.0 mg, 0.202 mmol), potassium carbonate (84.0 mg, 0.605 mmol) and DMF (0.700 mL) was added 1-iodo-2-methoxyethane (CAS No. 4296-15-5) (52.5 mg, 0.282 mmol) at room temperature. The reaction mixture was stirred at 50° C. for 3 hours. After restoring the reaction mixture to room temperature, it was purified by column chromatography (NH silica gel, 10-50%, ethyl acetate/heptane) to give the title compound (34.8 mg).

$^1$H-NMR (400 MHz, CDCl$_3$) δ(ppm): 1.30-1.36 (m, 3H), 2.73-2.84 (m, 6H), 3.38 (s, 3H), 3.51 (br.d, J=1.8 Hz, 2H), 3.54-3.61 (m, 2H), 4.21-4.32 (m, 2H), 5.94 (br.s, 2H).

MS (ESI) m/z: 285 [M+H]$^+$

Production Example 10

Synthesis of ethyl 3-amino-6-(difluoromethyl)benzofuran-2-carboxylate

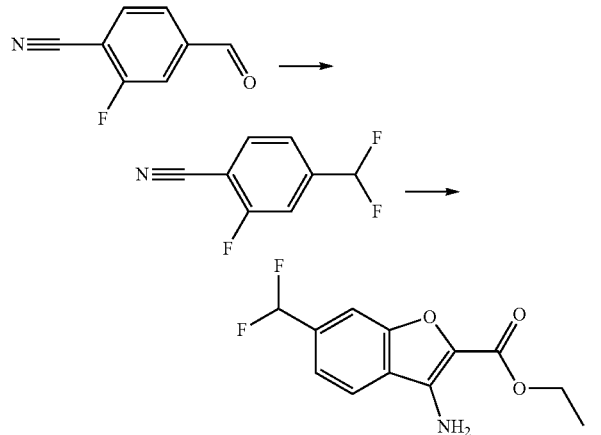

To a mixture of 2-fluoro-4-formylbenzonitrile (CAS No. 101048-76-4) (300 mg, 2.01 mmol) and DCM (9 mL) were added DAST (0395 mL, 3.02 mmol) and one drop of ethanol in that order at room temperature. The reaction mixture was stirred overnight at room temperature. Water and ethyl acetate were added to the reaction mixture and the organic layer was separated. The aqueous layer was extracted again with ethyl acetate. The combined organic layers were dried over anhydrous sodium sulfate and filtered, and the filtrate was concentrated under reduced pressure. To a mixture of the residue (344 mg), DMSO (6 mL) and ethyl glycolate (CAS No. 623-50-7) (0381 mL, 4.02 mmol) was added potassium t-butoxide (429 mg, 3.82 mmol) at room temperature. The reaction mixture was stirred overnight at room temperature. An aqueous saturated ammonium chloride solution, water and ethyl acetate were added to the reaction mixture, and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 40% ethyl acetate/n-heptane) to give the title compound (256 mg).

$^1$H-NMR (400 MHz, CDCl$_3$) δ(ppm): 1.44 (t, J=73 Hz, 3H), 4.34-4.55 (m, 2H), 4.80-5.11 (m, 2H), 6.74 (t, J=56.6 Hz, 1H), 7.35-7.45 (m, 1H), 7.57-7.71 (m, 2H)

MS (ESI) m/z: 256 [M+H]$^+$

Production Example 11

Synthesis of (8R,9aS)-8-fluoro-3,3-dimethylhexahydro-1H-pyrrolo[1,2-a][1,4]diazepine-1,5(2H)-dione

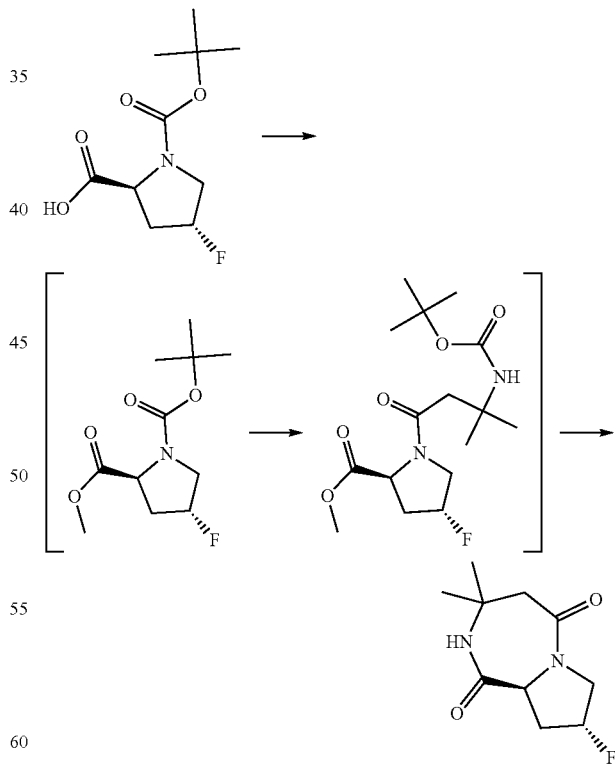

To a mixture of (2S,4R)-1-(t-butoxycarbonyl)-4-fluoropyrrolidine-2-carboxylic acid (CAS No. 203866-14-2) (5.00 g, 21.4 mmol) in DMF (25.0 mL) were added potassium carbonate (4.44 g, 32.2 mmol) and iodomethane (CAS No. 74-88-4) (2.68 mL, 42.9 mmol). The reaction mixture was stirred at room temperature for 3 hours. The reaction mixture was crudely purified by column chromatography (NH silica gel, 20-40% ethyl acetate/n-heptane). To the obtained crude product (5.50 g) was added a 4 N hydrochloric acid/1,4-dioxane solution (55.0 mL, 220 mmol) at room temperature. After stirring for 1 hour at the same temperature, the reaction mixture was concentrated under reduced pressure. To a mixture of the concentrated residue, THF (55.0 ml), 3-(t-butoxycarbonylamino)-3-methylbutanoic acid (CAS No. 129765-95-3) (4.83 g, 22.2 mmol) and TEA (930 mL, 66.7 mmol) was added 1-propenephosphonic anhydride (cyclic trimer) (50% ethyl acetate solution, approximately 1.6 mol/L) (20.9 mL, 33.4 mmol) at room temperature. The reaction mixture was stirred overnight at room temperature, and then ethyl acetate and water were added and the organic layer was separated. The organic layer was dried over anhydrous magnesium sulfate and filtered, and the filtrate was concentrated under reduced pressure. To a mixture of the resulting residue (5.50 g) and methanol (32.1 mL) was added an aqueous solution of 1 N sodium hydroxide (31.8 mL, 31.8 mmol). After stirring the reaction mixture at room temperature for 3 hours, hydrochloric acid was added to make the reaction mixture acidic. After then adding ethyl acetate and separating off the organic layer, it was dried over anhydrous magnesium sulfate and filtered, and the filtrate was concentrated under reduced pressure. To the resulting residue was added a 4 N hydrochloric acid/1,4-dioxane solution (39.7 mL, 159 mmol) at room temperature. After stirring for 3 hours at the same temperature, the reaction mixture was concentrated under reduced pressure. To a THF (8 ml) solution of the residue were added TEA (6.64 mL, 47.6 mmol) and 1-propanephosphonic anhydride (cyclic trimer) (50% ethyl acetate solution, approximately 1.6 mol/L) (14.9 mL, 23.8 mmol). The reaction mixture was stirred for 3 days at 60° C. and then concentrated under reduced pressure. The resulting residue was purified by column chromatography (silica gel, 5-25% methanol/ethyl acetate) to give the title compound (950 mg).

$^1$H-NMR (400 MHz, CDCl$_3$) δ(ppm): 1.24-1.42 (m, 6H), 2.42-2.77 (m, 3H), 2.97-3.17 (m, 1H), 330-3.53 (m, 1H), 4.09-436 (m, 1H), 4.58-4.75 (m, 1H), 5.03-532 (m, 1H), 6.17 (br.s, 1H).

MS (ESI) m/z: 215 [M+H]$^+$

Production Example 12

Synthesis of (5aSR,8aRS)-4-methylhexahydro-1H-furo[3,4-e][1,4]diazepine-2,5-dione

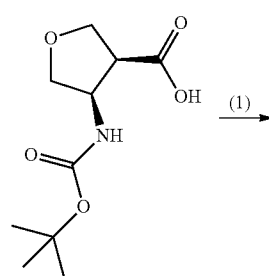

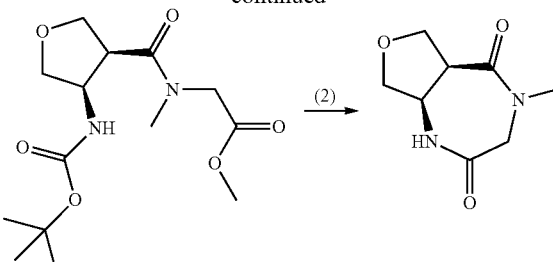

(1) Synthesis of methyl 2-((3SR,4RS)-4-((t-butoxycarbonyl)amino)-N-methyltetrahydrofuran-3-carboxamide)acetate To a mixture of cis-4-t-butoxycarbonylamino-tetrahydrofuran-3-carboxylic acid (CAS No. 1414958-20-5) (500 mg, 2.16 mmol), methyl 2-(methylamino)acetate hydrochloride (362 mg, 2.60 mmol) and DCM (5 mL) were added DIPEA (127 mL, 735 mmol) and HATU (987 mg, 2.60 mmol) in that order at room temperature. The reaction mixture was stirred at room temperature for 1 hour. The reaction mixture was directly purified by column chromatography (silica gel, 40-100%, ethyl acetate/n-heptane) to give the title compound (649 mg).

MS (ESI) m/z: 317 [M+H]$^+$ (2) Synthesis of (5aSR,8aRS)-4-methylhexahydro-1H-furo[3,4-e][1,4]diazepine-2,5-dione To methyl 2-((3SR,4RS)-4-((t-butoxycarbonyl)amino)-N-methyltetrahydrofuran-3-carboxamide)acetate (649 mg, 2.05 mmol) was added a 4 N hydrochloric acid/1,4-dioxane solution (7 mL) at room temperature. The reaction mixture was stirred at room temperature for 3 hours, and then concentrated under reduced pressure. To the residue were added THF (7 mL) and TBD (343 mg, 2.46 mmol) at room temperature. After the reaction mixture was subjected to ultrasonication, it was stirred at room temperature for 1 hour. Acetic acid (0.2 mL) was then added to the reaction mixture, and it was concentrated under reduced pressure. The residue was purified by column chromatography (silica gel, 1040% methanol/ethyl acetate) to give the title compound (178 mg).

$^1$H-NMR (400 MHz, CDCl$_3$) δ(ppm): 3.07 (s, 3H), 3.43 (q, J=8.1 Hz, 1H), 3.51-3.63 (m, 2H), 4.10-432 (m, 3H), 438 (dd, J=9.6, 7.2 Hz, 1H), 4.48 (d, J=14.8 Hz, 1H), 5.54 (br s, 1H).

MS (ESI) m/z: 185 [M+H]$^+$

Production Example 13

Synthesis of ethyl 3-amino-6-(trifluoromethyl)benzofuran-2-carboxylate

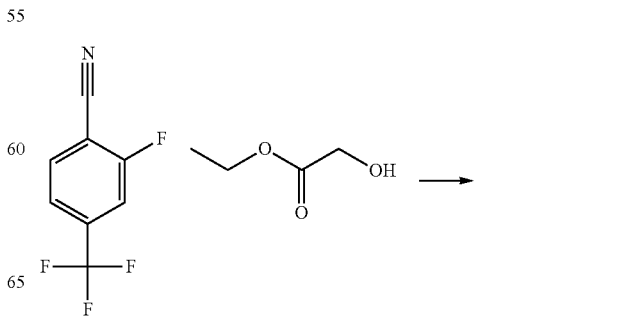

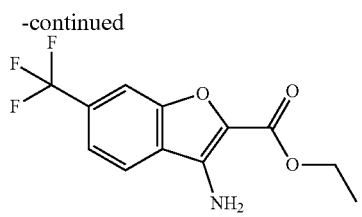

To a mixture of ethyl glycolate (CAS No. 623-50-7) (1.02 mL, 10.8 mmol) and DMSO (10 mL) were added potassium t-butoxide (1.13 g, 10.1 mmol) and 2-fluor-4-(trifluoromethyl)benzonitrile (CAS No. 146070-34-0) (1.00 mL, 7.19 mmol) in that order at room temperature. The reaction mixture was stirred at room temperature for 8 hours. An aqueous saturated ammonium chloride solution, water and ethyl acetate were added to the reaction mixture, and the organic layer was separated. The aqueous layer was extracted with ethyl acetate, the combined organic layers were dried over anhydrous sodium sulfate and filtered, and the filtrate was concentrated under reduced pressure. The residue was purified by column chromatography (silica gel, 30% ethyl acetate/n-heptane) to give the title compound (949 mg).

$^1$H-NMR (400 MHz, CDCl$_3$) δ(ppm): 1.40-1.48 (m, 3H), 4.45 (q, J=73 Hz, 2H), 4.98 (br.s, 2H), 7.44-7.54 (m, 1H), 7.61-7.78 (m, 2H)

MS (ESI) m/z: 274 [M+H]$^+$

Production Example 14

Synthesis of (5aS,8aS)-4-methyloctahydrocyclopenta[e][1,4]diazepine-2,5-dione

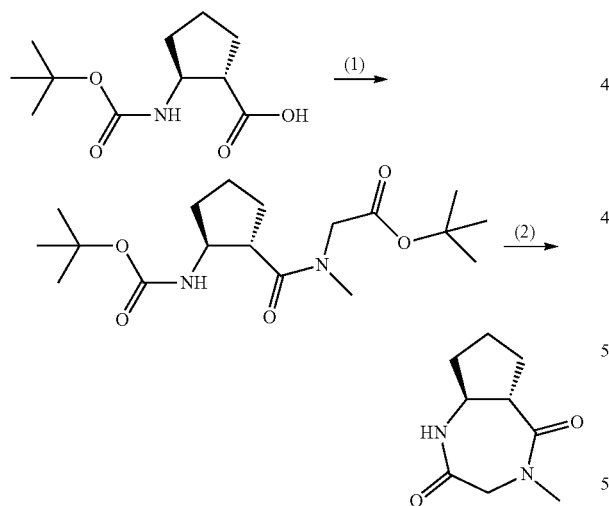

(1) Synthesis of t-butyl 2-((1S,2S)-2-((t-butoxycarbonyl)amino)-N-methylcyclopentanecarboxamide)acetate To a mixture of (1S,2S)-2-(t-butoxycarbonylamino)cyclopentanecarboxylic acid (CAS No. 143679-80-5) (1.00 g, 436 mmol), sarcosine t-butyl ester hydrochloride (872 mg, 4.80 mmol), DIPEA (1.81 mL, 10.5 mmol) and DCM (10 mL) was added HATU (1.99 g, 5.23 mmol) at room temperature. After stirring the reaction mixture overnight at room temperature, it was directly purified by column chromatography (silica gel, 30-50% ethyl acetate/n-heptane) to give the title compound (1.55 g).

MS (ESI) m/z: 357 [M+H]$^+$ (2) Synthesis of (5aS,8aS)-4-methyloctahydrocyclopenta[e][1,4]diazepine-2,5-dione To t-butyl 2-((1S,2S)-2-((t-butoxycarbonyl)amino)-N-methylcyclopentanecarboxamide)acetate (1.55 g, 435 mmol) was added a 4 N hydrochloric acid/1,4-dioxane solution (16 mL, 64 mmol) at room temperature, and the mixture was stirred for 16 hours. The reaction mixture was concentrated under reduced pressure. To the residue were added sodium hydrogencarbonate (0.877 g, 10.4 mmol), methanol (24 mL), NMM (0.096 mL, 0.87 mmol) and DMT-MM (123% H$_2$O, 1.73 g, 5.48 mmol) in that order at room temperature, and the mixture was stirred for 3 hours. The reaction mixture was concentrated under reduced pressure and the residue was rinsed with DCM. The rinsed solution was concentrated under reduced pressure and the residue was purified by column chromatography (silica gel, 0-20% methanol/ethyl acetate) to give the title compound (753 mg).

$^1$H-NMR (400 MHz, CDCl$_3$) δ(ppm): 1.55-1.88 (m, 3H), 1.91-2.02 (m, 1H), 2.11-2.22 (m, 1H), 2.25-2.40 (m, 1H), 3.07 (s, 3H), 3.07-3.16 (m, 1H), 3.51-3.62 (m, 1H), 3.78 (d, J=18.0 Hz, 1H), 4.57 (d, J=18.0 Hz, 1H), 6.54 (br.s, 1H).

MS (ESI) m/z: 183 [M+H]$^+$

Production Example 15

Synthesis of (S)-3,3-dimethylhexahydro-1H-pyrrolo[1,2-a][1,4]diazepine-1,5(2H)-dione

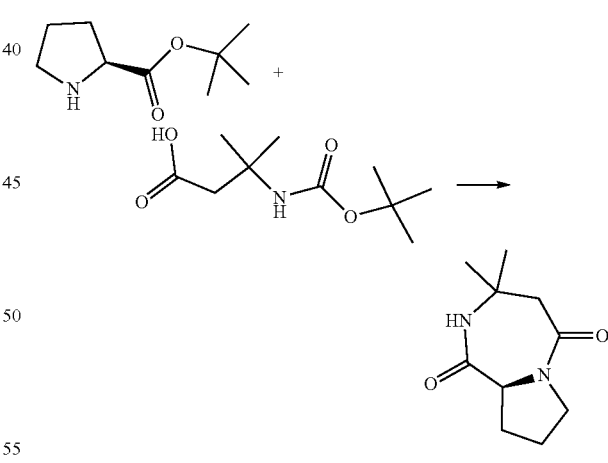

To a mixture of 3-(t-butoxycarbonylamino)-3-methylbutanoic acid (CAS No. 129765-95-3) (2.0 g, 9.21 mmol), L-proline t-butyl ester (CAS No. 2812-46-6) (1.58 g, 9.21 mmol), TEA (3.85 mL, 27.6 mmol) and THF (15.0 mL) was added 1-propanephosphonic anhydride (cyclic trimer) (50% ethyl acetate solution, approximately 1.7 mol/L) (8.12 mL, 13.8 mmol), at 0° C. The reaction mixture was stirred at room temperature for 3 days. Ethyl acetate and water were then added and the organic layer was separated. The organic layer was washed with an aqueous saturated ammonium chloride solution, water, an aqueous saturated sodium hydrogencarbonate solution, water and brine in that order, and then dried over anhydrous magnesium sulfate and filtered. The filtrate was concentrated under reduced pressure. To a mixture of the resulting residue (3.03 g) and 1,4-dioxane (10.0 mL) was added a 4 N hydrochloric acid/1,4-dioxane solution (20 mL, 80 mmol) at 0° C. After stirring overnight at room temperature, the reaction mixture was concentrated under reduced pressure. To a mixture of the residue, TEA (3.42 mL, 24.5 mmol), THF (50.0 mL) and DMF (30.0 mL) was added 1-propanephosphonic anhydride (cyclic trimer) (50% ethyl acetate solution, approximately 1.7 mol/L) (7.22 mL, 123 mmol), at 0° C. The reaction mixture was stirred at room temperature for 2 days and then poured into ice water, after which ethyl acetate was added and the organic layer was separated. The aqueous layer was extracted with chloroform and 10% methanol/chloroform. The combined organic layers were dried over anhydrous magnesium sulfate and filtered, and the filtrate was concentrated under reduced pressure. The resulting residue was purified by column chromatography (silica gel, 0-50% methanol/ethyl acetate) to give the title compound (942 mg).

$^1$H-NMR (400 MHz, CDCl$_3$) δ(ppm): 1.34 (s, 3H), 1.36 (s, 3H), 1.76-1.93 (m, 2H), 2.09-2.25 (m, 1H), 2.48 (dd, J=14.3, 1.8 Hz, 1H), 2.61-2.74 (m, 1H), 3.08 (d, J=14.1 Hz, 1H), 3.45-3.56 (m, 1H), 3.57-3.71 (m, 1H), 4.43 (dd, J=8.0, 4.9 Hz, 1H), 5.54 (br.s, 1H).

Production Example 16

Synthesis of methyl 3-amino-5-methyl-4,5,6,7-tetrahydrothieno[3,2-c]pyridine-2-carboxylate

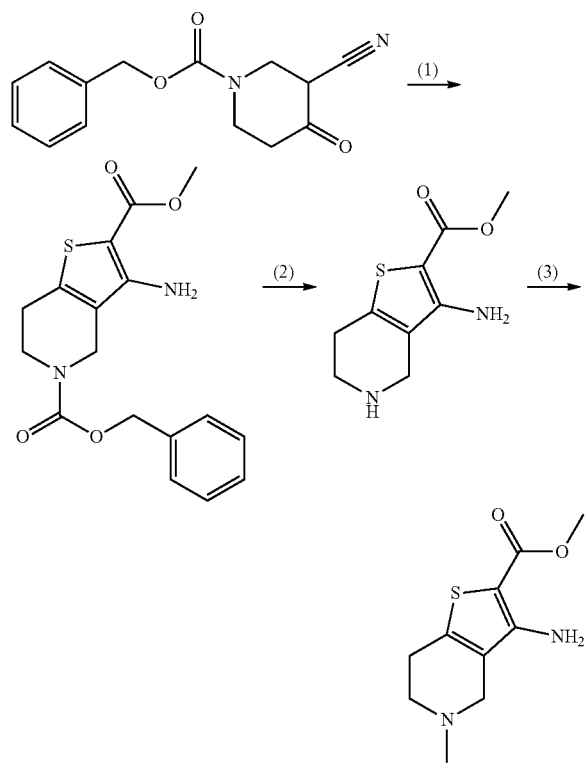

(1) Synthesis of 5-benzyl 2-methyl 3-amino-6,7-dihydrothieno[3,2-c]pyridine 2,5(4H)-dicarboxylate A reaction mixture of benzyl 3-cyano-4-oxopiperidine-1-carboxylate (CAS No. 916423-53-5) (868 mg, 336 mmol), TEA (0.937 mL, 6.72 mmol), 4-dimethylaminopyridine (41.1 mg, 0336 mmol), methanesulfonyl chloride (0312 mL, 4.03 mmol) and DCM (10 mL) was stirred at room temperature for 16 hours. Water was added to the reaction mixture, and the organic layer was separated. The aqueous layer was extracted with DCM. The combined organic layers were dried over anhydrous magnesium sulfate and filtered, and the filtrate was concentrated under reduced pressure to give a reaction residue (1.13 g). To a mixture of 60% sodium hydride (537 mg) and THF (20 mL) was slowly added dropwise methyl thioglycolate (CAS No. 2365-48-2) (1.05 mL, 11.8 mmol) at 0° C. under a nitrogen atmosphere, and the mixture was restored to room temperature and further stirred for 30 minutes. The reaction mixture was again cooled with an ice water bath, and a mixture of the reaction residue (1.13 g) and THF (10 mL) was added thereto and stirring was continued for 1 hour. The reaction mixture was restored to room temperature and further stirred for 17.5 hours.

To the reaction mixture were added water and ethyl acetate, and the organic layer was separated. The organic layer was washed with water and then dried over anhydrous magnesium sulfate and filtered, and the filtrate was concentrated under reduced pressure. The residue was purified by column chromatography (silica gel, 1-33% ethyl acetate/n-heptane) to give the title compound (813 mg).

$^1$H-NMR (400 MHz, CDCl$_3$) δ(ppm): 2.78 (br.s, 2H), 3.74-3.83 (m, 5H), 432 (br.d, J=9.4 Hz, 2H), 5.11-5.23 (m, 2H), 5.33 (br.d, J=9.4 Hz, 2H), 730-7.43 (m, 5H).

MS (ESI) m/z: 347 [M+H]$^+$ (2) Synthesis of methyl 3-amino-4,5,6,7-tetrahydrothieno[3,2-c]pyridine-2-carboxylate A mixture of 5-benzyl 2-methyl 3-amino-6,7-dihydrothieno[3,2-c]pyridine-2,5(4H)-dicarboxylate (200 mg, 0.577 mmol), 10% palladium-carbon (493% wet) (20 mg) and methanol (3 mL) was stirred at room temperature for 1 hour in a hydrogen gas atmosphere. The reaction mixture was filtered with Celite™ and the filtrate was concentrated under reduced pressure. To the resulting residue were added 10%/palladium-carbon (493% wet) (200 mg) and methanol (10 mL), and the mixture was stirred for 21.5 hours at room temperature in a hydrogen gas atmosphere. The reaction mixture was filtered with Celite™ and the filtrate was concentrated under reduced pressure to give the title compound (94.6 mg).

$^1$H-NMR (400 MHz, CDCl$_3$) δ(ppm): 2.62-2.78 (m, 2H), 3.13 (t, J=5.7 Hz, 2H), 3.61-3.72 (m, 2H), 3.76-3.88 (m, 3H), 5.29 (br.s, 2H).

MS (ESI) m/z: 213 [M+H]$^+$ (3) Synthesis of methyl 3-amino-5-methyl-4,5,6,7-tetrahydrothieno[3,2-c]pyridine-2-carboxylate To a mixture of methyl 3-amino-4,5,6,7-tetrahydrothieno[3,2-c]pyridine-2-carboxylate (94 mg, 0.443 mmol), THF (4 mL) and methanol (4 mL) was added a 35-38% formaldehyde solution (0.036 mL) at room temperature, and the mixture was stirred for 50 minutes. Sodium triacetoxyborohydride (188 mg, 0.886 mmol) was added and stirring was continued at room temperature for 26 hours.

Saturated sodium bicarbonate water and ethyl acetate were added to the reaction mixture, and the organic layer was separated. The organic layer was concentrated under reduced pressure. The residue was purified by column chromatography (NH silica gel, 5-45%, ethyl acetate/n-heptane) to give the title compound (75 mg).

$^1$H-NMR (400 MHz, CDCl$_3$) δ(ppm): 2.44-2.55 (m, 3H), 2.68-2.77 (m, 2H), 2.79-2.89 (m, 2H), 3.19-3.31 (m, 2H), 3.68-3.87 (m, 3H), 5.17-5.41 (m, 2H).

MS (ESI) m/z: 227 [M+H]$^+$

Production Example 17

Synthesis of (5aRS,8aSR)-t-butyl 4-methyl-2,5-dioxooctahydropyrrolo[3,4-e][1,4]diazepine-7(1H)-carboxylate (trans-form) and (5aSR,8aSR)-t-butyl 4-methyl-2,5-dioxooctahydropyrrolo[3,4-e][1,4]diazepine-7(1H)-carboxylate (cis-form)

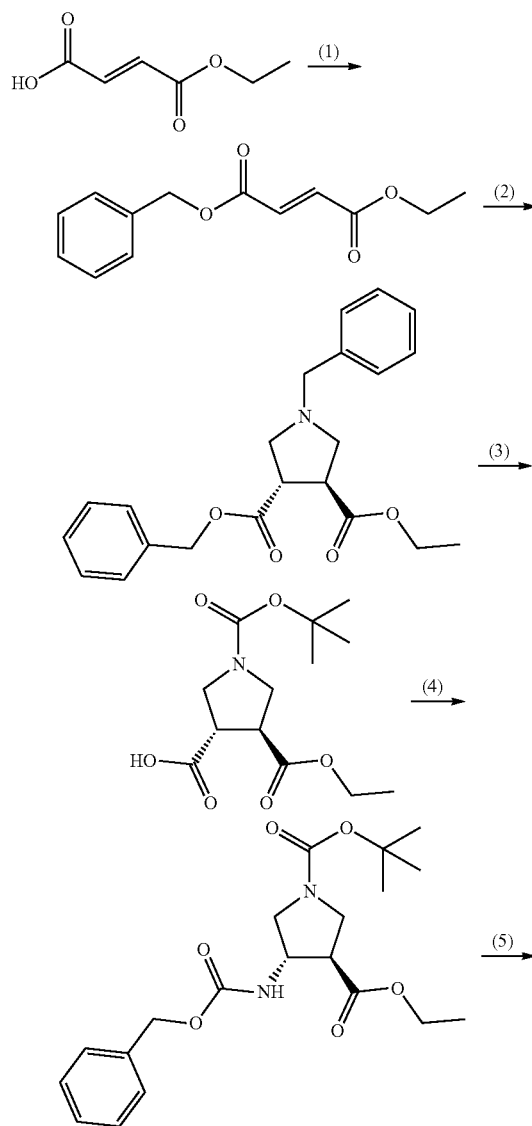

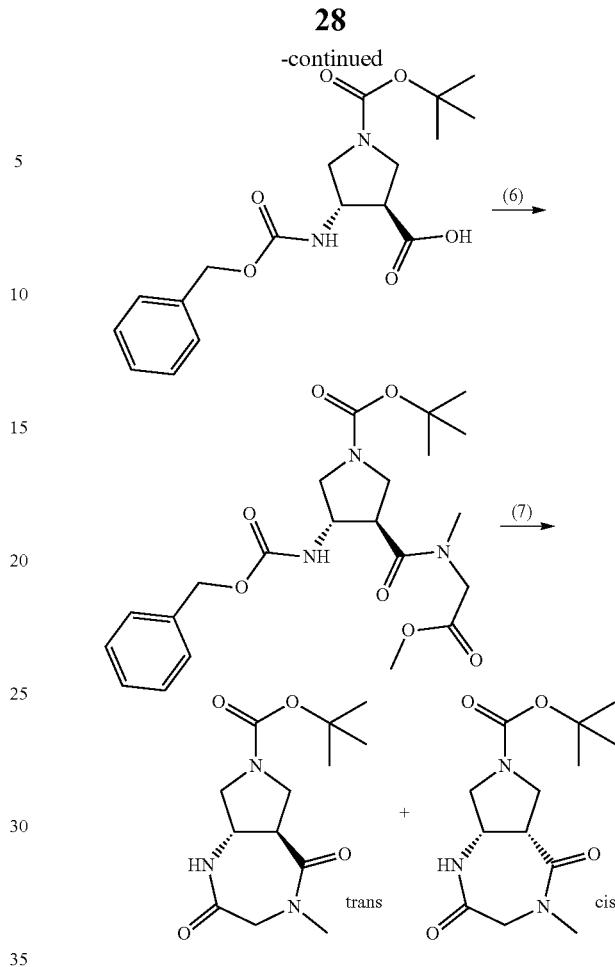

(1) Synthesis of Benzylethyl Fumarate

To a mixture of monoethyl fumarate ester (CAS No. 2459-05-4) (32.0 g, 222 mmol), potassium carbonate (30.7 g, 222 mmol) and DMF (900 mL) was added benzyl bromide (CAS No. 100-39-0) (24.0 mL, 202 mmol) at room temperature. The reaction mixture was stirred for 15 minutes at room temperature, stirred at 55° C. for 16 hours and then cooled to room temperature. It was then concentrated under reduced pressure to approximately ⅓ of its volume. Water (500 mL) and heptane (500 mL) were added thereto. The organic layer and aqueous layer were separated, and the aqueous layer was further extracted with heptane (300 mL). The combined organic layers were washed with brine (200 mL), dried over anhydrous magnesium sulfate, filtered and concentrated under reduced pressure. The residue was purified by column chromatography (silica gel, 0-10% ethyl acetate/n-heptane) to give the title compound (42.9 g).

$^1$H-NMR (400 MHz, CDCl$_3$) δ(ppm): 1.26-1.35 (m, 3H), 4.21-433 (m, 2H), 5.23 (s, 2H), 6.89 (s, 2H), 7.29-7.42 (m, 5H).

MS (ESI) m/z: 235 [M+H]$^+$ (2) Synthesis of (3SR,4SR)-3-benzyl 4-ethyl 1-benzylpyrrolidine-3,4-dicarboxylate To a mixture of benzylethyl fumarate (19.0 g, 81.1 mmol) and DCM (200 mL) was added N-(methoxymethyl)-N-(trimethylsilylmethyl)benzylamine (CAS No. 93102-05-7) (21.9 mL, 85.8 mmol) at 0° C., and then a mixture of TFA (0.400 mL, 5.19 mmol) and DCM (3.6 mL) was added. The reaction mixture was stirred at 0° C. for 15 minutes, and subsequently stirred at room temperature for 6 hours and 30 minutes. After adding an aqueous saturated sodium hydrogencarbonate solution (40 mL) to the mixture at room temperature, it was again stirred for 10 minutes. The organic layer and aqueous layer were separated, and the aqueous layer was extracted with DCM (20 mL). The combined organic layers were dried over anhydrous magnesium sulfate, filtered and concentrated under reduced pressure. The residue was purified by column chromatography (silica gel, 0-14% ethyl acetate/n-heptane) to give the title compound (28.5 g).

$^1$H-NMR (400 MHz, CDCl$_3$) δ(ppm): 1.22 (t, J=7.2 Hz, 3H), 2.77 (dd, J=9.4, 6.2 Hz, 1H), 2.84 (dd, J=9.0, 6.6 Hz, 1H), 2.87-2.96 (m, 2H), 3.43-3.54 (m, 2H), 3.60 (d, J=2.7 Hz, 2H), 4.14 (q, J=7.0 Hz, 2H), 5.15 (s, 2H), 7.26-7.38 (m, 10H).

MS (ESI) m/z: 368 [M+H]$^+$ (3) Synthesis of (3SR 4SR)-1-t-butoxycarbonyl-4-(ethoxycarbonyl)pyrrolidine-3-carboxylic acid To a mixture of (3SR,4SR)-3-benzyl 4-ethyl 1-benzylpyrrolidine-3,4-dicarboxylate (28.5 g, 77.5 mmol) and ethanol (380 mL) was added 20% palladium hydroxide-carbon (50% wet, 5.44 g, 3.87 mmol). The reaction mixture was stirred at room temperature for 18 hours under a hydrogen atmosphere. It was then stirred under a nitrogen atmosphere and water (65 mL) was added. After filtering the mixture, the filtrate was rinsed with ethanol/water (70 mL, 6/1 (v/v)). The filtrate was concentrated under reduced pressure to give a residue (142 g). To a mixture of the resulting residue, water (45 mL) and THF (100 mL) was added a mixture of sodium hydrogencarbonate (14.2 g, 169 mmol) and water (170 mL). The mixture was stirred for 5 minutes at room temperature. After then adding a mixture of di-t-butyl dicarbonate (203 g, 92.9 mmol) and THF (85 mL) to this reaction mixture, the resulting mixture was stirred at room temperature for 2 hours, and then concentrated under reduced pressure. To the resulting residue were added TBME (150 mL) and water (150 mL), and the organic layer and aqueous layer were separated. The organic layer was then extracted with water (50 mL). To the combined aqueous layers were added 2 N hydrochloric acid (85 mL) and ethyl acetate (200 mL) at 0° C. The organic layer and aqueous layer were separated, and the aqueous layer was extracted with ethyl acetate (50 mL). The combined organic layers were washed with brine, dried over anhydrous magnesium sulfate, filtered and concentrated under reduced pressure to give the title compound (21.7 g).

$^1$H-NMR (400 MHz, CDCl$_3$) δ(ppm): 1.28 (t, J=72 Hz, 3H), 1.46 (s, 9H), 333-3.66 (m, 4H), 3.79 (br.s, 2H), 4.21 (qd, J=7.1, 1.8 Hz, 2H).

MS (ESI) m/z: 573 [2M−H]$^−$ (4) Synthesis of (3RS,4SR)-1-t-butyl 3-ethyl 4-((benzyloxy)carbonyl)amino)pyrrolidine-1,3-dicarboxylate To a mixture of (3SR,4SR)-1-(t-butoxycarbonyl)-4-(ethoxycarbonyl)pyrrolidine-3-carboxylic acid (4.98 g, 173 mmol) and toluene (150 mL) were added triethylamine (2.90 mL, 20.8 mmol) and diphenylphosphorylazide (CAS No. 26386-88-9) (4.47 mL, 20.8 mmol), at room temperature. The reaction mixture was stirred at 80° C. for 1 hour, and then benzyl alcohol (CAS No. 100-51-6) (4.48 mL, 433 mmol) was added. The reaction mixture was stirred at 80° C. for 6 hours and then cooled to room temperature. Water (50 mL) was then added, and stirring was continued for 5 minutes at room temperature. The organic layer and aqueous layer were separated. The organic layer was washed with an aqueous saturated sodium hydrogencarbonate solution and brine in that order. The organic layer was dried over anhydrous magnesium sulfate, filtered and concentrated under reduced pressure. The residue was purified by column chromatography (silica gel, 0-50% TBME/n-heptane and 50-75% ethyl acetate/n-heptane) to give the title compound (5.27 g).

$^1$H-NMR (400 MHz, CDCl$_3$) δ(ppm): 1.25 (t, J=7.4 Hz, 3H), 1.45 (s, 9H), 2.91-3.29 (m, 2H), 3.56-3.88 (m, 3H), 4.17 (q, J=7.4 Hz, 21), 4.42 (br.s, 1H), 4.92 (br.s, 1H), 5.11 (s, 2H), 7.29-7.41 (m, 5H).

MS (ESI) m/z: 785 [2M+H]$^+$ (5) Synthesis of (3RS,4SR)-4-(((benzyloxy)carbonyl)amino)-1-(t-butoxycarbonyl)pyrrolidine-3-carboxylic acid To a mixture of (3RS,4SR)-1-t-butyl 3-ethyl 4-(((benzyloxy)carbonyl)amino)pyrrolidine-1,3-dicarboxylate (21.0 g, 53.4 mmol) and THF (250 mL) was added an aqueous 2 N sodium hydroxide solution (125 mL, 250 mmol) at 25° C. The reaction mixture was subsequently stirred at room temperature for 2 hours and 30 minutes. To this mixture were added TBME (250 mL) and water (125 mL), and the organic layer and aqueous layer were separated. The organic layer was then extracted with water (63 mL). To the combined aqueous layers were added 5 N hydrochloric acid (50 mL) and ethyl acetate (200 mL) at 0° C. The organic layer and aqueous layer were separated, and the aqueous layer was extracted with ethyl acetate (50 mL). The combined organic layers were washed with brine. The organic layers were then dried over anhydrous magnesium sulfate, filtered and concentrated under reduced pressure to give the title compound (183 g).

$^1$H-NMR (400 MHz, CDCl$_3$) δ(ppm): 1.46 (s, 9H), 3.02-338 (m, 2H), 3.62-3.86 (m, 3H), 4.44 (br.s, 1H), 5.12 (br.s, 3H), 7.32-7.41 (m, 5H).

MS (ESI) m/z: 727 [2M−H]$^−$ (6) Synthesis of (3SR,4RS)-t-butyl 3-(((benzyloxy)carbonyl)amino)-4-((2-methoxy-2-oxoethyl)(methyl)carbamoyl)pyrrolidine-1-carboxylate To a mixture of (3RS,4SR)-4-(((benzyloxy)carbonyl)amino)-1-(t-butoxycarbonyl)pyrrolidine-3-carboxylic acid (13.1 g, 36.0 mmol), sarcosine methyl ester hydrochloride (CAS No. 13515-93-0) (6.02 g, 43.1 mmol), HOBT (5.83 g, 43.1 mmol) and DMF (150 mL) were added triethylamine (12.5 mL, 89.9 mmol) and EDC (8.27 g, 43.1 mmol) in that order, at 25° C. The resulting mixture was subsequently stirred at room temperature for 5 hours and 40 minutes. Ethyl acetate (400 mL) and water (100 mL) were then added and the organic layer and aqueous layer were separated. The aqueous layer was extracted with ethyl acetate (100 mL). The combined organic layers were washed with an aqueous saturated sodium hydrogencarbonate solution and brine in that order. The organic layer was dried over anhydrous magnesium sulfate, filtered and concentrated under reduced pressure. The residue was purified by column chromatography (silica gel, 50-75% ethyl acetate/n-heptane) to give the title compound (14.9 g).

¹H-NMR (400 MHz, CDCl₃) δ(ppm): 1.45 (s, 9H), 2.97 (s, 1H), 3.13-3.28 (m, 2H), 3.33-3.69 (m, 5H), 3.70-3.83 (m, 3H), 4.00-4.44 (m, 3H), 4.97-5.19 (m, 3H), 7.30-7.45 (m, 5H).

MS (ESI) m/z: 450 [M+H]⁺

(7) Synthesis of (5aRS,8aSR)-t-butyl 4-methyl-2,5-dioxooctahydropyrrolo[3,4-e][1,4]diazepine-7(1H)-carboxylate (trans-form) and (5aSR,8aSR)-t-butyl 4-methyl-2,5-dioxooctahydropyrrolo[3,4-e][1,4]diazepine-7(1H)-carboxylate (cis-form)

To a mixture of (3SR,4RS)-t-butyl 3-(((benzyloxy)carbonyl)amino)-4-((2-methoxy-2-oxoethyl) (methyl)carbamoyl) pyrrolidine-1-carboxylate (1.50 g, 334 mmol) and ethanol (33 mL) was added 20% palladium hydroxide-carbon (50% wet, 234 mg, 0.167 mmol), at 25° C. The reaction mixture was stirred at 25° C. for 3 hours under a hydrogen atmosphere. It was then stirred under a nitrogen atmosphere and subsequently filtered with Celite™. The filtrate was concentrated under reduced pressure. THF (66 mL) was added to the resulting residue, and then TBD (697 mg, 5.01 mmol) was added and the mixture was stirred at 25° C. for 5 hours. It was then concentrated under reduced pressure. The residue was purified by column chromatography (silica gel, 5-20% methanol/ethyl acetate) to give the title trans-form (369 mg) and the title cis-form (274 mg). trans-form ¹H-NMR (400 MHz, CDCl₃) δ(ppm): 1.46 (s, 9H), 3.09 (s, 3H), 3.17 (t, J=10.0 Hz, 1H), 3.42-3.55 (m, 1H), 3.66-4.04 (m, 5H), 4.58 (d, J=17.6 Hz, 1H).

MS (ESI) m/z: 284 [M+H]⁺ cis-form

¹H-NMR (400 MHz, CDCl₃) δ(ppm): 1.47 (s, 9H), 3.12 (s, 3H), 3.19-334 (m, 1H), 3.48-3.72 (m, 3H), 3.78 (br.s, 1H), 3.93 (br.s, 1H), 4.21 (br.s, 1H), 4.56 (d, J=16.0 Hz, 1H), 5.60 (br.s, 1H).

MS (ESI) m/z: 284 [M+H]⁺

Production Example 18

Synthesis of (5aRS,8aSR)-(9H-fluoren-9-yl)methyl 4-methyl-2,5-dioxooctahydropyrrolo[3,4-e][1,4]diazepine-7(1H)-carboxylate (trans-form)

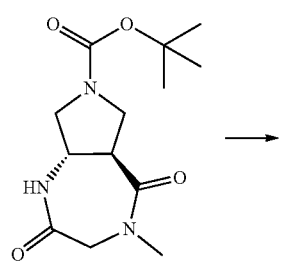

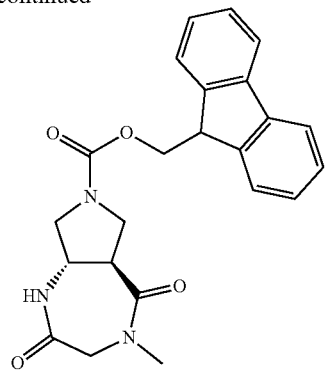

To a mixture of (5aRS,8aSR)-t-butyl 4-methyl-2,5-dioxooctahydropyrrolo[3,4-e][1,4]diazepine-7(1H)-carboxylate (trans-form) obtained in Production Example 17(7) (369 mg, 130 mmol) and DCM (8 mL) was added TFA (2.00 mL, 26.0 mmol) at 25° C. The reaction mixture was stirred at 25° C. for 2 hours and then concentrated under reduced pressure. To the residue were added THF (6 mL) and an aqueous saturated sodium hydrogencarbonate solution (6.00 mL). To this mixture was added 9-fluorenylmethylsuccinimidyl carbonate (395 mg, 1.17 mmol) and the resulting mixture was stirred at 25° C. for 17 hours, after which 9-fluorenylmethylsuccinimidyl carbonate (21.9 mg, 0.0651 mmol) was added. After stirring the resulting mixture at 25° C. for 1 hour, ethyl acetate was added and the organic layer and aqueous layer were separated. The aqueous layer was extracted 5 times with ethyl acetate. The combined organic layers were dried over anhydrous magnesium sulfate and filtered, and the filtrate was concentrated under reduced pressure. The residue was purified by column chromatography (silica gel, 5-20% methanol/ethyl acetate) to give the title compound (501 mg).

¹H-NMR (400 MHz, CDCl₃) δ(ppm): 3.05-330 (m, 4H), 3.40-3.63 (m, 1H), 3.77-4.10 (m, 5H), 4.19-4.29 (m, 1H), 4.33-4.52 (m, 2H), 4.54-4.66 (m, 1H), 6.04-6.30 (m, 1H), 7.29-7.36 (m, 2H), 7.38-7.45 (m, 2H), 7.54-7.63 (m, 2H), 7.77 (d, J=7.4 Hz, 2H).

MS (ESI) m/z: 406 [M+H]⁺

Production Example 19

Synthesis of (5aSR,8aSR)(9H-fluoren-9-yl)methyl 4-methyl-2,5-dioxooctahydropyrrolo[3,4-e][1,4]diazepine-7(1H)-carboxylate (cis-form)

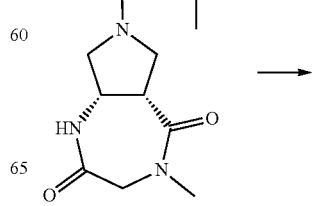

-continued

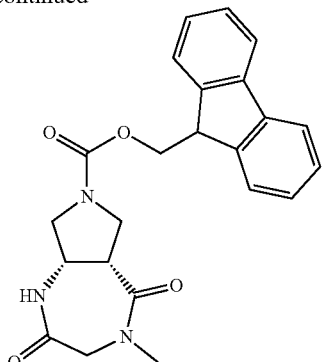

To a mixture of (5aSR,8aSR)-t-butyl 4-methyl-2,5-dioxooctahydropyrrolo[3,4-e][1,4]diazepine-7(1H)-carboxylate (cis-form) obtained in Production Example 17(7) (247 mg, 0.872 mmol) and DCM (8 mL) was added TFA (2.00 mL, 26.0 mmol) at 25° C. The reaction mixture was stirred at 25° C. for 2 hours and then concentrated under reduced pressure. To the residue were added THF (6 mL) and an aqueous saturated sodium hydrogencarbonate solution (6.00 mL). To this mixture was added 9-fluorenylmethylsuccinimidyl carbonate (265 mg, 0.784 mmol), and the resulting mixture was stirred at 25° C. for 17 hours. After then adding 9-fluorenylmethylsuccinimidyl carbonate (14.7 mg, 0.0436 mmol), the resulting mixture was stirred at 25° C. for 1 hour. Ethyl acetate was added to the mixture, and the organic layer and aqueous layer were separated. The aqueous layer was extracted 5 times with ethyl acetate. The combined organic layers were dried over anhydrous magnesium sulfate and filtered, and the filtrate was concentrated under reduced pressure. The residue was purified by column chromatography (silica gel, 5-20% methanol/ethyl acetate) to give the title compound (329 mg).

$^1$H-NMR (400 MHz, CDCl$_3$) δ(ppm): 3.07-3.20 (m, 3H), 3.25-3.97 (m, 5H), 4.11-4.63 (m, 6H), 5.69 (br.s, 1H), 7.30-7.37 (m, 2H), 7.37-7.47 (m, 2H), 7.54-7.69 (m, 2H), 7.77 (d, J=7.4 Hz, 2H).

MS (ESI) m/z: 406 [M+H]$^+$

Production Example 20

Synthesis of (9H-fluorene-9-yl)methyl (5aR,8aR)-4-methyl-2,5-dioxooctahydropyrrolo[3,4-e][1,4]diazepine-7(1H)-carboxylate

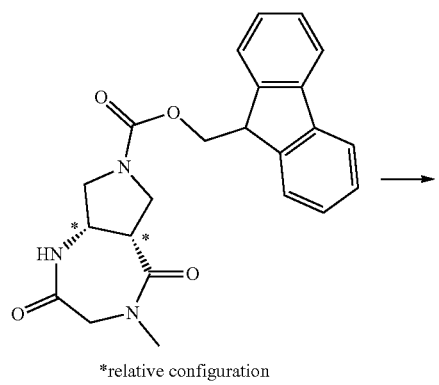

*relative configuration

-continued

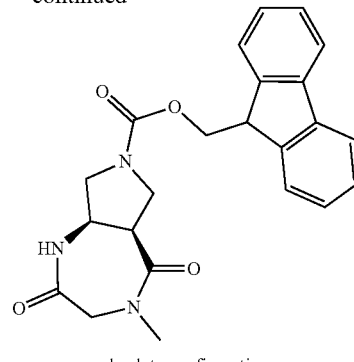

absolute configuration

After repeated optical resolution of (5aSR,8aSR)(9H-fluoren-9-yl)methyl 4-methyl-2,5-dioxooctahydropyrrolo[3,4-e][1,4]diazepine-7(1H)-carboxylate (cis-form) obtained in Production Example 19 (500 mg, 1.23 mmol) by HPLC (CHIRALPAK™ IB (2 cmφ×25 cm), elution solvent: ethanol, flow rate: 11 ml/min.), the title compound with a shorter retention time was obtained (224 mg).

$^1$H-NMR (400 MHz, CDCl$_3$) δ(ppm): 3.10-3.17 (m, 3H), 3.27-3.93 (m, 5H), 4.14-4.61 (m, 6H), 5.44-5.65 (m, 1H), 7.29-7.36 (m, 2H), 7.37-7.45 (m, 2H), 7.61 (br.dd, J=17.8, 10.0 Hz, 2H), 7.77 (d, J=7.4 Hz, 2H).

MS (ES) m/z: 406 [M+H]$^+$

HPLC Analysis:

(Analysis conditions) Column: CHIRALPAK™ IB (Daicel Chemical Industries, Ltd.) (0.46 cmφ×15 cm), 40° C., elution solvent: ethanol, flow rate: 1 ml/min., detection: UV (254 nm)

(Analysis results) Analysis of the obtained title compound with the shorter retention time under the conditions described above revealed a retention time of 6.97 minutes, (−) optical rotation and an enantiomeric excess of >99% ee.

Production Example 21

Synthesis of methyl 2-amino-6-fluoro-4,5,6,7-tetrahydrobenzo[b]thiophene-3-carboxylate

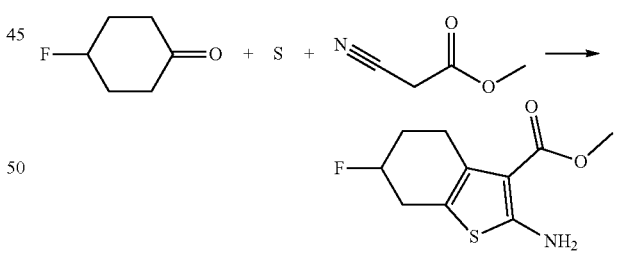

To a mixture of 4-fluorocyclohexanone (CAS No. 68223-64-3) (2 g, 17.2 mmol) and methyl cyanoacetate (CAS No. 105-34-0) (1.52 mL, 17.2 mmol) in ethanol (20 mL) were added sulfur (CAS No. 7704-34-9) (0.552 g, 17.2 mmol) and morpholine (1.51 mL, 17.2 mmol) in that order, at room temperature. The reaction mixture was stirred at room temperature for 3 days. The deposited powder was collected by filtration and then rinsed with ethanol and dried under reduced pressure to give the title compound (1.61 g).

$^1$H-NMR (400 MHz, CDCl$_3$) δ(ppm): 1.86-2.13 (m, 2H), 2.69-3.00 (m, 4H), 3.73-3.88 (m, 3H), 4.89-5.16 (m, 1H), 5.90-6.10 (m, 2H).

MS (ESI) m/z: 230 [M+H]$^+$

Example 1

Synthesis of (3aS,14aR)-5-methyl-3,3a,5,6-tetrahydro-1H-benzofuro[3',2':4,5]pyrimido[1,2-a]cyclopenta[f][1,4]diazepine-4,13(2H,14aH)-dione

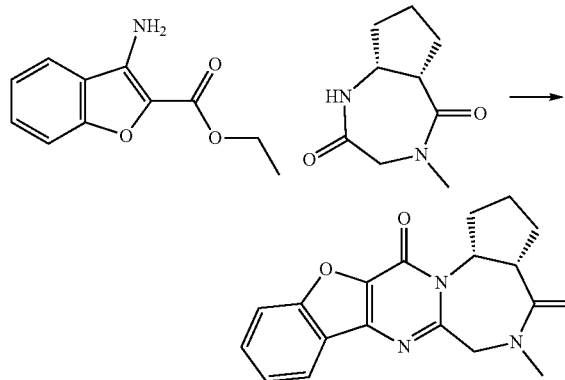

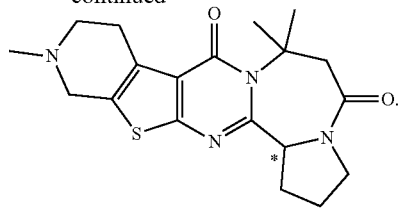

*Single isomer, but absolute configuration is not determined

To a mixture of ethyl 3-aminobenzofuran-2-carboxylate (CAS No. 39786-35-1) (169 mg, 0.823 mmol), (5aS,8aR)-4-methyloctahydrocyclopenta[e][1,4]diazepine-2,5-dione obtained in Production Example 1 (100 mg, 0.549 mmol) and DCE (15 mL) was added phosphorus oxychloride (0.102 mL, 1.10 mmol) at room temperature. The reaction mixture was stirred at 80° C. for 6 hours. Sodium ethoxide (20% ethanol solution, 1.70 mL, 439 mmol) was then added at room temperature, and the reaction mixture was stirred at room temperature for 2 hours. Water and ethyl acetate were then added and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 0-10% methanol/ethyl acetate) to give the title compound (124 mg).

$^1$H-NMR (400 MHz, CDCl$_3$) δ(ppm): 1.59-1.77 (m, 2H), 1.90-2.24 (m, 2H), 2.33-2.47 (m, 1H), 2.54-2.66 (m, 1H), 3.15 (s, 3H), 3.50-3.63 (m, 1H), 4.34 (d, J=15.8 Hz, 1H), 4.85 (d, J=15.8 Hz, 1H), 5.82-6.00 (m, 1H), 7.42-7.49 (m, 1H), 7.56-7.64 (m, 1H), 7.65-7.72 (m, 1H), 8.05 (d, J=7.8 Hz, 1H)

MS (ESI) m/z: 324 [M+H]$^+$

Example 2

Synthesis of (+)-7,7,12-trimethyl-1,2,3,6,7,10,11,12,13,15b-decahydropyrido[4'',3'':4',5']thieno[2',3':4,5]pyrimido[1,2-a]pyrrolo[2,1-c][1,4]diazepine-5,9-dione

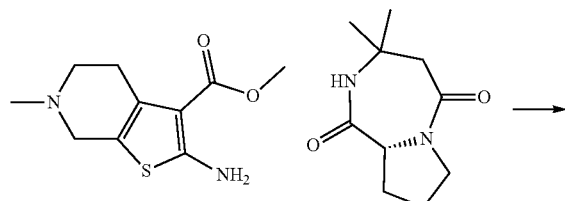

To a mixture of methyl 2-amino-6-methyl-4,5,6,7-tetrahydrothieno[2,3-c]pyridine-3-carboxylate obtained in Production Example 2 (CAS No. 303998-84-7) (86 mg, 0.382 mmol), (R)-3,3-dimethylhexahydro-1H-pyrrolo[1,2-a][1,4]diazepine-1,5(2H)-dione obtained in Production Example 3 (50 mg, 0.255 mmol) and DCE (3 mL) was added phosphorus oxychloride (0.047 mL, 0.51 mmol) at room temperature. The reaction mixture was stirred overnight at 60° C., and then sodium ethoxide (20% ethanol solution, 3 mL, 7.76 mmol) was added at room temperature. The resulting mixture was stirred at room temperature for 2 hours, an aqueous saturated sodium hydrogencarbonate solution and ethyl acetate were added, and the organic layer was separated. After rinsing the organic layer with brine, it was dried over anhydrous magnesium sulfate and filtered, and the filtrate was concentrated under reduced pressure. The residue was purified by column chromatography (NH silica gel, 20-100% ethyl acetate/n-heptane and 0 to 5% methanol/ethyl acetate), (silica gel, 2-80% methanol/ethyl acetate) in that order to give a racemate of the title compound (42 mg).

MS (ESI) m/z: 373 [M+H]$^+$ (Analysis conditions) Column: CHIRALPAK™ IA (Daicel Chemical Industries, Ltd.) (0.46 cmφ×15 cm), 40° C., elution solvent: ethanol/hexane=20/80 (v/v), flow rate: 1 ml/min., detection: UV (254 nm)

(Analysis results) Analysis of the obtained title compound under the conditions described above showed a peak with (+) optical rotation at a retention time of 5.96 minutes and a peak with (−) optical rotation at a retention time of 10.18 minutes.

Optical resolution of the obtained racemate of the title compound (42 mg, 0.113 mmol) by HPLC (CHIRALPAK™ IA (2 cmφ×25 cm), elution solvent: ethanol/hexane=20/80 (v/v), flow rate: 10 ml/min.) produced a chiral form with a shorter retention time (14.6 mg).

Shorter-retention-time chiral form: $^1$H-NMR (400 MHz, CDCl3) δ(ppm): 1.82 (s, 3H), 1.84-1.99 (m, 5H), 2.40-2.58 (m, 5H), 2.76 (t, J=5.9 Hz, 2H), 2.90-3.02 (m, 1H), 3.12 (t, J=5.9 Hz, 2H), 3.39 (dt, J=11.6, 6.7 Hz, 1H), 3.47 (d, J=14.8 Hz, 1H), 3.62 (d, J=1.6 Hz, 2H), 3.80 (dt, J=11.4, 6.8 Hz, 1H), 5.04 (dd, J=7.2, 5.7 Hz, 1H).

MS (ESI) m/z: 373 [M+H]$^+$ (Analysis conditions) Column: CHIRALPAK™ IA (Daicel Chemical Industries, Ltd.) (0.46 cmφ×15 cm), 40° C., elution solvent ethanol/hexane=20/80 (v/v), flow rate: 1 m/min., detection: UV (254 nm) (Analysis results) The retention time of the title compound was 5.91 minutes, the optical purity was >99% ee and the optical rotation was (+).

Example 3

Synthesis of (3aS,14aR)-10-fluoro-5-methyl-3,3a,5,6-tetrahydro-1H-benzofuro[3',2':4,5]pyrimido[1,2-a]cyclopenta[f][1,4]diazepine-4,13(2H,14aH)-dione

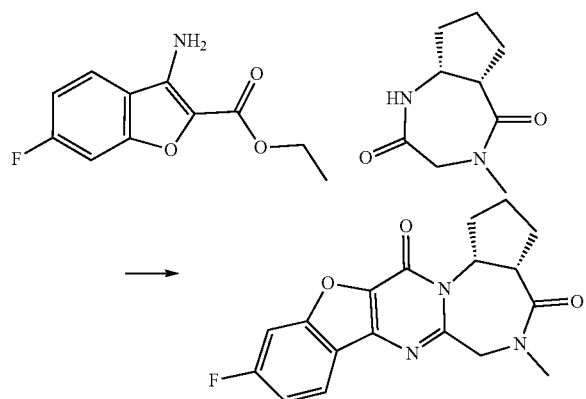

To a mixture of ethyl 3-amino-6-fluorobenzofuran-2-carboxylate obtained in Production Example 4 (58.8 mg, 0.263 mmol), (5aS,8aR)-4-methyloctahydrocyclopenta[e][1,4]diazepine-2,5-dione obtained in Production Example 1 (40.0 mg, 0.220 mmol) and DCE (3 mL) was added phosphorus oxychloride (0.0307 mL, 0329 mmol) at room temperature. The reaction mixture was stirred at 100° C. for 1 hour under microwave irradiation, sodium ethoxide (20% ethanol solution, 0.679 mL, 1.76 mmol) was added room temperature, and the resulting mixture was stirred at room temperature for 2 hours. Water and ethyl acetate were then added and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 0-30% methanol/ethyl acetate). The concentrated residue that was obtained was triturated with diethyl ether. The precipitate was collected by filtration to give the title compound (22.8 mg).

$^1$H-NMR (400 MHz, CDCl$_3$) δ(ppm): 1.60-1.75 (m, 2H), 1.95-2.22 (m, 2H), 2.34-2.46 (m, 1H), 2.49-2.67 (m, 1H), 3.14 (d, J=0.9 Hz, 3H), 3.49-3.62 (m, 1H), 4.31 (d, J=15.4 Hz, 1H), 4.83 (d, J=15.4 Hz, 1H), 5.76-5.99 (m, 1H), 7.17-7.23 (m, 1H), 7.34-7.39 (m, 1H), 7.91-8.09 (m, 1H)

MS (ESI) m/z: 342 [M+H]$^+$

Example 4

Synthesis of (3aS,14aR)-5,8,10-trimethyl-3,3a,5,6-tetrahydro-1H-cyclopenta[f]pyrido[3'',2'':4',5']furo[3',2':4,5]pyrimido[1,2-a][1,4]diazepine-4,13(2H,14aH)-dione

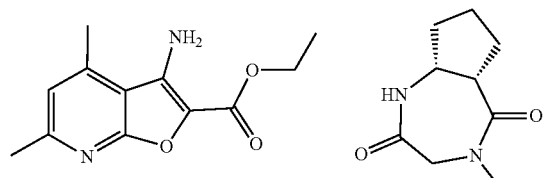

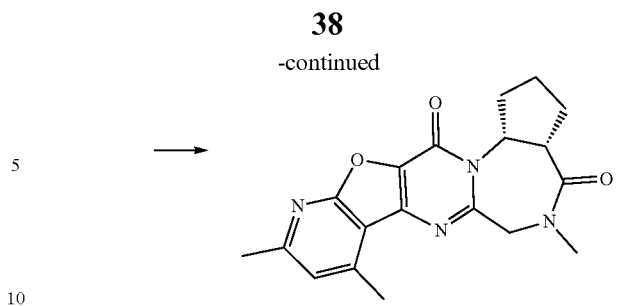

To a mixture of ethyl 3-amino-4,6-dimethylfuro[2,3-b]pyridine-2-carboxylate obtained in Production Example 5 (93.0 mg, 0395 mmol), (5aS,8aR)-4-methyloctahydrocyclopenta[e][1,4]diazepine-2,5-dione obtained in Production Example 1 (60.0 mg, 0329 mmol) and DCE (4.5 mL) was added phosphorus oxychloride (0.0460 mL, 0.494 mmol) at room temperature. The reaction mixture was stirred at 90° C. for 1.5 hours, and then sodium ethoxide (20% ethanol solution, 1.02 mL, 2.63 mmol) was added at room temperature and the resulting mixture was stirred overnight at room temperature. Water and ethyl acetate were then added and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 25% methanol/ethyl acetate) to give the title compound (65.0 mg).

$^1$H-NMR (400 MHz, CDCl$_3$) δ(ppm): 1.61-1.75 (m, 2H), 1.95-2.23 (m, 2H), 2.32-2.44 (m, 1H), 2.52-2.61 (m, 1H), 2.65 (s, 3H), 2.81 (s, 3H), 3.13 (d, J=0.9 Hz, 3H), 3.48-3.63 (m, 1H), 4.29 (d, J=15.4 Hz, 1H), 4.81 (d, J=15.4 Hz, 1H), 5.78-5.96 (m, 1H), 7.00-7.14 (m, 1H)

MS (ESI) m/z: 353 [M+H]$^+$

Example 5

Synthesis of (3aR,14aR)-10-fluoro-5-methyl-3,3a,5,6-tetrahydro-1H-benzofuro[3',2':4,5]pyrimido[1,2-a]cyclopenta[f][1,4]diazepine-4,13(2H,14aH)-dione

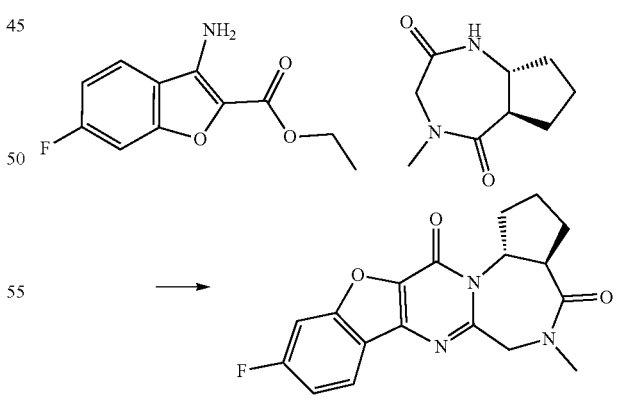

To a mixture of ethyl 3-amino-6-fluorobenzofuran-2-carboxylate obtained in Production Example 4 (33.7 mg, 0.151 mmol), (5aR,8aR)-4-methyloctahydrocyclopenta[e][1,4]diazepine-2,5-dione obtained in Production Example 6 (25.0 mg, 0.137 mmol) and DCE (1.5 mL) was added phosphorus oxychloride (0.0256 mL, 0274 mmol) at room temperature. The reaction mixture was stirred at 90° C. for 5 hours, and then an aqueous saturated sodium hydrogencarbonate solution (1 mL) was added and the resulting mixture was stirred overnight at 90° C. and then cooled to room temperature, and the organic layer was separated. The organic layer was directly purified by column chromatography (silica gel, 20-30%, methanol/ethyl acetate) to give the title compound (18.2 mg).

¹H-NMR (400 MHz, CDCl₃) δ(ppm): 1.40-1.46 (m, 1H), 1.71-2.24 (m, 4H), 3.12 (s, 3H), 3.19-335 (m, 1H), 3.45-3.62 (m, 1H), 4.28-4.50 (m, 2H), 5.38 (d, J=17.2 Hz, 1H), 7.12-7.22 (m, 1H), 7.31-7.41 (m, 1H), 7.89-8.03 (m, 1H)

MS (ESI) m/z: 342 [M+H]⁺

Example 6

Synthesis of (3aR,14aR-5-methyl-10-(trifluoromethyl)-3,3a,5,6-tetrahydro-1H-benzofuro[3',2':4,5]pyrimido[1,2-a]cyclopenta[f][1,4]diazepine-4,13(2H,14aH)-dione

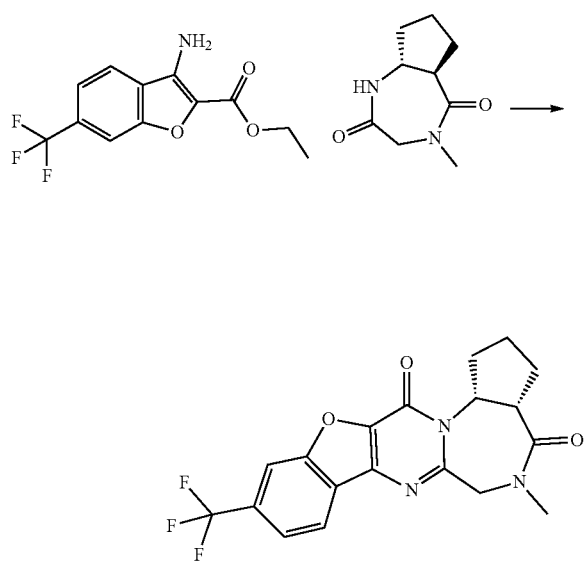

To a mixture of ethyl 3-amino-6-trifluormethyl)benzofuran-2-carboxylate obtained in Production Example 7 (18.0 mg, 0.0660 mmol), (5aR,8aR)-4-methyloctahydrocyclopenta[e][1,4]diazepine-2,5-dione obtained in Production Example 6 (10.0 mg, 0.0550 mmol) and DCE (3 mL) was added phosphorus oxychloride (0.0102 mL, 0.110 mmol) at room temperature. The reaction mixture was stirred at 90° C. for 15 hours, and then an aqueous saturated sodium hydrogencarbonate solution (1 mL) was added and the mixture was stirred for one day at 90° C. The resulting mixture was cooled to room temperature and the organic layer was separated. The organic layer was directly purified by column chromatography (silica gel, 10-20%, methanol/ethyl acetate) to give the title compound (133 mg).

¹H-NMR (400 MHz, CDCl₃) δ(ppm): 137-1.50 (m, 1H), 1.73-1.87 (m, 1H), 1.90-2.26 (m, 3H), 3.13 (s, 3H), 3.19-336 (m, 1H), 3.42-3.70 (m, 1H), 4.36-4.50 (m, 2H), 5.39 (d, J=17.7 Hz, 1H), 7.65-7.76 (m, 1H), 7.92 (s, 1H), 8.08-8.20 (m, 1H)

MS (ESI) m/z: 392 [M+H]⁺

Example 7

Synthesis of (3aS,14aR)-10-(2,2-difluoroethyl)-5-methyl-2,3,3a,5,6,9,10,11,12,14a-decahydro-1H-cyclopenta[f]pyrido[4'',3'':4',5']thieno[2',3':4,5]pyrimido[1,2-a][1,4]diazepine-4,13-dione

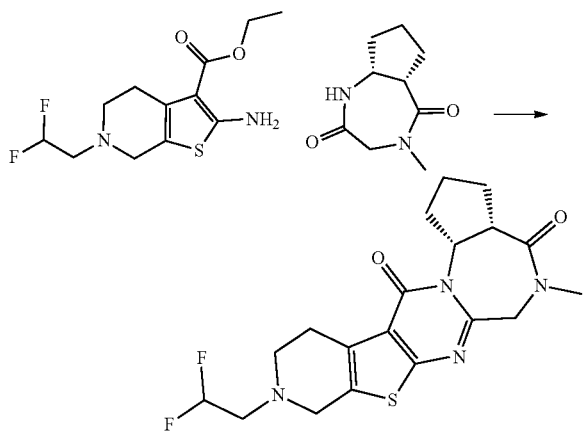

To a mixture of (5aS,8aR)-4-methyloctahydrocyclopenta[e][1,4]diazepine-2,5-dione obtained in Production Example 1 (123 mg, 0.675 mmol), ethyl 2-amino-6-(2,2-difluoroethyl-4,5,6,7-tetrahydrothieno[2,3-c]pyridine-3-carboxylate obtained in Production Example 8 (120 mg, 0.413 mmol) and DCE (5 mL) was added phosphorus oxychloride (0.262 mL, 2.81 mmol) at room temperature. The reaction mixture was stirred at 80° C. for 15 hours, and then an aqueous saturated sodium hydrogencarbonate solution (5 mL) was added at room temperature and the mixture was stirred at room temperature for 2 hours, after which ethyl acetate and an aqueous saturated sodium hydrogencarbonate solution were added and the organic layer was separated. The aqueous layer was extracted with ethyl acetate. The combined organic layers were washed with an aqueous saturated sodium hydrogencarbonate solution, dried over anhydrous magnesium sulfate, filtered and concentrated under reduced pressure. The residue was purified by column chromatography (NH silica gel, 30-75%, ethyl acetate/n-heptane) to give the title compound (56.9 mg).

¹H-NMR (400 MHz, CDCl₃) δ(ppm): 1.53-1.69 (m, 2H), 1.95-2.16 (m, 2H), 2.34 (dt, J=12.6, 6.5 Hz, 1H), 2.46-2.57 (m, 1H), 2.90-3.01 (m, 4H), 3.07-3.15 (m, 5H), 3.44-3.51 (m, 1H), 3.85 (s, 2H), 4.16 (d, J=15.6 Hz, 1H), 4.73 (d, J=15.6 Hz, 1H), 5.65-6.15 (m, 2H).

MS (ES) r/z: 409 [M+H]⁺

Example 8

Synthesis of (3aS,14aR)-10-(2-methoxyethyl-5-methyl-2,3,3a,5,6,9,10,11,12,14a-decahydro-1H-cyclopenta[f]pyrido[4'',3'':4',5']thieno[2',3':4,5]pyrimido[1,2-a][1,4]diazepine-4,13-dione

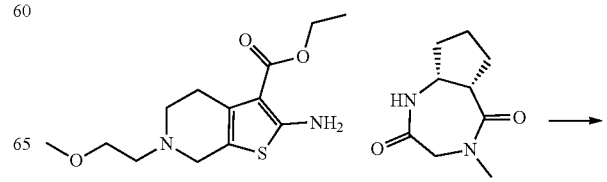

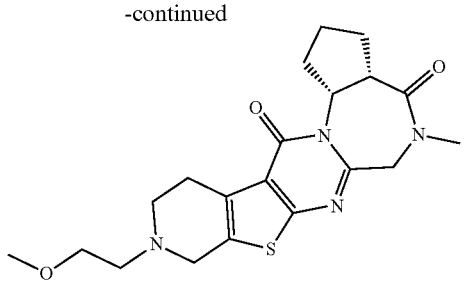

To a mixture of (5aS,8aR)-4-methyloctahydrocyclopenta[e][1,4]diazepine-2,5-dione obtained in Production Example 1 (123 mg, 0.675 mmol), ethyl 2-amino-6-(2-methoxyethyl)-4,5,6,7-tetdrahydrothieno[2,3-c]pyridine-3-carboxylate obtained in Production Example 9 (160 mg, 0.563 mmol) and DCE (5 mL) was added phosphorus oxychloride (0262 mL, 2.81 mmol) at room temperature. The reaction mixture was stirred at 80° C. for 15 hours, an aqueous saturated sodium hydrogencarbonate solution (5 mL) was added at room temperature and the mixture was stirred at room temperature for 2 hours, after which ethyl acetate and an aqueous saturated sodium hydrogencarbonate solution were added and the organic layer was separated. The aqueous layer was extracted with ethyl acetate. The combined organic layers were washed with an aqueous saturated sodium hydrogencarbonate solution, dried over anhydrous magnesium sulfate, filtered and concentrated under reduced pressure. The residue was purified by column chromatography (NH silica gel, 30-75%, ethyl acetate/n-heptane) to give the title compound (643 mg).

$^1$H-NMR (400 MHz, CDCl$_3$) δ(ppm): 1.53-1.69 (m, 2H), 1.97-2.05 (m, 1H), 2.06-2.17 (m, 1H), 2.29-2.39 (m, 1H), 2.46-2.55 (m, 1H), 2.79 (t, J=53 Hz, 2H), 2.85-2.91 (m, 2H), 3.08-3.15 (m, 5H), 3.37 (s, 3H), 3.47 (td, J=10.8, 8.2 Hz, 1H), 3.58 (t, J=5.5 Hz, 2H), 3.77 (s, 2H), 4.15 (d, J=15.6 Hz, 1H), 4.72 (d, J=15.6 Hz, 1H), 5.64-5.82 (m, 1H).

MS (ESI) m/z: 403 [M+H]$^+$

Example 9

Synthesis of (3aS,14aR)-10-(difluoromethyl-5-methyl-3,3a,5,6-tetrahydro-1H-benzofuro[3',2':4,5]pyrimido[1,2-a]cyclopenta[f][1,4]diazepine-4,13(2H,14aH)-dione

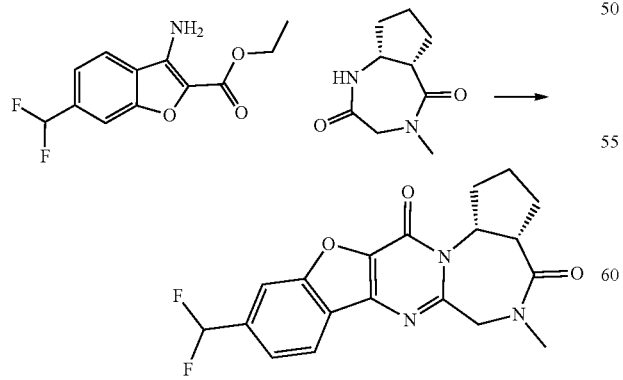

To a mixture of ethyl 3-amino-6-(difluoromethyl)benzofuran-2-carboxylate obtained in Production Example 10 (30.8 mg, 0.121 mmol), (5aS,8aR)-4-methyloctahydrocyclopenta[e][1,4]diazepine-2,5-dione obtained in Production Example 1 (20.0 mg, 0.110 mmol) and DCE (1.5 mL) was added phosphorus oxychloride (0.0154 mL, 0.165 mmol) at room temperature. The reaction mixture was stirred at 90° C. for 2 hours, an aqueous saturated sodium hydrogencarbonate solution (1 mL) was added and the mixture was stirred overnight at 90° C., after which ethyl acetate was added to the reaction mixture and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 20% methanol/ethyl acetate). The concentrated residue that was obtained was triturated with diethyl ether. The precipitate was collected by filtration and rinsed with diethyl ether to give the title compound (22.5 mg).

$^1$H-NMR (400 MHz, CDCl$_3$) δ(ppm): 1.62-1.75 (m, 2H), 1.99-2.21 (m, 2H), 2.33-2.48 (m, 1H), 2.54-2.69 (m, 1H), 3.15 (s, 3H), 3.48-3.62 (m, 1H), 4.33 (d, J=15.9 Hz, 1H), 4.84 (d, J=15.4 Hz, 1H), 5.82-5.96 (m, 1H), 6.81 (t, J=56.2 Hz, 1H), 7.56-7.65 (m, 1H), 7.82 (s, 1H), 8.06-8.18 (m, 1H)

MS (ESI) m/z: 374 [M+H]$^+$

Example 10

Synthesis of (2R,15bR)-2-fluoro-7,7,12-trimethyl-1,2,3,6,7,10,11,12,13,15b-decahydro-5H,9H-pyrido[4'',3'':4',5']thieno[2'3'':4,5]pyrimido[1,2-a]pyrrolo[2,1-c][1,4]diazepine-5,9-dione

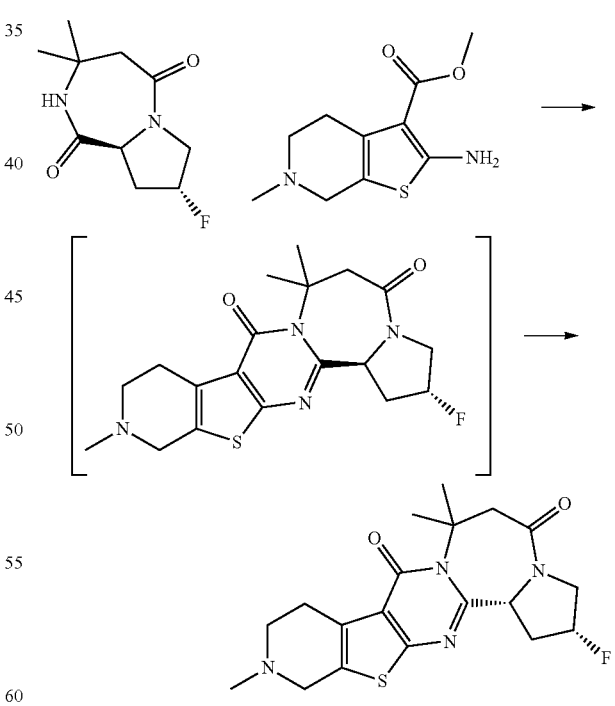

To a mixture of methyl 2-amino-6-methyl-4,5,6,7-tetrahydrothieno[2,3-c]pyridine-3-carboxylate obtained in Production Example 2 (634 mg, 2.80 mmol), (8R,9aS)-8-fluoro-3,3-dimethylhexahydro-1H-pyrrolo[1,2-a][1,4]diazepine-1,5(2H)-dione obtained in Production Example 11 (500 mg, 233 mmol) and DCE (25 mL) was added phosphorus oxychloride (1.09 mL, 11.7 mmol) at room temperature. The reaction mixture was stirred at 50° C. for 15 hours. An aqueous saturated sodium carbonate solution and ethyl acetate were added at 0° C., and then the organic layer was separated and concentrated under reduced pressure. To a mixture of the obtained residue and methanol (25.0 mL) was added a 1 N sodium hydroxide aqueous solution (2.33 mL, 2.33 mmol) at 0° C., and the mixture was stirred at 0° C. for 1 hour. It was then restored to room temperature, after which a 1 N sodium hydroxide aqueous solution (2.33 mL, 233 mmol) was added and stirring was continued for 1 hour. After adding hydrochloric acid and ethyl acetate, the organic layer was separated and concentrated under reduced pressure. The residue was purified by column chromatography (NH silica gel, 30-50% ethyl acetate/n-heptane) to give the title compound as a stereoisomer (trans-form) (200 ng). This was combined with a trans-form (50 mg) separated and purified from a stereoisomeric mixture of the title compound obtained in the same manner, as a trans-form mixture (250 mg) in 1,4-dioxane (30.0 mL), and then an aqueous saturated sodium hydrogencarbonate solution (30.0 mL) was added at room temperature. After stirring the reaction mixture at 80° C. for 5 hours, ethyl acetate was added at room temperature, and the organic layer was separated and concentrated under reduced pressure. The resulting residue was fractionated by SFC (CHIRALPAK™ IF/SFC (Daicel Chemical Industries, Ltd.) (3 cmφ×25 cm), elution solvent methanol/carbon dioxide=40:60 (v/v), 120 bar, 40° C., flow rate: 100 mL/min.) and the title compound with a shorter retention time was obtained (121.4 mg). The X-ray crystal structure of the title compound is shown in FIG. 1.

$^1$H-NMR (400 MHz, CDCl$_3$) δ(ppm): 1.79 (s, 3H), 1.94 (s, 3H), 2.42-2.60 (m, 4H), 2.42-2.62 (m, 1H), 2.65-2.83 (m, 2H), 3.11 (br.s, 2H), 3.46 (br.d, J=14.6 Hz, 1H), 3.53-3.94 (m, 5H), 5.13-532 (m, 2H).

MS (ESI) m/z: 391 [M+H]$^+$

SFC Analysis:

(Analysis conditions) Column: CHIRALPAK™ IF-3/ SFC (Daicel Chemical Industries, Ltd.) (03 cmφ×5.0 cm), 40° C., elution solvent: methanol/carbon dioxide=40:60 (v/v), 1500 psi, flow rate: 1.2 mL/min., detection: UV (210-400 nm)

(Analysis results) The retention time of the title compound was 0.88 minutes and the optical purity was >99% ee.

Example 11

Synthesis of (+)-(3a,14a-cis)-5,10-dimethyl-1,3,3a, 5,6,9,10,11,12,14a-decahydrofuro[3,4-f]pyrido[4", 3":4',5']thieno[2',3':4,5]pyrimido[1,2-a][1,4]diaz-epine-4,13-dione

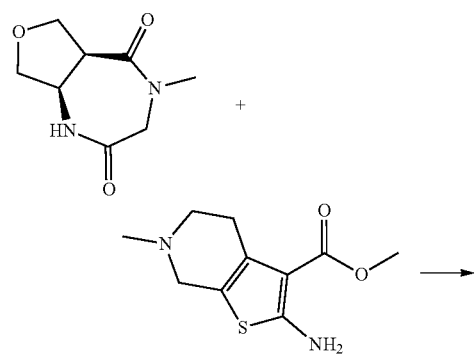

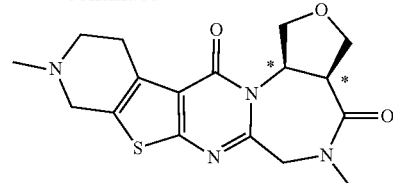

* single isomer but absolute configuration is not detrmined

To a mixture of (5aSR,8aRS)-4-methylhexahydro-1H-furo[3,4-e][1,4]diazepine-2,5-dione obtained in Production Example 12 (43 mg, 0.233 mmol), methyl 2-amino-6-methyl-4,5,6,7-tetrahydrothieno[2,3-c]pyridine-3-carboxy-late obtained in Production Example 2 (CAS No. 303998-84-7) (79 mg, 0350 mmol) and DCE (3 mL) was added phosphorus oxychloride (0.087 mL, 0.934 mmol) at room temperature. The reaction mixture was stirred at 80° C. for 2 hours and then cooled to room temperature, and then an aqueous saturated sodium hydrogencarbonate solution (3 mL) was added. The resulting mixture was stirred at room temperature for 16 hours and then directly purified by column chromatography (NH silica gel, 50-90%, ethyl acetate/heptane) to give a racemic mixture of the title compound.

MS (ESI) m/z: 361 [M+H]$^+$

After optical resolution of the racemic mixture of the title compound by SFC (CHIRALPAK™ OD-H/SFC (Daicel Chemical Industries, Ltd.) (2 cmφ×25 cm), elution solvent: methanol/carbon dioxide=20/80, flow rate: 70 mL/min.), the title compound with a shorter retention time was obtained (21.9 mg).

$^1$H-NMR (400 MHz, CDCl3) δ(ppm): 2.50 (s, 3H), 2.70-2.85 (m, 2H), 3.07-3.17 (m, 5H), 3.64 (s, 2H), 3.79 (ddd, J=11.2, 8.9, 4.9 Hz, 1H), 3.87 (dd, J=10.4, 4.1 Hz, 1H), 3.99 (d, J=15.6 Hz, 1H), 4.18-4.33 (m, 2H), 4.44 (dd, J=10.2, 4.7 Hz, 1H), 5.27 (d, J=16.0 Hz, 1H), 6.18 (ddd, J=11.4, 7.5, 4.1 Hz, 1H).

Example 12

Synthesis of (3aS,14aS)-5-methyl-10-(trifluorom-ethyl)-2,3,3a,5,6,14a-hexahydro-1H-benzofuro[3',2': 4,5]pyrimido[1,2-a]cyclopenta[f][1,4]diazepine-4, 13-dione

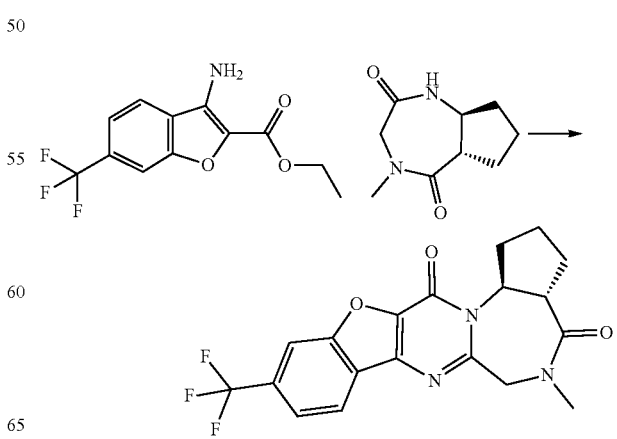

To a mixture of ethyl 3-amino-6-(trifluoromethyl)benzo-furan-2-carboxylate obtained in Production Example 13 (99.0 mg, 0362 mmol), (5aS,8aS)-4-methyloctahydrocyclopenta[e][1,4]diazepine-2,5-dione obtained in Production Example 14 (60.0 mg, 0329 mmol) and DCE (3 mL) was added phosphorus oxychloride (0.0460 mL, 0.494 mmol) at room temperature. The reaction mixture was stirred at 90° C. for 2 hours. An aqueous saturated sodium hydrogencarbonate solution (1 mL) was added and stirring of the mixture was continued at 90° C. for 40 hours. After then adding morpholine (0.430 mL, 4.94 mmol) at room temperature, stirring was continued at 70° C. for 4 hours. Water and ethyl acetate were added to the reaction mixture, and the organic layer was separated. The aqueous layer was extracted again with ethyl acetate. The combined organic layers were dried over anhydrous sodium sulfate and filtered, and the filtrate was concentrated under reduced pressure. The residue was purified by column chromatography (silica gel, 0-10% methanol/ethyl acetate) to give the title compound (100 mg).

¹H-NMR (400 MHz, CDCl₃) δ(ppm): 1.38-1.48 (m, 1H), 1.73-1.88 (m, 1H), 1.90-2.27 (m, 3H), 3.08-3.20 (m, 3H), 3.21-3.35 (m, 1H), 3.45-3.65 (m, 1H), 4.32-4.56 (m, 2H), 5.29-5.53 (m, 1H), 7.62-7.79 (m, 1H), 7.84-8.00 (m, 1H), 8.08-8.22 (m, 1H)

MS (ESI) m/z: 392 [M+H]⁺

Example 13

Synthesis of (−)-12-(2-methoxyethyl)-7,7-dimethyl-1,2,3,6,7,10,11,12,13,15b-decahydro-5H,9H-pyrido[4″,3″:4′,5′]thieno[2′3′:4,5]pyrimido[1,2-a]pyrrolo[2,1-c][1,4]diazepine-5,9-dione

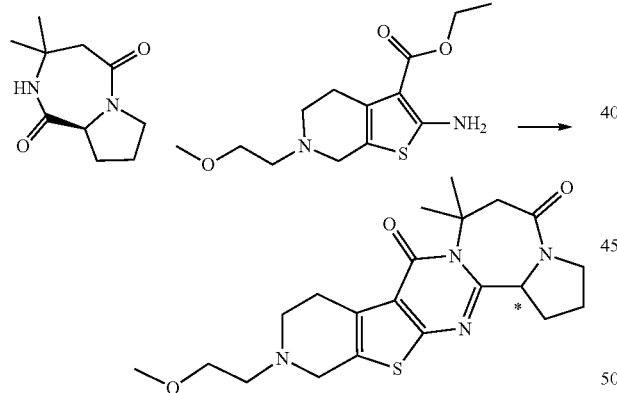

* Single isomer, but absolute configuration is not determined.

To a mixture of ethyl 2-amino-6-(2-methoxyethyl)-4,5,6,7-tetrahydrothieno[2,3-c]pyridine-3-carboxylate obtained in Production Example 9 (500 mg, 1.76 mmol), (S)-3,3-dimethylhexahydro-1H-pyrrolo[1,2-a][1,4]diazepine-1,5(2H)-dione obtained in Production Example 15 (449 mg, 2.29 mmol) and DCE (25.0 mL) was added phosphorus oxychloride (0.819 mL, 8.79 mmol) at room temperature. The reaction mixture was stirred at 50° C. for 15 hours. Aqueous saturated sodium carbonate and ethyl acetate were added at 0° C., and the organic layer was separated and concentrated under reduced pressure. To a solution of the obtained residue in methanol (25.0 mL) was added a 1 N sodium hydroxide aqueous solution (1.76 mL, 1.76 mmol) at 0° C., after which the mixture was stirred at 0° C. for 1 hour and then restored to room temperature, and then a 1 N sodium hydroxide aqueous solution (1.76 mL, 1.76 mmol) was added and stirring was continued for 1 hour. After adding hydrochloric acid and ethyl acetate to the reaction mixture, the organic layer was separated and concentrated under reduced pressure. The residue was purified by column chromatography (NH silica gel, 30-50%, ethyl acetate/n-heptane) to give a racemate of the title compound. This racemate of the title compound was fractionated by SFC (CHIRALPAK™ IA/SFC (Daicel Chemical Industries, Ltd.) (3 cmφ×25 cm), elution solvent: methanol/carbon dioxide=25:75 (v/v), 120 bar, 40° C., flow rate: 100 mL/min.) and the title compound with a longer retention time was obtained (104 mg).

¹H-NMR (400 MHz, CDCl₃) δ(ppm): 1.79 (s, 3H), 1.82-1.96 (m, 5H), 2.44 (dq, J=13.6, 6.9 Hz, 1H), 2.53 (d, J=15.1 Hz, 1H), 2.75-3.00 (m, 5H), 3.09 (br.t, J=53 Hz, 2H), 333-3.49 (m, 5H), 3.58 (t, J=5.5 Hz, 2H), 3.72-3.85 (m, 3H), 5.01 (t, J=6.4 Hz, 1H).

MS (ESI) m/z: 417 [M+H]⁺

SFC Analysis:

(Analysis conditions) Column: CHIRALPAK™ IA-3/SFC (Daicel Chemical Industries, Ltd.) (0.3 cmφ×5.0 cm), 40° C., elution solvent: methanol/carbon dioxide=25:75 (v/v), 1500 psi, flow rate: 12 mL/min., detection: UV (210-400 nm)

(Analysis results) The retention time of the title compound was 1.67 minutes and the optical purity was >99% ee.

HPLC Analysis:

(Analysis conditions) Column: CHIRALPAK™ IA (Daicel Chemical Industries, Ltd.) (0.46 cmφ×15 cm), 40° C., elution solvent: ethanol/hexane=50/50 (v/v), flow rate: 1 ml/min., detection: UV (254 nm)

(Analysis results) The retention time of the title compound was 4.26 minutes, the optical purity was >99% ee and the optical rotation was (−).

Example 14

Synthesis of (3aR,14aR)-5,9-dimethyl-2,3,3a,5,6,8,9,10,11,14a-decahydro-1H-cyclopenta[f]pyrido[3″,4″:4′,5′]thieno[3′,2′:4,5]pyrimido[1,2-a][1,4]diazepine-4,13-dione

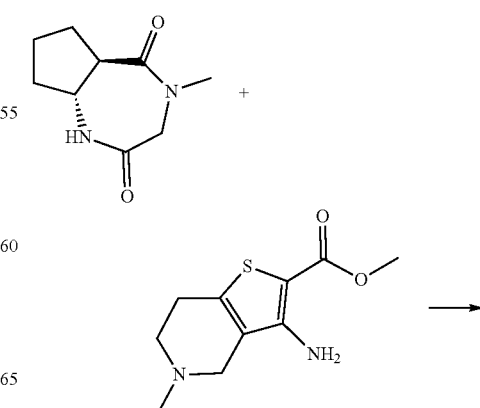

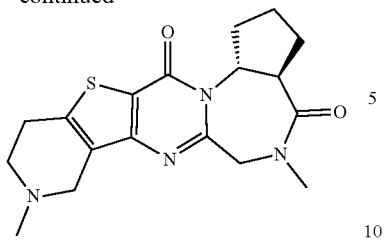

To a mixture of (5aR,8aR,)-4-methyloctahydrocyclopenta[e][1,4]diazepine-2,5-dione obtained in Production Example 6 (0.100 g, 0.549 mmol), methyl 3-amino-5-methyl-4,5,6,7-tetrahydrothieno[3,2-c]pyridine-2-carboxylate obtained in Production Example 16 (0.186 g, 0.823 mmol) and DCE (9 mL) was added phosphorus oxychloride (0.153 mL, 1.65 mmol) at room temperature. The reaction mixture was stirred at 80° C. for 2 hours, and then after cooling the reaction mixture to room temperature, an aqueous saturated sodium hydrogencarbonate solution (3 mL) was added. The reaction mixture was subsequently stirred at room temperature for 2 days, filtered with ISOLUTE™ (Biotage) HM-N and rinsed with 20 mL of ethyl acetate. The resulting solution was concentrated under reduced pressure. The residue was purified by column chromatography (NH silica gel, 60-90 ethyl acetate/n-heptane). The resulting solid was triturated with diethyl ether and the precipitate was collected by filtration. The obtained solid was rinsed with diethyl ether to give the title compound (104 mg).

$^1$H-NMR (400 MHz, CDCl$_3$) δ(ppm): 133-1.49 (m, 1H), 1.69-2.23 (m, 4H), 2.54 (s, 3H), 2.76-2.88 (m, 2H), 2.98-3.03 (m, 2H), 3.10 (s, 3H), 3.15-3.24 (m, 1H), 3.42-3.55 (m, 1H), 3.55-3.71 (m, 2H), 4.22-4.40 (m, 2H), 5.32 (d, J=17.2 Hz, 1H).

MS (ESI) m/z: 359 [M+H]$^+$

Example 15

Synthesis of (3aR,10R,14aR)-10-fluoro-2,5-dimethyl-2,3,3a,5,6,9,10,11,12,14a-decahydro-1H-benzo[4',5']thieno[2',3':4,5]pyrimido[1,2-a]pyrrolo[3,4-f][1,4]diazepine-4,13-dione

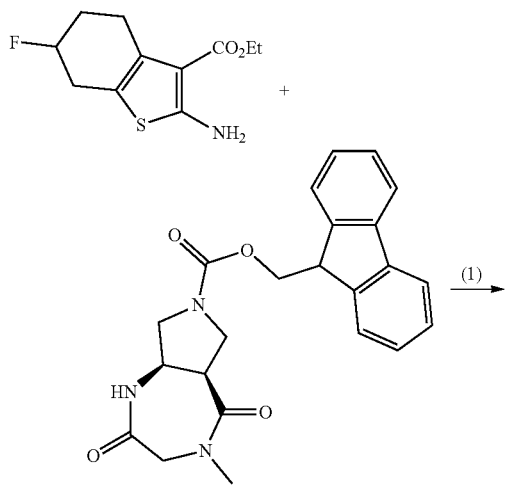

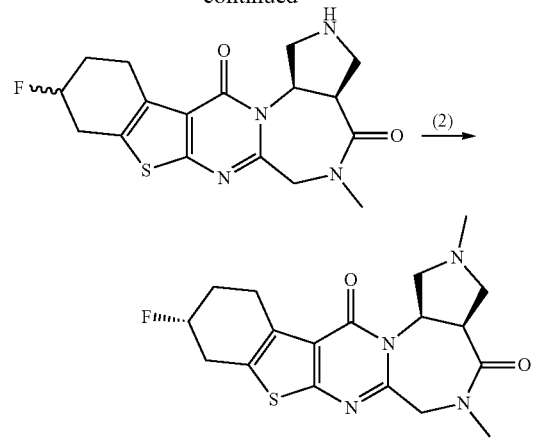

(1) Synthesis of (3aR,14aR)-10-fluoro-5-methyl-2,3,3a,5,6,9,10,11,12,14a-decahydro-1H-benzo[4',5']thieno[2',3':4,5]pyrimido[1,2-a]pyrrolo[3,4-f][1,4]diazepine-4,13-dione To a suspension of (9H-fluoren-9-yl)methyl (5aR,8aR)-4-methyl-2,5-dioxooctahydropyrrolo[3,4-e][1,4]diazepine-7(1H)-carboxylate obtained in Production Example 20 (224 mg, 0.522 mmol) and methyl 2-amino-6-fluoro-4,5,6,7-tetrahydrobenzo[b]thiophene-3-carboxylate obtained in Production Example 21 (190 mg, 0.829 mmol) in DCE (6.5 mL) was added phosphorus oxychloride (144 mg, 0.939 mmol) at room temperature.

The reaction mixture was stirred at 80° C. for 3 hours, and then after restoring the mixture to room temperature, methanol (0.782 mL, 193 mmol) was added and stirring was continued at room temperature for 20 minutes. After then adding morpholine (0.967 mL, 11.1 mmol) to the mixture at room temperature, it was stirred at 60° C. for 2 hours and 15 minutes.

The reaction mixture was restored to room temperature and concentrated under reduced pressure. DCM (4 mL) was added to the residue, and the resulting precipitate was collected by filtration and rinsed with DCM (6 mL). The filtrate was concentrated to half the amount, and then NH silica gel (2 g) was added to the residue and the mixture was concentrated. The residue was purified by column chromatography (NH silica gel, 50-100% ethyl acetate/n-heptane and 0 to 5% methanol/ethyl acetate) to give the title compound (126 mg).

$^1$H-NMR (400 MHz, CDCl$_3$) δ(ppm): 1.95-2.13 (m, 1H), 2.22 (dq, J=13.6, 6.8 Hz, 1H), 2.82 (dd, J=11.7, 7.8 Hz, 1H), 3.01-3.21 (m, 7H), 3.38 (dd, J=11.7, 7.8 Hz, 1H), 3.53-3.76 (m, 4H), 4.07 (dd, J=15.6, 2.7 Hz, 1H), 4.99-5.29 (m, 2H), 5.86-6.00 (m, 1H).

MS (ESI) m/z: 363 [M+H]$^+$ (2) Synthesis of (3aR,10R,14aR)-10-fluoro-2,5-dimethyl-2,3,3a,5,6,9,10,11,12,14a-decahydro-1H-benzo[4',5']thieno[2',3':4,5]pyrimido[1,2-a]pyrrolo[3,4-f][1,4]diazine-4,13-dione To a suspension of (3aR,14aR)-10-fluoro-5-methyl-2,3,3a,5,6,9,10,11,12,14a-decahydro 1H-benzo[4',5']thieno[2',3':4,5]pyrimido[1,2-a]pyrrolo[3,4-f][1,4]diazepine-4,13-dione (53 mg, 0.146 mmol) in THF (3 mL) was added an aqueous 37% formaldehyde solution (119 mg, 1.46 mmol).

The reaction mixture was stirred for 35 minutes at room temperature, and then sodium triacetoxyborohydride (37.2 mg, 0.175 mmol) was added at room temperature, and stirring was continued at room temperature for 55 minutes.

Figure 2:
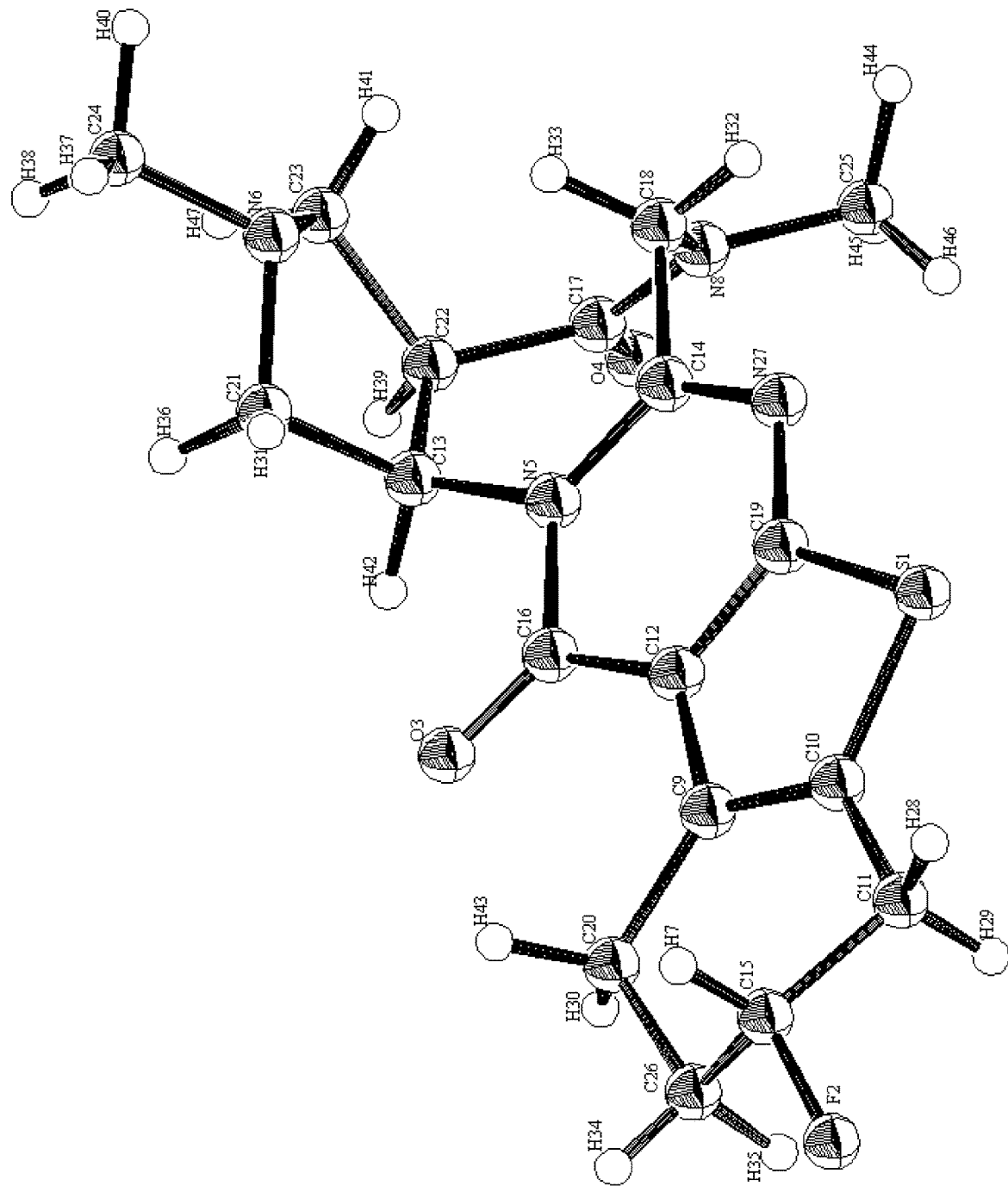
FIG. 2 is an ORTEP diagram showing the results of X-ray crystallographic analysis of the compound obtained in Example 15.

The reaction mixture was concentrated to ⅓ the amount, and then NH silica gel (1 g) was added to the residue and the mixture was concentrated. The resulting residue was purified by column chromatography (NH silica gel, ethyl acetate) to give a diastereomeric mixture of the title compound (47 mg). The obtained diastereomeric mixture (47 mg) was fractionated by HPLC (CHIRALPAK™ IA (2 cmφ×25 cm), elution solvent: ethanol, flow rate: 11 ml/min.) to give the title compound with a longer retention time (20.5 mg). The X-ray crystal structure of the title compound is shown in FIG. 2.

¹H-NMR (400 MHz, CDCl₃) δ(ppm): 1.95-2.13 (m, 1H), 2.14-2.26 (m, 1H), 2.37 (s, 3H), 2.77 (dd, J=10.5, 4.3 Hz, 1H), 2.92-3.03 (m, 2H), 3.03-3.21 (m, 7H), 3.25 (dd, J=10.4, 4.9 Hz, 1H), 3.69 (ddd, J=11.0, 8.9, 4.7 Hz, 1H), 3.89 (d, J=15.2 Hz, 1H), 5.03-5.24 (m, 1H), 5.92 (d, J=15.2 Hz, 1H), 6.11 (ddd, J=11.0, 83, 4.5 Hz, 1H).

MS (ESI) m/z: 377 [M+H]⁺

Example 16

Synthesis of (3aS,4aS)-10-(2-methoxyethyl)-5-methyl-2,3,3a,5,6,9,10,11,12,14a-decahydro-1H-cyclopenta[f]pyrido[4'',3'':4',5']thieno[2',3':4,5]pyrimido[1,2-a][1,4]diazepine-4,13-dione

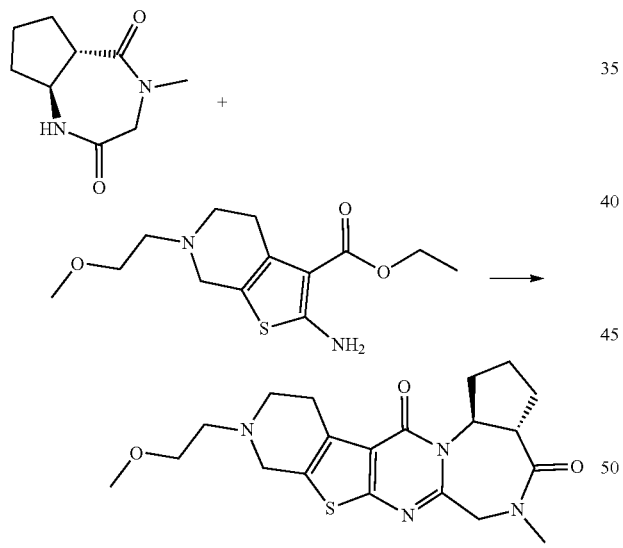

To a mixture of (5aS,8aS)-4-methyloctahydrocyclopenta[e][1,4]diazepine-2,5-dione obtained in Production Example 14 (37.4 mg, 0.205 mmol), ethyl 2-amino-6-(2-methoxyethyl)-4,5,6,7-tetrahydrothieno[2,3-c]pyridine-3-carboxylate obtained in Production Example 9 (38.9 mg, 0.137 mmol) and DCE (3 mL) was added phosphorus oxychloride (0.051 mL, 0.547 mmol) at room temperature. The reaction mixture was stirred at 80° C. for 2 hours and then cooled to room temperature, and an aqueous saturated sodium hydrogencarbonate solution (3 mL) was added. The resulting mixture was stirred at 70° C. for 48 hours, at 100° C. for 5 hours and at 70° C. for 16 hours, in that order. After cooling the mixture to room temperature, it was directly purified by column chromatography (NH silica gel, 50-70% ethyl acetate/n-heptane). The obtained crude product was purified by thin-layer chromatography (NH silica gel, 70% ethyl acetate/n-heptane) to give the title compound (19.6 mg).

¹H-NMR (400 MHz, CDCl₃) δ(ppm): 1.31-1.46 (m, 1H), 1.69-2.22 (m, 4H), 2.81 (t, J=5.4 Hz, 2H), 2.84-2.96 (m, 2H), 3.05-3.20 (m, 6H), 3.39 (s, 3H), 3.44-3.52 (m, 1H), 3.54-3.68 (m, 2H), 3.78 (d, J=2.3 Hz, 2H), 4.18-4.34 (m, 2H), 5.30 (d, J=172 Hz, 1H).

MS (ESI) m/z: 403 [M+H]⁺

Example 17

Synthesis of (−)-(3a,14a-trans)-2-(2-fluoroethyl)-5-methyl-2,3,3a,5,6,14a-hexahydro-1H-benzofuro[3',2':4,5]pyrimido[1,2-a]pyrrolo[3,4-f][1,4]diazepine-4,13-dione

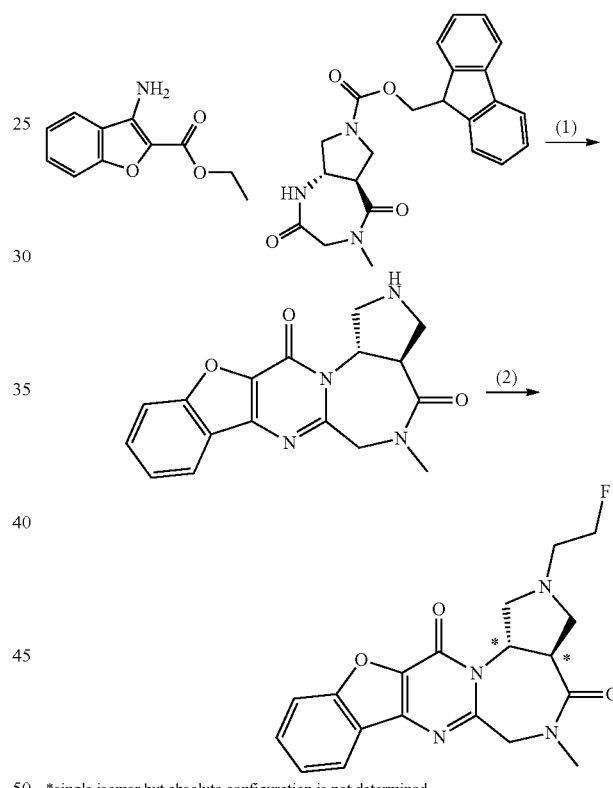

*single isomer but absolute configuration is not determined (1) Synthesis of (3aRS,14aSR)-5-methyl-2,3,3a,5,6,14a-hexahydro-1H-benzofuro[3',2':4,5]pyrimido[1,2-a]pyrrolo[3,4-f][1,4]diazepine-4,13-dione To a mixture of (5aRS,8aSR)-(9H-fluoren-9-yl)methyl 4-methyl-2,5-dioxooctahydropyrrolo[3,4-e][1,4]diazepine-7(1H)-carboxylate obtained in Production Example 18 (300 mg, 0.740 mmol), ethyl 3-aminobenzofuran-2-carboxylate (CAS No. 39786-35-1) (228 mg, 1.11 mmol) and DCE (6 mL) was added phosphorus oxychloride (138 μL, 1.48 mmol) at 25° C. The reaction mixture was stirred at 60° C. for 17 hours and then cooled to room temperature, and ethanol (130 mL, 223 mmol) was added. The resulting mixture was stirred at room temperature for 10 minutes, after which morpholine (2.00 mL, 23.0 mmol) was added and the mixture was stirred at 60° C. for 1 hour. It was then concentrated under reduced pressure. DCM (3 mL) was added to the residue and the mixture was filtered. A procedure of rinsing the filtered product with DCM (1 mL) was repeated 5 times. The combined filtrates were concentrated under reduced pressure and the residue was purified by column chromatography (NH silica gel, 0-20% methanol/ethyl acetate) to give the title compound (122 mg).

$^1$H-NMR (400 MHz, CDCl$_3$) δ(ppm): 2.72-2.83 (m, 1H), 3.16 (s, 3H), 3.37 (dd, J=10.5, 7.0 Hz, 1H), 3.56 (t, J=10.4 Hz, 1H), 3.80-3.97 (m, 1H), 4.46-4.64 (m, 3H), 5.43 (d, J=17.2 Hz, 1H), 7.41-7.51 (m, 1H), 7.57-7.72 (m, 2H), 7.97-8.09 (m, 1H).

MS (ES) m/z: 325 [M+H]$^+$ (2) Synthesis of (−)-(3a,14a-trans)-2-(2-fluoroethyl-5-methyl-2,3,3a,5,6,14a-hexahydro-1H-benzofuro[3',2':4,5]pyrimido[1,2-a]pyrrolo[3,4-f][1,4]diazepine-4,13-dione To a mixture of (3aRS,14aSR)-5-methyl-2,3,3a,5,6,14a-hexahydro-1H-benzofuro[3',2':4,5]pyrimido[1,2-a]pyrrolo[3,4-f][1,4]diazepine-4,13-dione (61 mg, 0.188 mmol) and DMF (1.20 mL) were added triethylamine (79.0 μL, 0.564 mmol) and 2-fluoroethyl tosylate (CAS No. 383-50-6) (48.1 μL, 0.282 mmol) at 25° C. The reaction mixture was stirred at 25° C. for 4 days, and then 2-fluoroethyl tosylate (CAS No. 383-50-6) (16.0 μL, 0.0939 mmol) was added. The resulting mixture was then stirred at 25° C. for 1 day and directly purified by column chromatography (NH silica gel, 30-100%, ethyl acetate/n-heptane and 0-15% methanol/ethyl acetate) to give a racemate of the title compound. After optical resolution of the racemate by HPLC (CHIRALPAK™ IG (3 cmφ×25 cm), elution solvent: ethanol, flow rate: 12 mL/min.), the title compound with a short retention time was obtained (7.81 mg).

$^1$H-NMR (400 MHz, CDCl$_3$) δ(ppm): 2.89-3.19 (m, 7H), 3.38 (dd, J=9.4, 6.3 Hz, 1H), 3.96 (dd, J=10.9, 8.6 Hz, 1H), 4.01-4.11 (m, 1H), 4.47 (t, J=4.9 Hz, 1H), 4.53 (d, J=18.7 Hz, 1H), 4.59 (t, J=4.9 Hz, 1H), 4.67 (dt, J=12.3, 8.5 Hz, 1H), 5.41 (d, J=18.0 Hz, 1H), 7.43-7.50 (m, 1H), 7.58-7.72 (m, 2H), 8.03 (d, J=8.2 Hz, 1H).

MS (ESI) m/z: 371 [M+H]$^+$

HPLC Analysis:

(Analysis conditions) Column: CHIRALPAK™ IG (Daicel Chemical Industries, Ltd.) (0.46 cmφ×15 cm), 40° C., elution solvent: ethanol, flow rate: 2 ml/min., detection: UV (254 nm)

(Analysis results) Upon analysis of the title compound under the conditions described above, the retention time was 14.4 minutes, the optical purity was >99% ee and the optical rotation was (−).

Pharmacological Test Examples

The following pharmacological test was conducted using the compounds of Examples 1 to 17.

Measurement of Acetylcholine (ACh) Release in the Rat Primary Septal Neuron Culture System (1) Rat Primary Septal Neuron Culture The septal area was isolated from Sprague-Dawley (SD) rats (Charles River Laboratories Japan, Inc.) at a fetal age of 18 days, and cultured. Specifically, fetuses were removed from pregnant rats under isoflurane anesthesia. The brain was extracted from each fetus, and immersed in ice-cooled L-15 medium (11415-064, Thermo Fisher Scientific). The septal area was dissected from the extracted brain under a stereoscopic microscope. The dissected septal area was treated in 0.25% trypsin (15050-065, Thermo Fisher Scientific) and 0.01% DNase (D5025-150KU, Sigma) at 37° C. for 30 minutes, thereby dispersing the cells. In this case, the enzyme reaction was terminated by adding inactivated horse serum (26050-088, Thermo Fisher Scientific). The enzyme-treated solution was centrifuged at 1000 rpm for 3 minutes, and the supernatant was removed. A medium in an amount of 10 mL was added to the obtained cell mass. The medium used was Dulbecco's Modified Eagle's Medium (044-29765, WAKO) supplemented with N2 supplement (17502-048, Thermo Fisher Scientific), 1 mM sodium pyruvate (11360-070, Thermo Fisher Scientific), and Penicillin-Streptomycin (15140-1221, Thermo Fisher Scientific). The cells of the cell mass to which the medium was added were redispersed by gentle pipetting, and then centrifuged again at 1000 rpm for 3 minutes, and the supernatant was removed. The medium in an amount of 10 mL was added to the obtained cell mass, and the cell dispersion was filtered through a 40-μm nylon mesh (Cell Strainer) to remove the cell mass, thereby obtaining a neuronal cell suspension. The neuronal cell suspension was diluted with the medium, and 10% inactivated bovine serum (26140-079, Thermo Fisher Scientific) and 10% inactivated horse serum were added. Thereafter, 100 μL/well of the suspension was seeded in a 96-well plate (354461, CORNING) pre-coated with poly-D-lysine so that the initial culture density was $1.2 \times 10^5$ cells/cm$^2$. After the seeded cells were cultured under 5% CO$_2$-95% air in a 37° C. incubator for 2 days, the entire medium was replaced with 120 μL of fresh medium, and the cells were subsequently cultured for 5 days.

(2) Compound Addition

On the 7th day of culture, compounds were added in the following manner. A solution of the test compound in DMSO was diluted with the medium so that the concentration was 10 times higher than the final concentration. Nerve Growth Factor (450-01, PEPRO TECH, INC.) was prepared at 03 ng/mL. These two solutions were added each in an amount of 15 μL/well, and the mixture was mixed well. The final DMSO concentration was 0.1% or less. Moreover, only DMSO and NGF were added to the control group.

(3) ACh Release Measurement

One day after the compound addition, an amount of ACh release was measured by HPLC in the following manner. A warmed buffer was added at 100 μL/well to the well after the medium was eliminated, and the buffer was immediately removed. Thereafter, a buffer to which 10 μm choline, 10 μm physostigmine, and 6 mM KCl were added was added at 120 μL/well. The buffer was prepared by adding 125 mM NaCl, 25 mM 4-(2-hydroxyethyl)-1-piperazineethanesulfonic acid, 1.2 mM KH$_2$PO$_4$, 1.2 mM MgSO$_4$, 2.2 mM CaCl$_2$ (2H$_2$O), and 10 mM glucose to sterilized water, and the final pH of the solution was set to 7.4. After the 96-well plate to which the buffer was added was incubated under 5% CO$_2$-95% air in a 37° C. incubator for 40 minutes, 80 μL of buffer was collected. An internal standard solution IPHC ($5 \times 10^{-7}$ M) was added in an amount of 6 μL to the collected buffer, and the buffer was transferred to a tube for HPLC measurement and subjected to HPLC measurement. The results are represented by the effect of each compound as the percentage (% of control) of the ACh concentration in the buffer of the control group, and the compound concentrations showing a 20% increase from the ACh concentration in the buffer of the control group are shown in the following Table 1.

TABLE 1

| Example | Concentration (µM) showing a 20% or more increase from the amount of ACh in the control group |
|---|---|
| 1 | 0.03 |
| 2 | 0.03 |
| 3 | 0.03 |
| 4 | 0.1 |
| 5 | 0.03 |
| 6 | 0.03 |
| 7 | 0.3 |
| 8 | 0.03 |
| 9 | 0.03 |
| 10 | 0.03 |
| 11 | 0.03 |
| 12 | 0.03 |
| 13 | 0.03 |
| 14 | 0.03 |
| 15 | 0.3 |
| 16 | 0.03 |
| 17 | 0.03 |

Measurement of Choline Acetyltransferase (ChAT) mRNA Expression Levels in the Rat Septal Area (1) Compound Administration In this study, Sprague-Dawley male rats (Charles River Laboratories Japan, Inc.) with a body weight of about 250 to 350 g were used. The test compound was dissolved in 0.01 mol/L hydrochloric acid, and orally administered.

(2) Sampling

At 24 hours after the administration of the compound, the whole brain tissue was collected under pentobarbital anesthesia. The medial septum was isolated from whole brain on ice and frozen with liquid nitrogen, and then stored at −80° C.

(3) Measurement of ChAT mRNA Expression Levels

For RNA purification, RNeasy™ Plus Mini Kit (#74136: QIAGEN) was used in this study. RNA purification was performed by the method described in the kit After RNA purification, the total RNA concentration was measured by using QIAxpert Instrument (QIAGEN). cDNA was synthesized using SuperScript™ VILO™ cDNA Synthesis Kit (#11754: Thermo Fisher Scientific). The synthesis of cDNA was performed by the method described in the kit. The synthesized cDNA was diluted 4 times with RNase free water, and the diluted cDNA solution was used as a sample. Taqman™ Universal PCR Master Mix (#4304437: Thermo Fisher Scientific), Taqman™ Gene Expression Assays, INVENTORIED (#4331182: Thermo Fisher Scientific), RNase free water, and the cDNA solution were mixed in amounts of 10 µL, 1 µL, 4 µL, and 5 µL, respectively, and the resulting mixture was used as a measurement sample solution. Quantitative polymerase chain reaction (qPCR) was conducted using ABI PRISM™ 7900HT (Thermo Fisher Scientific) by a fluorescence probe method. Analysis was performed by SDS 2.4 (Thermo Fisher Scientific). The results were calculated by the percentage of the amount of ChAT mRNA expression levels in the compound administration group increased from the amount of ChAT mRNA expression levels in the vehicle administration group. The results are shown in the following Table 2.

TABLE 2

| Example | Dose | Amount (%) increased from the amount of ChAT mRNA expression levels in the vehicle administration group |
|---|---|---|
| 1 | 10 mg/kg | 76.0 |
| 2 | 3 mg/kg | 53.6 |
| 3 | 1 mg/kg | 53.7 |
| 4 | 1 mg/kg | 51.5 |
| 5 | 1 mg/kg | 54.1 |
| 6 | 0.3 mg/kg | 67.7 |
| 7 | 3 mg/kg | 76.6 |
| 8 | 3 mg/kg | 71.8 |
| 9 | 3 mg/kg | 111.5 |
| 10 | 1 mg/kg | 50.6 |
| 11 | 1 mg/kg | 54.7 |
| 12 | 1 mg/kg | 44.7 |
| 13 | 1 mg/kg | 59.7 |
| 14 | 1 mg/kg | 63.6 |
| 15 | 1 mg/kg | 49.0 |
| 16 | 3 mg/kg | 42.5 |
| 17 | 3 mg/kg | 44.6 |

What is claimed is:

1. A compound selected from the group consisting of (3aS,14aR)-5-Methyl-3,3a,5,6-tetrahydro-1H-benzofuro[3',2':4,5]pyrimido[1,2-a]cyclopenta[f][1,4]diazepine-4,13(2H,14aH)-dione:

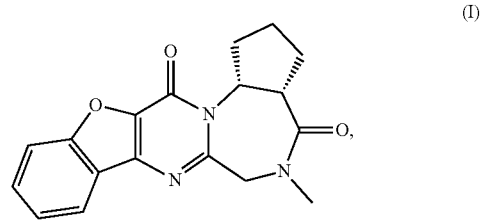 [SMILES: CN1Cc2nc3c(oc4ccccc43)c(=O)n2[C@@H]2CCC[C@@H]2C1=O]

(I)

(+)-7,7,12-Trimethyl-1,2,3,6,7,10,11,12,13,15b-decahydropyrido[4",3":4',5']thieno[2',3':4,5]pyrimido[1,2-a]pyrrolo[2,1-c][1,4]diazepine-5,9-dione:

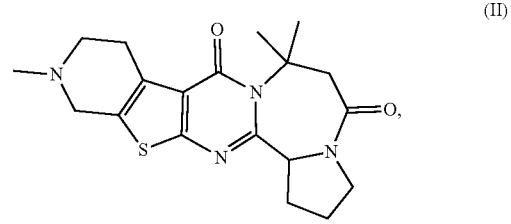 [SMILES: CN1CCc2c(sc3nc4n(c(=O)c23)C(C)(C)CC(=O)N2CCCC42)C1]

(II)

(3aS,14aR)-10-Fluoro-5-methyl-3,3a,5,6-tetrahydro-1H-benzofuro[3',2':4,5]pyrimido[1,2-a]cyclopenta[f][1,4]diazepine-4,13(2H,14aH)-dione:

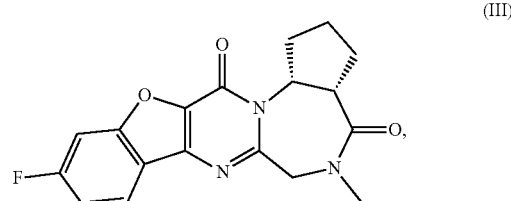

(III)

(3aS,14aR)-5,8,10-Trimethyl-3,3a,5,6-tetrahydro-1H-cyclopenta[f]pyrido[3",2":4',5']furo[3',2':4,5]pyrimido[1,2-a][1,4]diazepine-4,13(2H,14aH)-dione:

(IV)

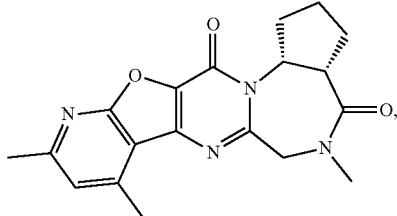

(3aR,14aR)-10-Fluoro-5-methyl-3,3a,5,6-tetrahydro-1H-benzofuro[3',2':4,5]pyrimido[1,2-a]cyclopenta[f][1,4]diazepine-4,13(2H,14aH)-dione:

(V)

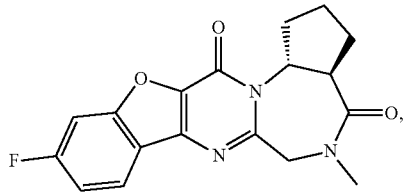

(3aR,14aR)-5-Methyl-10-(trifluoromethyl)-3,3a,5,6-tetrahydro-1H-benzofuro[3',2':4,5]pyrimido[1,2-a]cyclopenta[f][1,4]diazepine-4,13(2H,14aH)-dione:

(VI)

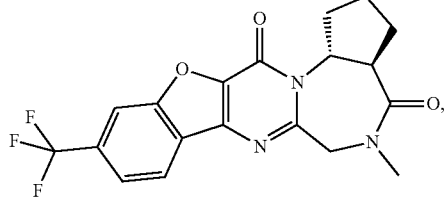

(3aS,14aR)-10-(2,2-Difluoroethyl)-5-methyl-2,3,3a,5,6,9,10,11,12,14a-decahydro-1H-cyclopenta[f]pyrido[4",3":4',5']thieno[2',3':4,5]pyrimido[1,2-a][1,4]diazepine-4,13-dione:

(VII)

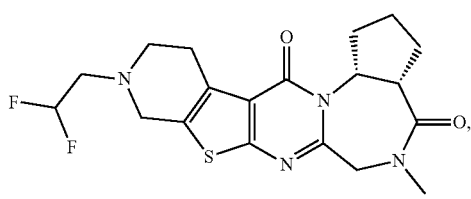

(3aS,14aR)-10-(2-Methoxyethyl)-5-methyl-2,3,3a,5,6,9,10,11,12,14a-decahydro-1H-cyclopenta[f]pyrido[4",3":4',5']thieno[2',3':4,5]pyrimido[1,2-a][1,4]diazepine-4,13-dione:

(VIII)

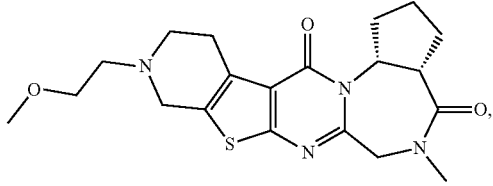

(3aS,14aR)-10-(Difluoromethyl)-5-methyl-3,3a,5,6-tetrahydro-1H-benzofuro[3',2':4,5]pyrimido[1,2-a]cyclopenta[f][1,4]diazepine-4,13(2H,14aH)-dione:

(IX)

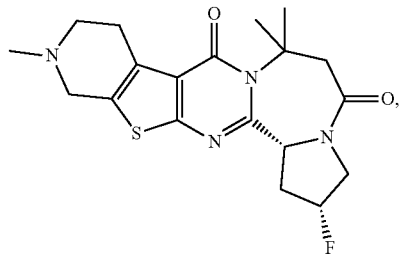

(2R,15bR)-2-Fluoro-7,7,12-trimethyl-1,2,3,6,7,10,11,12,13,15b-decahydro-5H,9H-pyrido[4",3":4',5']thieno[2',3':4,5]pyrimido[1,2-a]pyrrolo[2,1-c][1,4]diazepine-5,9-dione:

(X)

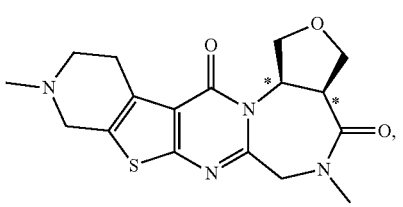

(+)-(3a,14a-cis)-5,10-Dimethyl-1,3,3a,5,6,9,10,11,12,14a-decahydrofuro[3,4-f]pyrido[4",3":4',5']thieno[2',3':4,5]pyrimido[1,2-a][1,4]diazepine-4,13-dione:

(XI)

*relative configuration (3aS,14aS)-5-Methyl-10-(trifluoromethyl)-2,3,3a,5,6,14a-hexahydro-1H-benzofuro[3',2':4,5]pyrimido[1,2-a]cyclopenta[f][1,4]diazepine-4,13-dione:

(XII)

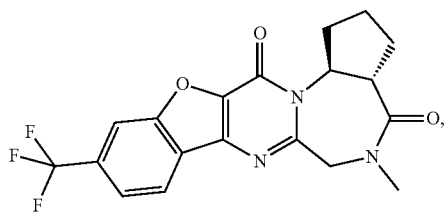

(+12-(2-Methoxyethyl)-7,7-dimethyl-1,2,3,6,7,10,11,12,13,15b-decahydro-5H,9H-pyrido[4'',3'':4',5']thieno[2',3':4,5]pyrimido[1,2-a]pyrrolo[2,1-c][1,4]diazepine-5,9-dione:

(XIII)

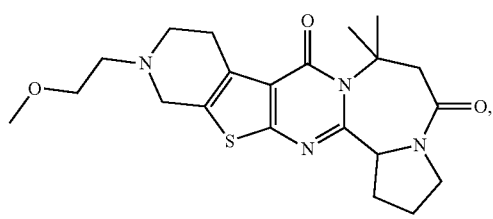

(3aR,14aR)-5,9-Dimethyl-2,3,3a,5,6,8,9,10,11,14a-decahydro-1H-cyclopenta[f]pyrido[3'',4'':4',5']thieno[3',2':4,5]pyrimido[1,2-a][1,4]diazepine-4,13-dione:

(XIV)

(3aR, 10R,14aR)-10-Fluoro-2,5-dimethyl-2,3,3a,5,6,9,10,11,12,14a-decahydro-1H-benzo[4',5']thieno[2',3':4,5]pyrimido[1,2-a]pyrrolo[3,4-f][1,4]diazepine-4,13-dione:

(XV)

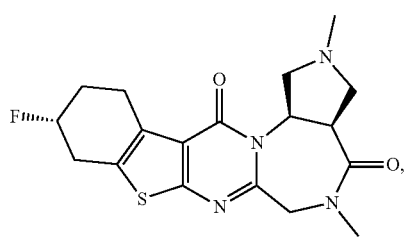

(3aS,14aS)-10-(2-methoxyethyl)-5-methyl-2,3,3a,5,6,9,10,11,12,14a-decahydro-1H-cyclopenta[f]pyrido[4'',3'':4',5']thieno[2',3':4,5]pyrimido[1,2-a][1,4]diazepine-4,13-dione:

(XVI)

and (−)-(3a,14a-trans)-2-(2-fluoroethyl)-5-methyl-2,3,3a,5,6,14a-hexahydro-1H-benzofuro[3',2': 4,5]pyrimido[1,2-a]pyrrolo[3,4-f][1,4]diazepine-4,13-dione:

(XVII)

*relative configuration or a pharmaceutical salt thereof.

2. A pharmaceutical composition comprising the compound or pharmaceutically acceptable salt thereof according to claim 1 and one or more pharmaceutically acceptable excipients.

3. A method for treating cognitive dysfunction in a patient with Alzheimer's disease or dementia with Lewy bodies, comprising administering to the patient the compound or pharmaceutically acceptable salt thereof according to claim 1.

4. The method of claim 3, wherein the patient has Alzheimer's disease.

5. The method of claim 3, wherein the patient has dementia with Lewy bodies.

* * * * *

UNITED STATES PATENT AND TRADEMARK OFFICE
CERTIFICATE OF CORRECTION

PATENT NO. : 11,358,972 B2  
APPLICATION NO. : 16/807335  
DATED : June 14, 2022  
INVENTOR(S) : Yoshiaki Ohashi et al.

Page 1 of 1

It is certified that error appears in the above-identified patent and that said Letters Patent is hereby corrected as shown below:

On the Title Page

Column 2, Item (57), ABSTRACT

Line 7, delete " 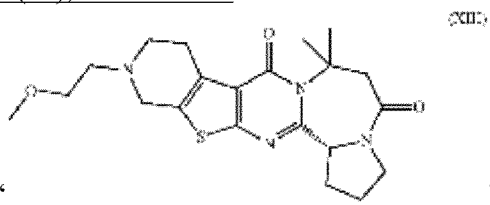 " and insert 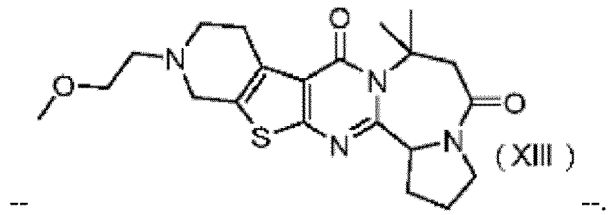 -- --.

In the Claims

Column 56
Claim 1, Line 66, delete "[3',2':4,5']" and insert -- [3',2':4,5] --.

Column 57
Claim 1, Line 12, delete "(+12" and insert -- (-)-12 --.
Claim 1, Line 45, delete "(3aR, 10R,14aR)" and insert -- (3aR,10R,14aR) --.

Column 58
Claim 1, Line 22, delete "[3',2': 4,5]" and insert -- [3',2':4,5] --.

Signed and Sealed this  
Fourth Day of October, 2022

*Katherine Kelly Vidal*

Katherine Kelly Vidal  
*Director of the United States Patent and Trademark Office*